US006815539B1

(12) United States Patent
Salkoff et al.

(10) Patent No.: US 6,815,539 B1
(45) Date of Patent: Nov. 9, 2004

(54) PH SENSITIVE POTASSIUM CHANNEL IN SPERMATOCYTES

(75) Inventors: Lawrence Salkoff, Clayton, MO (US); Matthew Schreiber, Clayton, MO (US); Chris Silvia, Durham, NC (US)

(73) Assignees: Icagen, Incorporated, Durham, NC (US); The Washington University, St. Louis, MO (US)

(*) Notice: Subject to any disclaimer, the term of this patent is extended or adjusted under 35 U.S.C. 154(b) by 0 days.

(21) Appl. No.: 09/176,664

(22) Filed: Oct. 21, 1998

Related U.S. Application Data
(60) Provisional application No. 60/076,172, filed on Feb. 27, 1998, and provisional application No. 60/063,138, filed on Oct. 22, 1997.

(51) Int. Cl.[7] .................. C07H 21/04; C07K 14/47; C12N 15/12

(52) U.S. Cl. ............ 536/23.5; 435/69.1; 435/253.1; 435/320.1; 435/325; 530/350; 530/300; 536/23.1; 536/24.31; 424/130.1

(58) Field of Search .................. 435/69.1, 253.1, 435/320.1, 325; 536/23.1, 23.5, 24.31; 530/300, 350; 424/130.1

(56) References Cited

PUBLICATIONS

Adelman, John P. et al. "Calcium–activated potassium channels expressed from cloned complementary DNAs." *Neutron*, 9:209–216 (1992).

Arnoult, Christophe et al. "Activation of mouse sper t–type $Ca^{2+}$ channels by adhesion to the egg zona pellucida." *Proc. Natl. Acad. Sci. USA* 93:13004–13009 (1996).

Atkinson, Nigel S. et al. "A component of calcium–activated potassium channels encoded by the Drosophila slo locus." *Science*, 253:551–555 (1991).

Brayden, Joseph E. and Nelson,. "Regulation of arterial tone by activation of calcium–dependent potassium channels." *Science*, 256:532–535 (1992).

Butler, Alice et al. "mSlo, a complex mouse gene encoding "maxi" calcium–activated potassium channels." *Science*, 261:221–224 (1993).

Cook, Sean P. and Babcock,. "Selective Modulation by cGMP of the $K^+$ channel activated by speract." *Journal of Biological Chemistry.*, 268:22402–22407 (1993).

Dworetzky, Steven I. et al. "Cloning and expression of a human large–conductance calcium–activated potassium channel." *Molecular Brain Research*, 27:189–183 (1994).

Elkins, Thomas et al. "A Drosophila mutation that eliminates a calcium–dependent potassium current." *Proc. Natl. Acad. Sci. USA*, 83:8415–8419 (1986).

Florman, Harvey M. "Activation of voltage–dependent calcium channels of mammalian sperm is required for zona pellucida–induced acrosomal exocytosis." *Developmental Biology*, 132:304–314 (1992).

Fuchs, Paul A. "Development of frequency turning in the auditory periphery." *Current Opinion in Neurobiology*, 2:457–461, 1992.

Hartmann, Hali A. et al. Exchange of conduction pathways between two related $K^+$ channels. *Science*, 251:942–944 (1991).

Heginbotham, Lise et al. "Mutations in the $K^+$ channel signature sequence." *Biophysical Journal*, 66:1061–1067 (1994).

Knaus, Hans–Gunther et al. "Distribution of high–conductance $Ca^{2+}$–activated $K^+$ channels in rat brain: targeting to axons and nerve terminals." *Journal of Neuroscience*, 16:955–963 (1996).

Liévano, Arturo et al. "T–type $Ca^{2-}$ channels and $\alpha_{1E}$ expression in spermatogenic cells, and their possible relevance to the sperm acrosome reaction." *FEBS Letters* 388:150–154 (1996).

Marty, A. "Ca–dependent K channels with large unitary conductance in chromaffin cell membranes." *Nature*, 291:497–500 (1981).

McCobb, David P. et al. "A human calcium–activated potassium channel gene expressed in vascular smooth muscle." *Am. J. Physiol.*, 269:H767–H777 (1995).

Neely, Alan and Lingle, C.J. "Two components of calcium–activated potassium current in rat adrenal chromaffin cells." *Journal of Physiology*, 453:97–131 (1992).

Pallotta, Barry S. et al. "Single channel recordings of $Ca^{2+}$–activated $K^+$ currents in rat muscle cell culture." *Nature*, 293:471–474 (1981).

Peterson, Ole H. and Maruyama, Y. "Calcium–activated potassium channels and their role in secretion." *Nature* (Review Article), 307:693–696 (1984).

Robitaille, Richard and Charlton, M.P. "Presynaptic calcium signals and transmitter release are modulated by calcium–activated potassium channels." *The Journal of Neuroscience*, 12:297–305 (1992).

Santi, Celia M. et al. "A dihydropyridine–sensitive T–type Ca2+ current is the main $Ca^{2+}$ current carrier in mouse primary spermatocytes." *Am. J. Physiol.*, 271:C1583–1593 (1996).

Schreiber, Matthew et al. "Slo3, a novel pH–sensitive $K^+$ channel from mammalian spermatocytes." *The Journal of Biological Chemistry*, 273:3509–3516 (1998).

Schreiber, Matthew and Salkoff, L. "Novel calcium–sensing domain in the BK channel." *Biophysical Journal*, 73:1355–1363 (1997).

(List continued on next page.)

Primary Examiner—Yvonne Eyler
Assistant Examiner—Nirmal S. Basi
(74) Attorney, Agent, or Firm—Townsend and Townsend and Crew LLP

(57) ABSTRACT

The invention provides isolated nucleic acid and amino acid sequences of Slo3, a pH sensitive potassium channel expressed in sperm; antibodies to Slo3; methods of screening for Slo3 inhibitors; and methods of screening for Slo3 homologs.

10 Claims, 14 Drawing Sheets

OTHER PUBLICATIONS

Tabcharani, Joseph A. and Misler, S. "$Ca^{2+}$–activated $K^+$ channel in rat pancreatic islet B cells: permeation, gating and blockade by cations." *Biochim. Biophys. Acta*, 982:62–72 (1989).

Tseng–Crank, Julie et al. Cloning, expression, and distribution of functionally distinct $Ca^{2+}$–activated $K^+$ channel isoforms from human brain. *Nature*, 13:1315–1330 (1994).

Wallner, M. et al. "Characterization of and modulation by a β–subunit of a human maxi $K_{Ca}$ channel cloned from myometrium." *Receptors and Channels*, 3:185–199 (1995).

Wei, A. et al. "Eight potassium channel families revealed by the *C. elegans* genome project." *Neuropharmacology*, 35:805–829 (1996).

Wei, Aguan et al. "Calcium sensitivity of BK–type $K_{Ca+}$ channels determined by a separable domain." *Neuron*, 13:671–681 (1994).

Weyland, Ingo et al. "Cloning and functional expression of a cyclic–nucleotide–gated channel from mammalian sperm." *Nature* (Letters):368–859–863 (1994).

Wu, Y.–C. et al. "A. kinetic description of the calcium–activated potassium channel and its application to electrical tuning of hair cells." *Prog. Biophys. Molec. Biol.*, 63:131–158 (1995).

Yool, Andrea J. and Schwarz, T.L. "Alteration of ionic selectivity of a $K^+$ channel by mutation of the H5 region." *Nature* (Letters), 349:700–704 (1991).

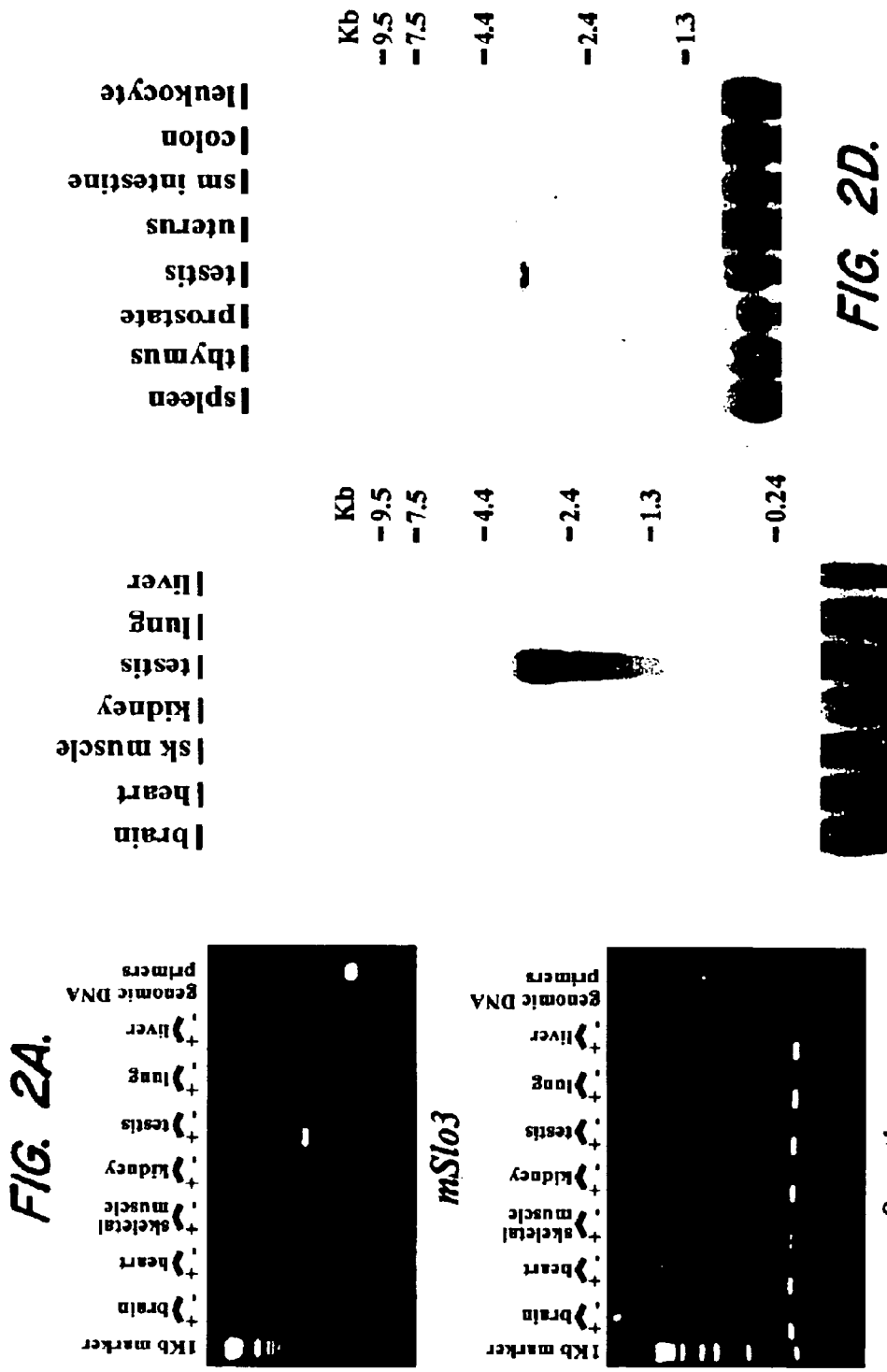

FIG. 3D.
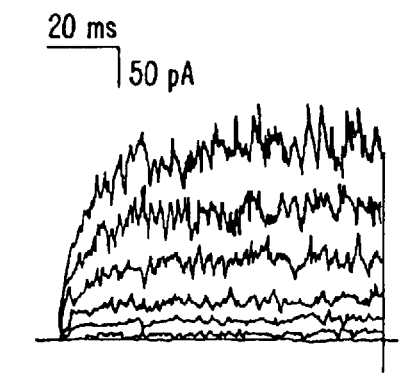
● pH 8 - 100 μM [Ca$^{2+}$]
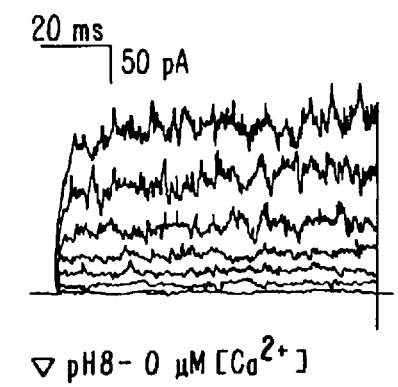
▽ pH 8 - 0 μM [Ca$^{2+}$]
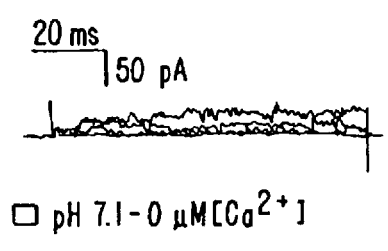
□ pH 7.1 - 0 μM [Ca$^{2+}$]
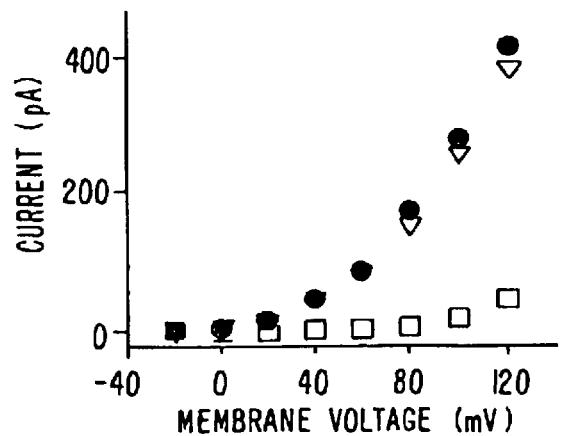

PH SENSITIVE POTASSIUM CHANNEL IN SPERMATOCYTES

CROSS-REFERENCES TO RELATED APPLICATIONS

This application claims the benefit of U.S. Ser. No. 60/063,138, filed Oct. 22, 1997, and U.S. Ser. No. 60/076,172, filed Feb. 27, 1998, both of which are incorporated by reference.

STATEMENT AS TO FEDERALLY SPONSORED RESEARCH AND DEVELOPMENT

This invention was made with Government support under Grant No. RO1-NS24785, awarded by the National Institutes of Health. The Government has certain rights in this invention.

FIELD OF THE INVENTION

The invention provides isolated nucleotide and amino acid sequences of Slo3, a pH sensitive potassium channel expressed in sperm; antibodies to Slo3; methods if of screening for Slo3 inhibitors and activators; and methods of identifying Slo3 homologs.

BACKGROUND OF THE INVENTION

Potassium channels are found in a wide variety of animal cells such as nervous, muscular, glandular, immune or epithelial tissue. The channels regulating these currents open and allow the escape of potassium under certain conditions. The outward flow of potassium ions upon opening of these channels makes the interior of the cell more negative, counteracting depolarizing voltages applied to the cell. These channels are regulated, e.g., by calcium sensitivity, voltage-gating, and ATP-sensitivity.

The Drosophila Slo1 gene encodes a calcium-activated potassium channel present in both neurons and muscle (Elkins et al., *Proc. Natl. Acad. Sci. U.S.A.* 83:8415 (1986); Atkinson et al., *Science* 253:551 (1991); and Adelman et al., *Neuron* 9:209 (1992)). Mammalian homologs of dSlo1 were cloned and found to be "Maxi" or BK (large conductance) channel types, as the single channel conductance was 272 pS with symmetrical potassium concentrations. Slo1 channels cloned from mouse and human show strong conservation of sequence and functional properties (Butler et al., *Science* 261:221–224 (1993); Dworetzky et al., *Brain Res. Mol. Brain Res.* 27:189–193 (1994); Tseng-Crank et al., *Neuron* 13:1315–1330 (1994); McCobb et al., *Am. J. Physiol.* 269:H767–H777 (1995); and Wallner et al., *Rec. Chan.* 3:185–199 (1995)). One proposed role of the Slo1 channel is to provide negative feedback for the entry of calcium into cells via voltage-dependent calcium channels. Perhaps because of the versatility of this mechanism, Slo1 channels are expressed in many tissues, including brain, skeletal and smooth muscle, auditory hair cells, pancreas, and adrenal gland (Marty, *Nature* 291:497–500 (1981); Pallotta et al., *Nature* 293:471–474 (1981); Petersen & Mauryama, *Nature* 307:693–696 (1984); Tabcharani & Misler, *Biochim. Biophys. Acta.* 982:62–72 (1990); Neely & Lingle, *J. Physiol.* 453:97–131 (1992)). In these tissues, Slo1 channels are involved in diverse functions such as regulating arteriolar smooth muscle tone (Brayden & Nelson, *Science* 256:532–535 (1992)), tuning of hair cell frequency (Fuchs, *Curr. Op. Neurobiol.* 2:457–461 (1992); Wu et al., *Prog. Biophys. Mol. Bio.* 63:131–158 (1996)), and modulation of transmitter release at nerve terminals (Robitaille & Charlton, *J. Neurosci.* 12:297–305 (1995); Knaus et al., *J. Neurosci.* 16:955–963 (1996)), all situations in which both membrane potential and intracellular calcium are critical factors. While numerous family members of every type of voltage-gated $K^+$ channel have been found, to date the Slo1 channel has remained the sole functionally characterized representative of the Slo family (Wei et al., *Neuropharmacology* 35:805–829 (1996)).

Spermatocytes require proteins tailored to fulfill roles unique to the process of germ cell development and fertilization. Cellular signaling in spermatic cells is tightly regulated to prevent inappropriate activation of the irreversible steps that prepare the sperm to fertilize the oocyte. Many of these steps are triggered and coordinated by changes in membrane potential and intracellular $Ca^{2+}$ concentration and pH. Between mating and fertilization, sperm undergo capacitation, a process which later enables them to fertilize the oocyte. Capacitation involves an increase in cytosolic pH (pHi), which promotes metabolic and swimming activity (Babcock et al., *Proc. Natl. Acad. Sci. USA* 80:1327–1331 (1983); Babcock & Pfeiffer, *J. Biol. Chem.* 262:15041–15047 (1987); Vredenburgh-Wilberg & Parrish, *Mol. Reprod. Dev.* 40:490–502 (1995)). This increase in pHi is accompanied by changes in membrane potential and a rise in cytoplasmic $Ca^{2+}$, which trigger the acrosome reaction upon contact with the oocyte (Arnoult et al., *J. Cell Biol.* 134:637–645 (1996); Florman, *Dev. Biol.* 165:152–164 (1994)). Because of the central importance of these events in development, many efforts have been made to identify the specific proteins, including ion channels, which regulate spermatic function. In particular, there have been reports of channels present in spermatocytes and spermatids that have been proposed to play central roles in these reactions (Cook & Babcock, *J. Biol. Chem.* 268:22402–22407 (1993), including voltage dependent calcium channels (Florman et al., *Dev. Biol.* 152:304–214 (1992); Arnoult et al., *Proc. Natl. Acad. Sci. USA* 93:13004–13009 (1996); Lievano et al., *FEBS Lett.* 388:150–154(1996); Santi et al., *Am. J. Physiol.* 271:C1583–C1593 (1996)). Apart from a cyclic nucleotide gated channel, however, few of these channels have been directly cloned from testis (Weyand et al., *Nature* 368:859–863 (1994)).

SUMMARY OF THE INVENTION

Potassium channels have evolved to play specialized roles in many inexcitable tissues. The present invention provides for the first time isolated nucleotide and amino acid sequences of Slo3, a potassium channel with novel functional properties, abundantly expressed in spermatocytes. The physiological reactions that sperm undergo to achieve fertilization include changes in both pHi and membrane potential. Although Slo3 is a member of the Slo family, to which the large-conductance, calcium-activated Slo1 potassium channel belongs, Slo3 channels are not gated by calcium. Slo3 channels, however, are activated by changes in intracellular pH and membrane potential. Slo3 channels also exhibit markedly lower selectivity for $K^+$ over $Na^+$ than most voltage-gated $K^+$ channels.

In one aspect, the invention provides an isolated nucleic acid encoding a polypeptide monomer of a pH sensitive potassium channel. The monomer (i) has a calculated molecular weight of between 120–156 kDa; (ii) has a unit conductance of approximately 80–120 pS when the monomer is in a functional tetrameric form of a potassium channel and is expressed in a Xenopus oocyte; (iii) has increased activity above approximately intracellular pH of 7.1; and (iv) specifically binds to polyclonal antibodies generated against SEQ ID NO:1, SEQ ID NO:3, SEQ ID NO:16 or SEQ ID NO:18.

In one embodiment, the nucleic acid encodes mSlo3 or hSlo3. In another embodiment, the nucleic acid encodes SEQ ID NO:1, SEQ ID NO:16, or SEQ ID NO:18. In one embodiment, the nucleic acid selectively hybridizes under moderate stringency hybridization conditions to SEQ ID NO:2, SEQ ID NO:4, SEQ ID NO:17, or SEQ ID NO:19. In one embodiment, the nucleic acid has a nucleotide sequence of SEQ ID NO:2, SEQ ID NO:4, SEQ ID NO:17, or SEQ ID NO:19.

In one embodiment, the nucleic acid is amplified by primers that selectively hybridize under stringent hybridization conditions to the same sequence as the primer sets selected from the group consisting of:

CTCGAACTCCCTAAAATCTTACAGAT (SEQ ID NO:8) and

TTCCGTTGAGCCAGGGGTCACCAGAATT (SEQ ID NO:9);

TCTGCTTTGTGAAGCTAAATCT (SEQ ID NO:10) and

TTTCAAAGCCTCTTTAGCGGTAA (SEQ ID NO:11); and

TTATGCCTGGATCTGCACTCTACATG (SEQ ID NO:12) and

ATAGTTTCCGTCTACTACCGAAA (SEQ ID NO:13).

In another embodiment, the nucleic acid is amplified by primers that selectively hybridize under stringent hybridization conditions to the same sequence as the primer sets selected from the group consisting of:

GGCAGCGCTCATTCTTTCCTCCTT (SEQ ID NO:14) and

TGCCCAAAACCTCAACCCAAAATA (SEQ ID NO:15).

In another aspect, the invention provides an isolated nuclcic acid encoding at least 15 contiguous amino acids from a pH sensitive potassium channel polypeptide monomer, said monomer having an amino acid sequence of SEQ ID NO:1, SEQ ID NO:16, or SEQ ID NO:18 and conservatively modified variants thereof.

In one embodiment, the nucleic acid encodes a pH sensitive potassium channel polypeptide monomer having: (i) a unit conductance of 80–120 pS when the monomer is in a functional tetrameric form of a potassium channel and is expressed in a Xenopus oocyte; (ii) a molecular weight of between 120–156 kDa; and (iii) increased activity above an intracellular pH of 7.1; and where the nucleic acid either: (i) selectively hybridizes under moderate stringency hybridization conditions to a nucleotide sequence of SEQ ID NO:2, SEQ ID NO:4, SEQ ID NO:17 or SEQ ID NO:19; or (ii) encodes a protein which could be encoded by a nucleic acid that selectively hybridizes under moderate stringency hybridization conditions to a nucleotide sequence of SEQ ID NO:2, SEQ ID NO:4, SEQ ID NO:17 or SEQ ID NO:19.

In another aspect, the invention provides an isolated nucleic acid encoding a polypeptide monomer of a pH sensitive potassium channel, the sequence: (i) encoding a monomer having a core domain that has greater than 60% amino acid sequence identity to amino acids 35–641 of an mSlo3 core domain as measured using a sequence comparison algorithm; and (ii) specifically binding to polyclonal antibodies raised against the core domain of SEQ ID NO:1, SEQ ID NO:3, SEQ ID NO:16, or SEQ D NO:18.

In another aspect, the invention provides an isolated polypeptide monomer of a pH sensitive potassium channel, the monomer: (i) having a calculated molecular weight of between 120–156 kDa; (ii) having a unit conductance of approximately 80–120 pS when the monomer is in a functional tetrameric form of a potassium channel and is expressed in a Xenopus oocyte; (iii) having increased activity above approximately intracellular pH of 7.1; and (iv) specifically binding to polyclonal antibodies generated against SEQ ID NO:1, SEQ ID NO:3, SEQ ID NO:16, or SEQ ID NO:18.

In another aspect, the invention provides an antibody that selectively binds to mSlo3 or hSlo3.

In another aspect, the invention provides an expression vector comprising a nucleic acid encoding a polypeptide monomer of a pH sensitive potassium channel, the monomer: (i) having a calculated molecular weight of between 120–156 kDa; (ii) having a unit conductance of approximately 80–120 pS when the monomer is in a functional tetrameric form of a potassium channel and is expressed in a Xenopus oocyte; (iii) having increased activity above approximately intracellular pH of 7.1; and (iv) specifically binding to polyclonal antibodies generated against SEQ ID NO:1, SEQ ID NO:3, SEQ ID NO:16, or SEQ ID NO:18.

In another aspect, the invention provides a host cell comprising the expression vector.

In another aspect, the invention provides a method for identifying a compound that increases or decreases ion flux through a pH sensitive potassium channel, the method comprising the steps of: (i) contacting the compound with a eukaryotic host cell or cell membrane in which has been expressed a pH sensitive potassium channel monomer polypeptide: (a) having a calculated molecular weight of between 120–156 kDa; (b) having a unit conductance of approximately 80–120 pS when the monomer is in the functional tetrameric form of a potassium channel and is expressed in a Xenopus oocyte; and (c) specifically binding to polyclonal antibodies generated against SEQ ID NO:1, SEQ ID NO:3, SEQ ID NO:16, or SEQ ID NO:18; and (ii) determining the functional effect of the compound upon the cell or cell membrane expressing the pH sensitive potassium channel.

In one embodiment, the increased or decreased flux of ions is determined by measuring whole cell conductance. In one embodiment, the pH sensitive potassium channel monomer polypeptide is recombinant.

In another aspect, the invention provides method of detecting the presence of Slo3 in mammalian tissue, the method comprising the steps of: (i) isolating a biological sample from a patient; (ii) contacting the biological sample with a Slo3-specific reagent that selectively binds to Slo3; and, (iii) detecting the level of Slo3-specific reagent that selectively associates with the sample.

In one embodiment, the Slo3 specific reagent is selected from the group consisting of: Slo3 specific antibodies, Slo3 specific oligonucleotide primers, and Slo3 nucleic acid probes. In one embodiment, the sample is from a human.

In another aspect, the invention provides in a computer system, a method of screening for mutations of Slo3 genes, the method comprising the steps of: (i) receiving input of a first nucleic acid sequence encoding a pH sensitive potassium channel protein having a nucleotide sequence of SEQ ID NO:2, SEQ ID NO:4, SEQ ID NO:17, SEQ ID NO:19 and conservatively modified versions thereof; (ii) comparing the first nucleic acid sequence with a second nucleic acid sequence having substantial identity to the first nucleic acid sequence; and (iii) identifying nucleotide differences between the first and second nucleic acid sequences.

In one embodiment, the second nucleic acid sequence is associated with a disease state.

In another aspect, the invention provides in a computer system, a method for identifying a three-dimensional structure of Slo3 proteins, the method comprising the steps of: (i) receiving input of at least about 10 amino acids of an amino acid sequence of a pH sensitive potassium channel monomer or at least about 30 nucleotides of a nucleic acid encoding the protein, the protein having an amino acid sequence of SEQ ID NO:1, SEQ ID NO:3, SEQ ID NO:16, or SEQ ID NO:18, and conservatively modified versions thereof; and (ii) generating a three-dimensional structure of the protein encoded by the amino acid sequence.

In one embodiment, the amino acid sequence is a primary structure and said generating step includes the steps of: (i) forming a secondary structure from said primary structure using energy terms encoded by the primary structure; and (ii) forming a tertiary structure from said secondary structure using energy terms encoded by said secondary structure. In one embodiment, the generating step includes the step of forming a quaternary structure from said tertiary structure using anisotropy terms encoded by the tertiary structure. In one embodiment, the method further comprises the step of identifying regions of the three-dimensional structure of the protein that bind to ligands and using the regions to identify ligands that bind to the protein.

BRIEF DESCRIPTION OF THE DRAWINGS

FIGS. 1A(1–8)–B: Primary sequence of mSlo3 (SEQ ID NO:20)

FIGS. 1A(1–8): Alignment or imary use of mSlo3 with BK $Ca^{2+}$-activated $K^+$ channels mSlo1 (mouse) (SEQ ID NO:21) and dSlo1 (Drosophila) (SEQ ID NO:22). Hydrophobic segments are designated S0 through S10. Segments S1–S6 represent the transmembrane segments that surround pore of the channel. The region designated "Calcium Bowl" has been implicated in the regulation of mSlo1 by calcium. The core and tail domain structure of Slo1 has been conserved (Wei et al., Neuron 13:671–681 (1994)). mSlo3 residues 35 through 641 encompass S0 through S8, the core domain, and share 56% and 50% identity with mSlo1 and dSlo1 while interspecies homologs mSlo1 and dSlo1 exhibit 62% identity in this region. mSlo3 residues 686–1136 encompassing S9 and S10, the tail, share 39% identity with mSlo1 and dSlo1 while the interspecies homologs mSlo1 and dSlo1 share 68% identity in this region. A region having no significant homology between mSlo1 and mSlo3 is found between S8 and S9. An arrowhead indicates a phenylalanine residue (F) in a region critical for ion selectivity.

FIGS. 2A–D: Expression of mSlo3 transcripts is largely restricted to the testis

FIG. 2A: RT-PCR of mouse brain, heart, skeletal muscle, kidney, testis, lung and liver with mSlo3-specific primers, with (+) and without (−) addition of reverse transcriptase. An expected 156 bp product is detected only with testis RNA. Similar results were obtained with two additional mSlo3 primer pairs specific to S8 to S9 and S9 to S10 regions.

FIG. 2B: Control RT-PCR assays with M-actin specific primers produce an expected 537 bp product from all tissues. Additional negative controls with genomic DNA (10 ng) or primers alone are also shown.

FIG. 2C: Northern blot analysis of total RNA (20 mg) from mouse brain, heart, skeletal muscle, kidney, testis, lung and liver reveals an abundant mSlo3 transcript only in testis, with an approximate size of 4 kb.

FIG. 2D: Northern blot analysis of polyadenylated RNA (2 mg) from human tissues (spleen, thymus, prostate, testis, uterus, small intestine, colon, and leukocytes) with mSlo3, reveals a cross-hybridizing mRNA species only in testis, with an approximate size of 4 kb. For controls, the same blots were hybridized with a human β-actin probe and results are shown below.

FIGS. 3A–D: mSlo3 channel sensitivity to voltage and pH from individual inside-out patches FIG. 3A: Currents at constant voltage (+80 mV). Activity increases at higher pH. The cytoplasmic surface was exposed to recording solution at indicated pH; Npo at pH 7.1, 7.3, 7.6, and 8.0 was 0.000, 0.014, 0.031, and 0.258, respectively, based on the presence of a minimum of five channels.

FIG. 3B: Reversibility of pH effect. Activity in a single patch is shown sequentially from top to bottom at indicated pH.

FIG. 3C: Currents at constant pH 7.6. Activity increases at positive potentials.

FIG. 3D: Macroscopic current traces and corresponding current-voltage relations. The diminished current at pH 7.1 was restored when the same patch was exposed to pH 8. The slight decrease in current amplitude between the conditions at pH 8 was likely due to current rundown. Holding potential was −40; on-line leak subtraction was employed.

FIG. 4A: Manipulation of intracellular pH alters current amplitude. (Left) Control currents at start of experiment. (Middle) Diminished current amplitude after intracellular acidification (12.5 minute perfusion with $NaHCO_3$ replacing NaCl in nd96). (Right) Recovery during alkalinization (10 minute perfiusion with nd96 supplemented with 30 mM $NH_4Cl$). Voltage families are from −80 to +60 mV in 10 mV increments.

FIG. 4B: Representative tail currents in 10 mM $K^+$, 88 mM $Na^+$ at 11° C.

FIG. 4C: Tail current amplitude versus voltage for the currents shown in FIG. 4B. Instantaneous currents at the time of the voltage jump were calculated from exponential fits of tail currents extrapolated back to time zero. Currents are plotted versus test potential (large filled squares). A Goldman-Hodgkin-Katz (GHK) current equation was fitted to the tail current-voltage relation (solid line) with $Na^+/K^+$ permeability ratio, P=0.15; calculated underlying $K^+$ (small triangles) and $Na^+$ (small squares) currents are also shown.

FIG. 4D: mSlo3 exhibits relatively low selectivity for $K^+$ over $Na^+$. Reversal potential was determined by measuring tail currents in varying external $[K^+]$; $[Na^+]$ was also varied so that the total monovalent concentration ($[K^+]+[Na^+]$) was 98 mM. Points were fitted with a GHK equation where the $Na^+/K^+$ permeability ratio, P, was allowed to vary freely. Drosophila Shab reversal potentials were determined as a control (Wei et al., 1990). For mSlo3 reversal potential at 2, 5, 10, 50, and 98 $[K^+]$, n=6, 3, 5, 6, 7, respectively; for dShab at 2, 10, 50, and 98, n=3, 1, 3, 3.

DETAILED DESCRIPTION OF THE INVENTION

I. Introduction

The present invention provides for the first time isolated nucleotide and amino acid sequences for Slo3 and demonstrates that Slo3 is a pH sensitive potassium, voltage-gated channel. Functionally, Slo3 is expressed in spermatocytes, is voltage-gated, and is pH sensitive. Furthermore, Slo3 exhibits markedly lower selectivity for $K^+$ over $Na^+$ than most voltage-gated potassium channels. Among a wide panel of tissues, both mSlo3 (mouse Sio3) and hSlo3 (human Slo3) mRNA were detected in testis, where the mRNA was abundantly expressed in developing spermatocytes. This expression pattern and sensitivity to both pH and voltage, indicate that Slo3 is involved in sperm capacitation and/or the acrosome reaction, essential steps in fertilization.

When mSlo3 protein (mouse Slo3) is recombinantly expressed in Xenopus oocytes, the homotetramer channel protein has a unitary conductance of between 80 and 120 pS (as measured with symmetrical potassium concentrations); and for example, at a concentration of 160 mM potassium, the channel has a conductance of 106 pS. Unitary conductance may be conveniently determined using single channel or macroscopic channel inside-out or outside-out patch clamp configurations or whole cell recordings (see Wei et al., 1994, supra). Patch clamp and whole cell recording methods are well known in the art (see, e.g., Franciolini, *Experientia*, 42:589–594 (1986); and Sakmann et al., *Annual Review of Physiology*, 46:455–472 (1984)).

The isolated Slo3 proteins within the scope of the present invention include those which when expressed in a cell from a quiet line, define a functionality and pharmacology indicative of a Slo3 channel. A quiet line is a cell line that in its native state (e.g., not expressing Slo3 channels) has low or uninteresting electric activity, e.g., a CHO cell line. For example, a control cell (without expression of a Slo3 channel of the present invention) and an experimental cell (expressing a Slo3 channel) are maintained under conditions standard for measurement of electrophysiological parameters as provided in the worling examples disclosed herein.

For example, a cell expressing a Slo3 channel of the present invention can have a conductance of between 80–120 pS, can comprise an Slo3 channel protein monomer of about 120 to 156 kD, can exhibit pH sensitivity (e.g., increased activity at above approximately pHi 7.1) and voltage-gating, can exhibit amino acid identity of at least 60%, and more preferably at least 70%, 80%, 90% or 95% in an alignment with the core domain of the exemplary mouse and human Slo3 channel sequences disclosed herein, and can be specifically reactive, under immunologically reactive conditions, with an antibody raised to an exemplary Slo3 sequence disclosed herein (e.g., SEQ ID NO:1, 3, 16 and 18). Such standard methods aid in the identification of Slo3 proteins of the present invention.

Figure 1A:
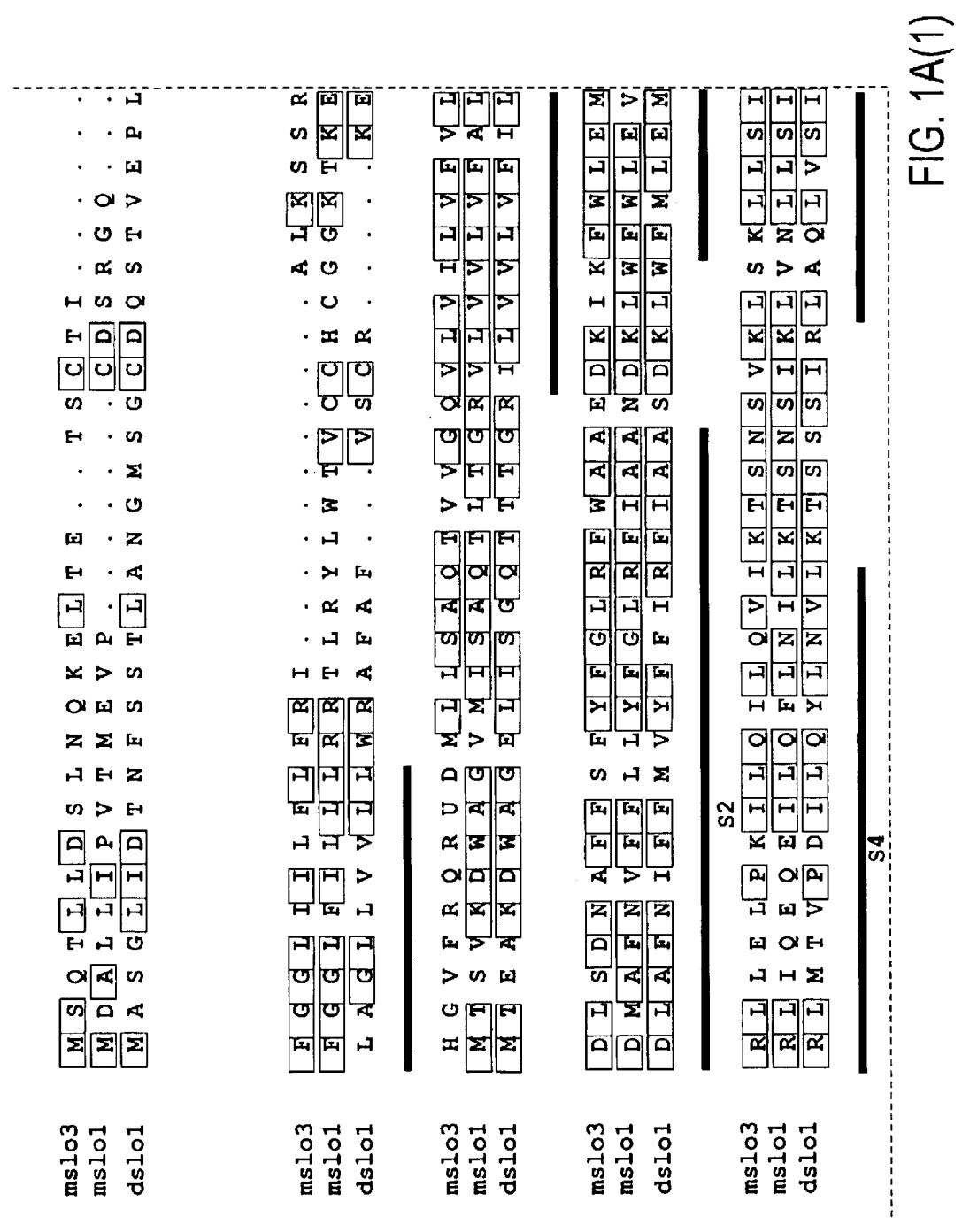
Figure 1A:
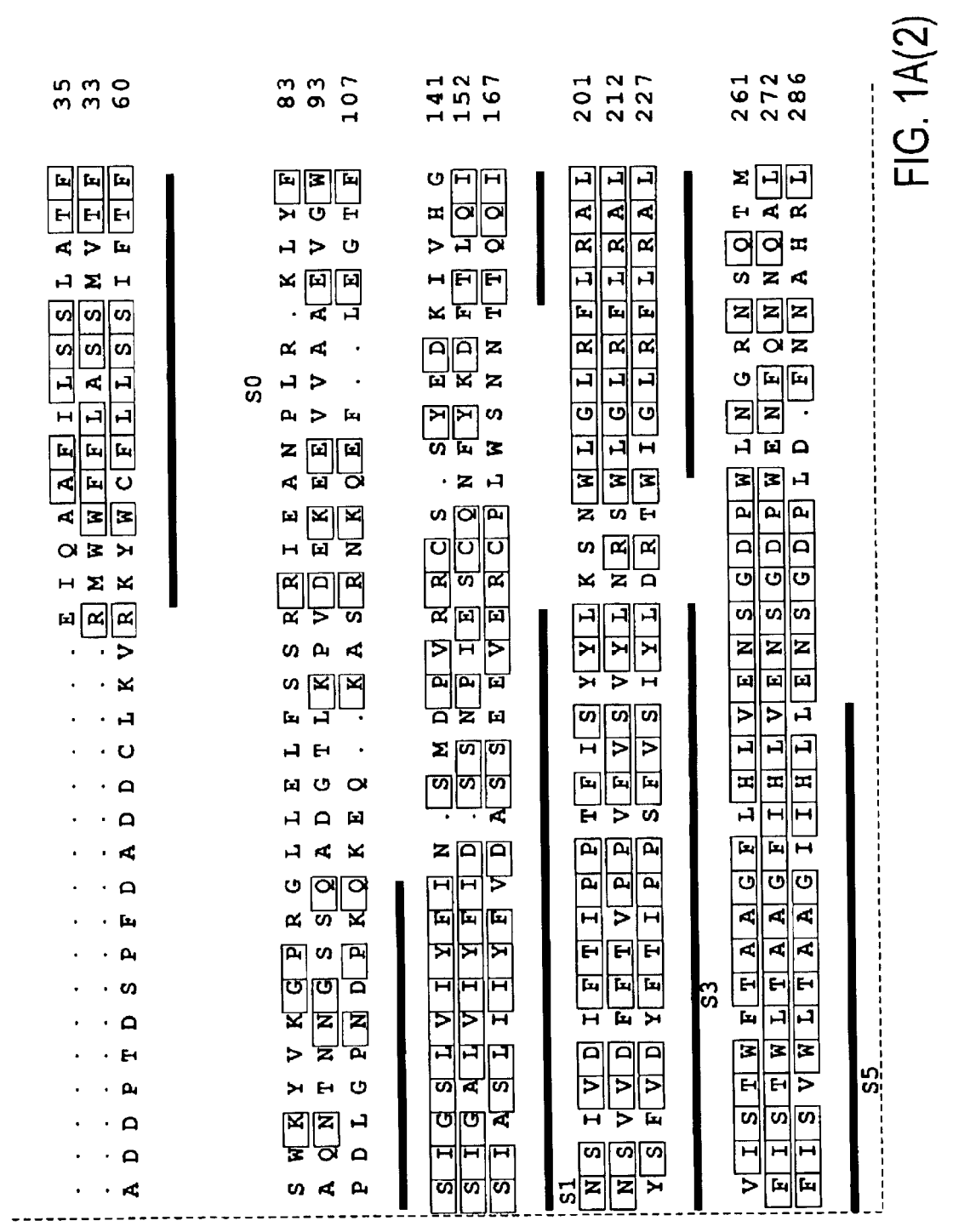
Figure 1A:
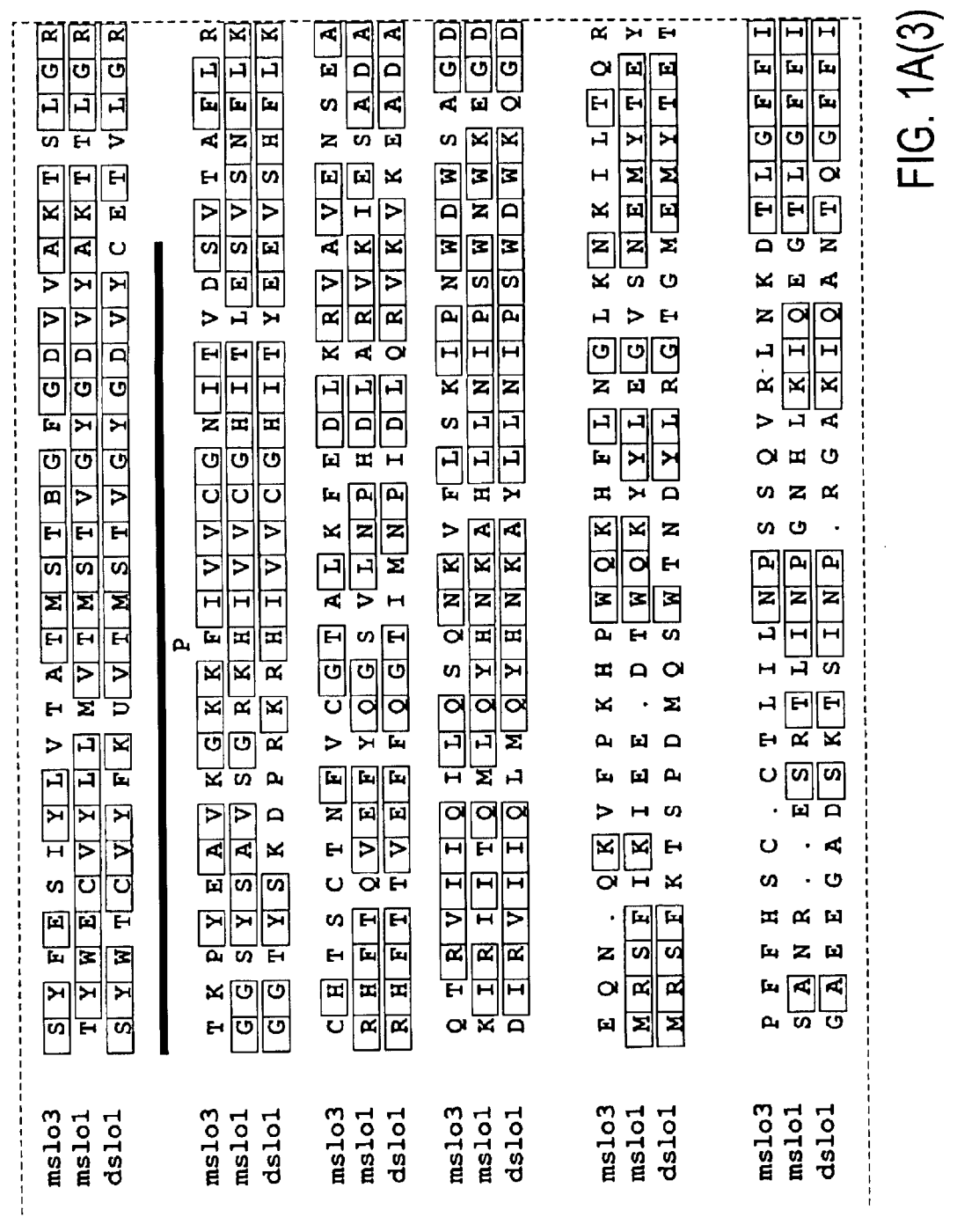
Figure 1A:
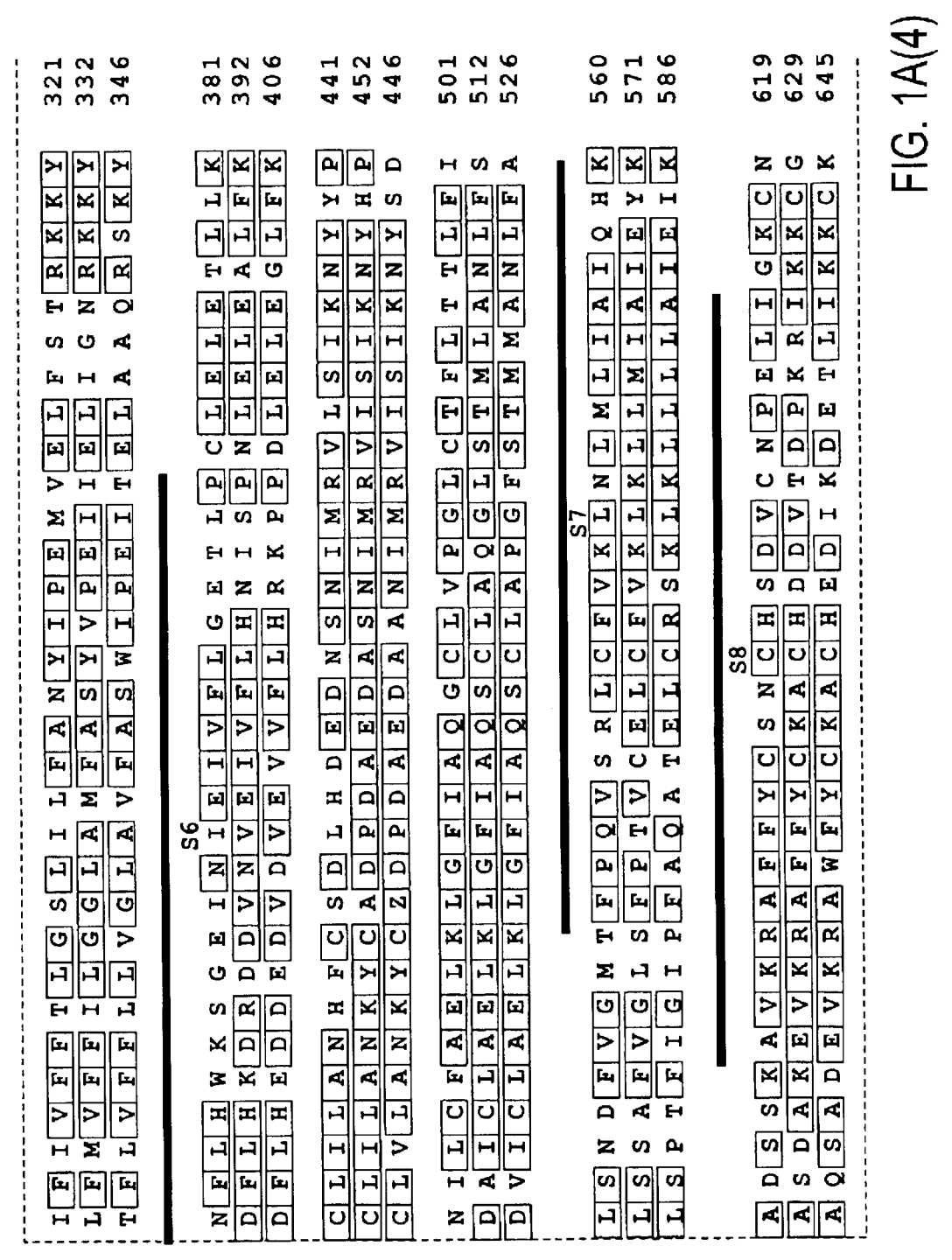
Figure 1A:
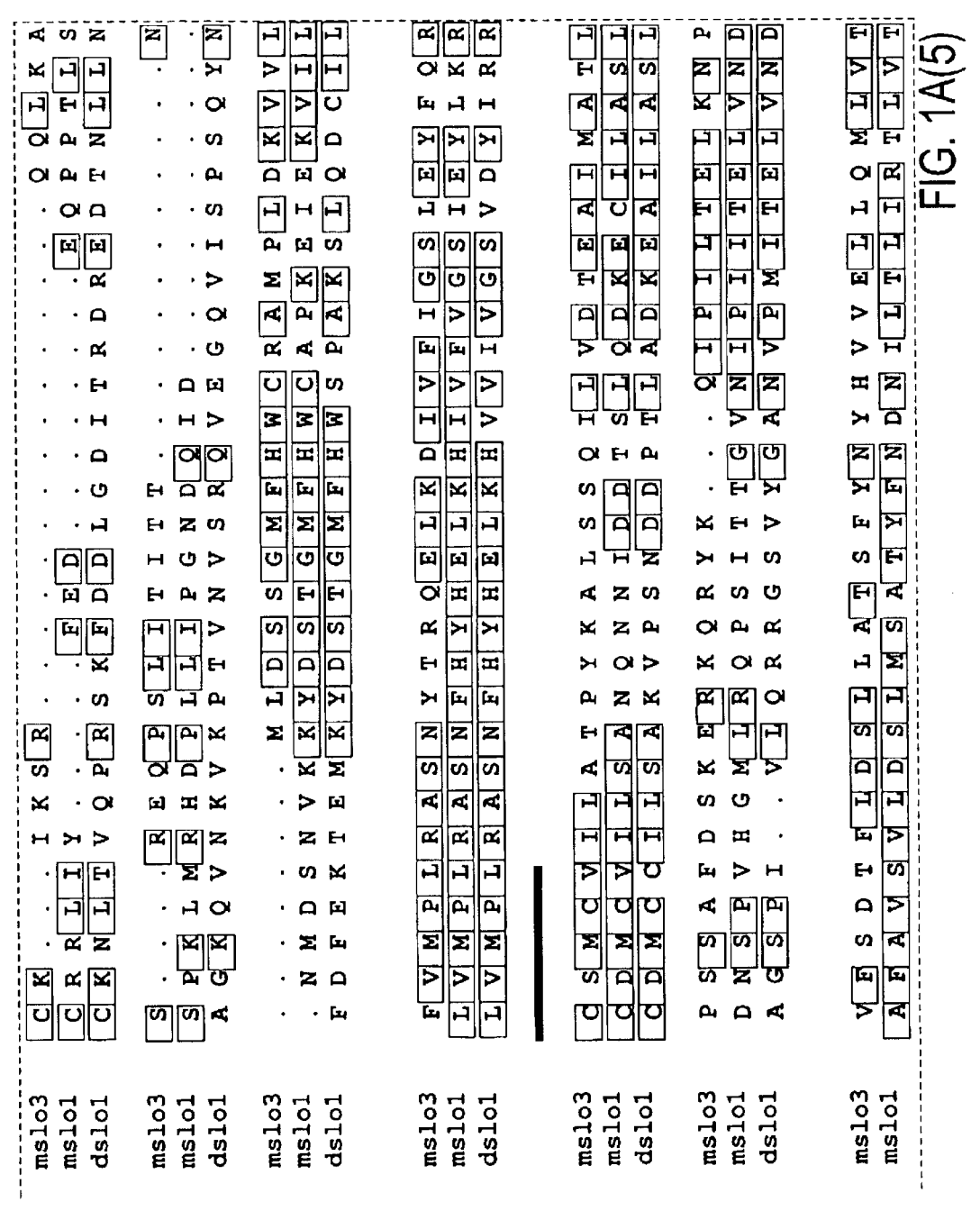
Figure 1A:
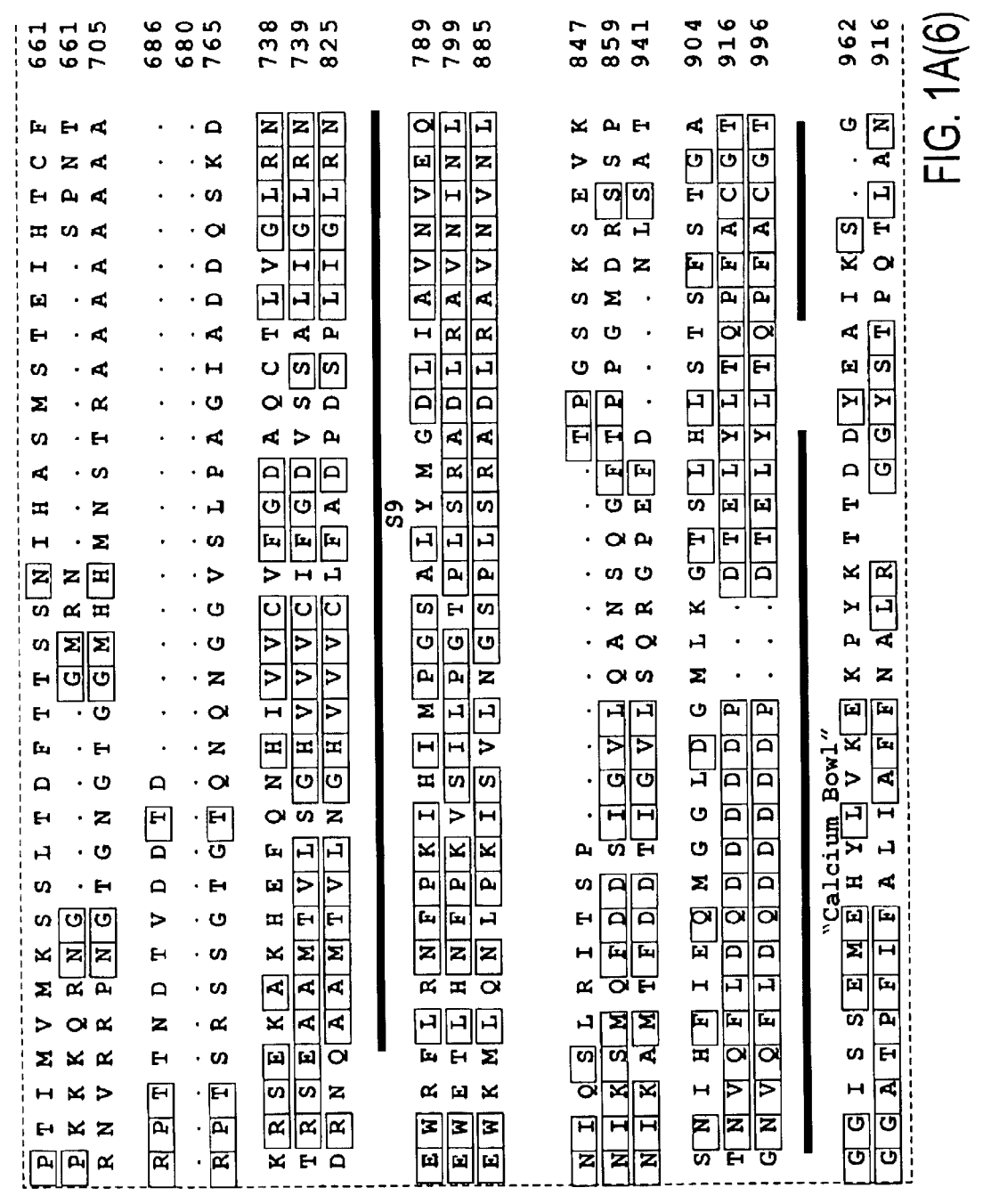
Figure 1A:
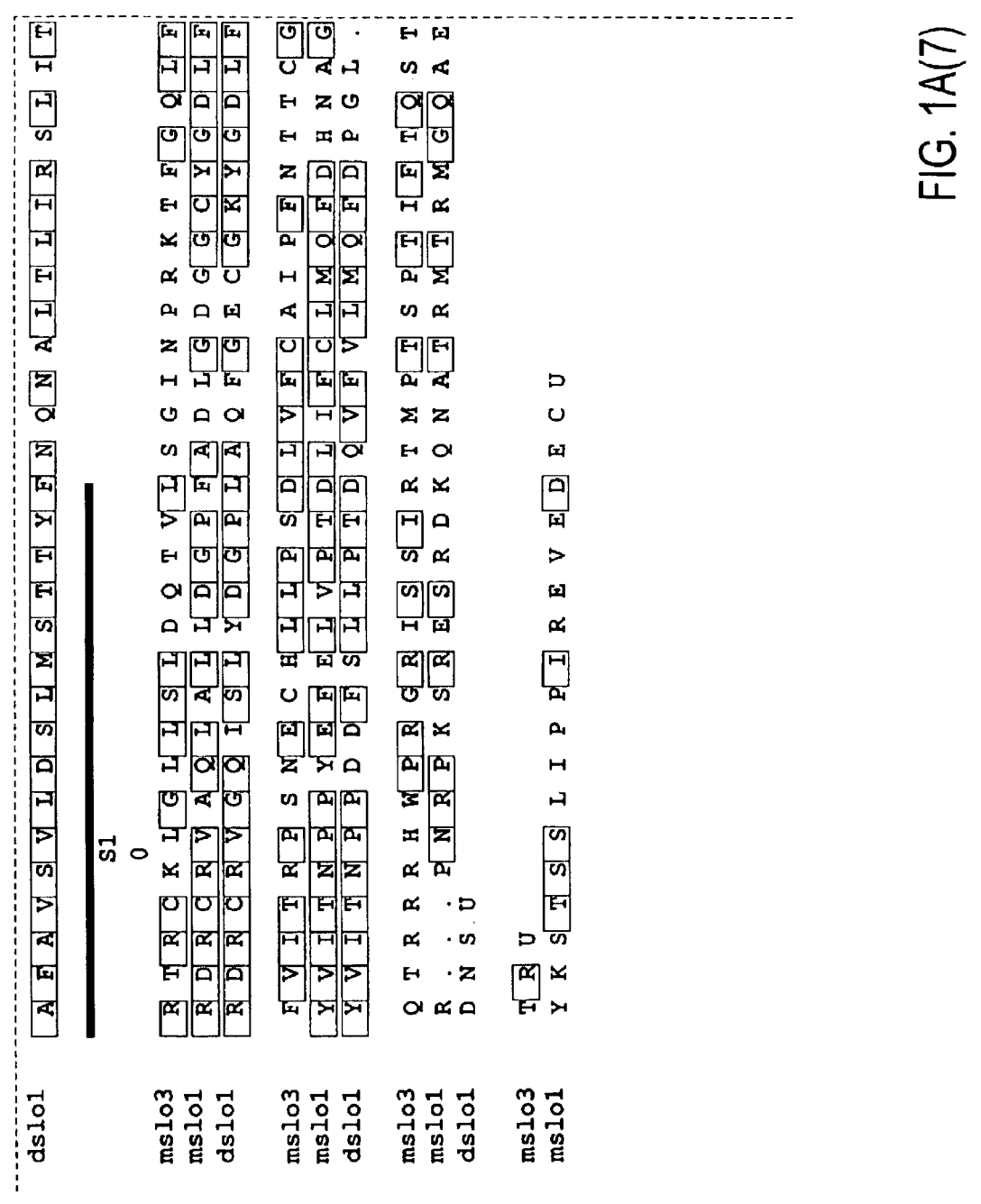
Figure 1A:
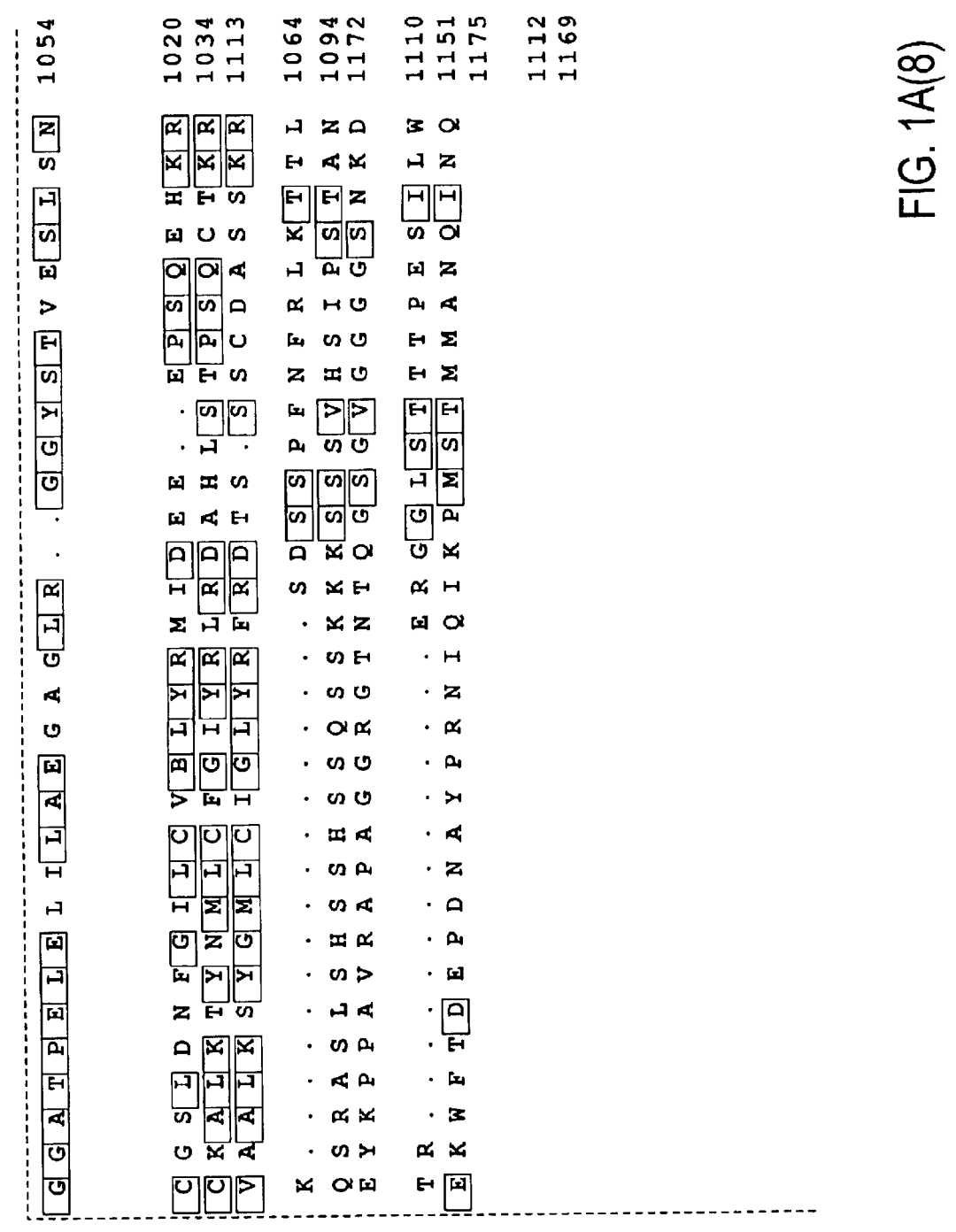
Figure 1B:
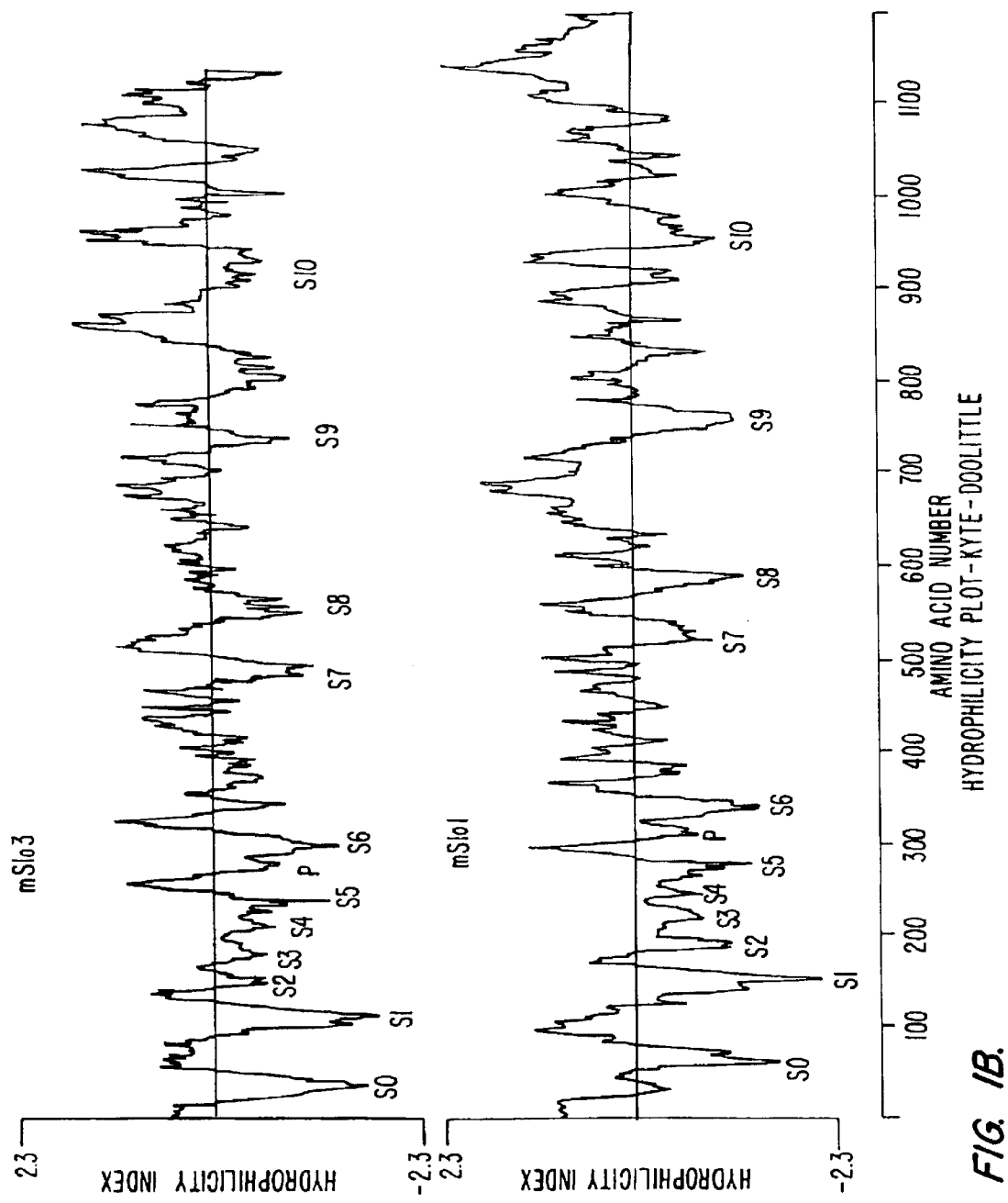
FIG. 1B: Kyte-Doolittle hydrophilicity plots of mSlo3 and mSlo1. The mbr5 mSlo1 (Butler et al., 1992) and splice variant A2C2E2G5I0 dSlo1 (Atkinson et al., Science 253:551–553 (1991); Adelman et al., Neuron 9:209–216 (1992)) sequences are shown. Slo2 is a more distantly related sequence present in the nematode database (Wei et al., Neuropharmacology 35:805–829 (1996).

Structurally, the full length nucleotide sequence of mSlo3 (SEQ ID NO:2) encodes a protein of 1113 amino acids (SEQ ID NO:1) with a predicted molecular mass of 126 kDa. hSlo3 encodes a protein of a similar size and expression pattern (see Example II). Slo3 is a member of the Slo of potassium channel protein family as evidenced by sequence homology to the BK calcium-activated potassium channel (Slo1; see FIGS. 1A(1–8)). The hydrophilicity profiles of Slo1 and Slo3 sequences indicate 11 hydrophobic segments, S0 through S10, which can be divided into "core" and "tail" domains (FIG. 1B). Within the core domain (hydrophobic regions S0–S8 of Slo3 proteins) mSlo3 and the sequenced region of hSlo3 share at least 61.5% amino acid identity, while mSlo1 and mSlo3 share 51% identity in this region. Homology in the core domain is much higher than in the tail domain, which is involved in calcium sensing (Wei et al., *Neuron* 13:671–681 (1994)).

Two notable differences suggest possible functional distinctions between mSlo1 and mSlo3. First, the "Calcium Bowl," a hyperconserved aspartate-rich region involved in calcium sensing, is absent in Slo3 (Schreiber & Salkoff, *Biophys. J.* 73:1355–1363 (1997)). Second, mSlo3 contains GFG rather than GYG in the conserved pore signature sequence involved in $K^+$ ion selectivity (Yool & Schwarz, *Nature* 349:700–704 (1991); Hartmann et al., *Science* 251:942–944 (1991); Heginbotham & MacKinnon, *Biophys. J.* 66:1061–1067 (1994)). This difference shows that ionic selectivity differs between the two channels.

Specific regions of the Slo3 nucleotide and amino acid sequence may be used to identify polymorphic variants, interspecies homologs, and alleles of Slo3. This identification can be made in vitro, e.g., under stringent hybridization conditions and sequencing, or by using the sequence information in a computer system for comparison with other nucleotide sequences. Typically, identification of polymorphic variants and alleles of Slo3 is made by comparing the amino acid sequence of the core domain (amino acids 35–641 of mSlo3, S0 through S8 of Slo3). This domain is also useful for identifying members of the Slo family. For example, potassium channel proteins that share at least 60% or greater amino acid identity in the core domain are Slo3 proteins, while those that share approximately 50% or less homology are members of the Slo family. Another useful region for identifying homologs of Slo3 is the region between S8 and S9. This region is not highly conserved between mSlo1 and mSlo3, and so can be used to identify interspecies homologs of Slo3. Antibodies that bind specifically to the core domain of Slo3 can also be used to identify alleles, interspecies homologs, and polymorphic variants.

Polymorphic variants, interspecies homologs, and alleles of Slo3 are confirmed by expressing the putative Slo3 polypeptide monomer and examining functional characteristics, such as voltage-gating and pH sensitivity. This assay is used to demonstrate that a protein having about 60% or greater, preferably 75–80% or greater amino acid identity to the core domain of Slo3 shares the same functional characteristics as Slo3 and is therefore a species of Slo3. Typically, Slo3 having the amino acid sequence of SEQ ID NO:1 or 3 is used as a positive control in comparison to the putative Slo3 protein to demonstrate the identification of a polymorphic variant, allele, or interspecies homologue of Slo3.

For example, measurements of the cell expression the putative Slo3 are taken to detect induction of ion flux (e.g., by radiotracer), or a change in ionic conductance of the cell (e.g., by patch clamp), or a change in voltage (e.g., by fluorescent dye). If the presence of an ion channel is indicated by a pH induced or voltage-gated change, subsequent tests are used to characterize the channel as a Slo3 channel of the present invention. For example, pH sensitivity can be determined as described above, using inside out patches in saline of different pH. Whole cell recordings in sodium bicarbonate or ammonium chloride can also be used. Compounds such as rotenone and FCCP can be used to acidify the cell, and protonofors can also be used to determine pH sensitivity. Preferably, at least two characteristics are determined, more preferably at least 3, or 4 are determined. Characteristics of Slo3 channels of the present invention are disclosed more fully herein.

The present invention also provide polymorphic variants of the mSlo3 depicted in SEQ ID NO:1: variant #1, in which a valine residue is substituted for an isoleucine residue at amino acid position 21; variant #2, in which an isoleucine residue is substituted for a leucine residue at amino acid position 5; and variant #3, in which a serine residue is substituted for an alanine residue at amino acid position 25.

The present invention also provide polymorphic variants of the hSlo3 depicted in SEQ ID NO:16: variant #1, in which a valine residue is substituted for an isoleucine residue at amino acid position 23; variant #2, in which an isoleucine residue is substituted for a leucine residue at amino acid position 6; and variant #3, in which a serine residue is substituted for an alanine residue at amino acid position 25.

The isolation of Slo3 protein for the first time provides a means for assaying for compounds that increase or decrease the ion channel activity of this pH sensitive potassium channel, which is involved in sperm physiology. Slo3 nucleic acids and proteins are useful for testing inhibitors or activators of Slo3 using in vitro or in vivo assays, e.g., expressing Slo3 in cells or cell membranes and then measuring flux of ions through the channel. Such inhibitors or activators identified using Slo3 can be used therapeutically to treat infertility conditions related to sperm physiology, or as contraceptives. Slo3 expression also provides a convenient diagnostic marker for spermiatocytes. Spermatocytes lacking Slo3 expression may be indicative of sperm that lack the capability of undergoing capacitation or acrosome reactions, which are essential for fertilization. Antibodies or other probes for Slo3 can be also used in vitro as diagnostic tools to examine Slo3 expression. Slo3 can also be used to study sperm physiology in vitro, e.g., the capacitation and acrosome reactions that are essential for sperm activity.

Portions of the Slo3 nucleotide sequence may be used to identify homologs of the channel, as well as variants or mutations of the channel that may be associated with disease. This identification can be made in vitro or by using the sequence information in a computer system for comparison with other nucleotide sequences. Similarly, these portions of Slo3 nucleotide sequence may be used to determine the presence of a Slo3 channel mRNA or channel protein in a particular tissue of interest. Information derived from the Slo3 nucleotide sequence may also be used to identify the chromosomal localization of the Slo3 gene or genes using chromosomal panels, radiation hybrid screening, fluorescent in situ hybridization methods (FISH), or by comparison of the sequence with computer nucleic acid databases. The Slo3 channel or fragments thereof may also be used to treat diseases using gene therapy. A Slo3 nucleotide sequence information may also be used to construct models of the ion channel protein in a computer system, these models subsequently being used to identify compounds that can modulate channel function.

Furthermore, the invention provides assays for Slo3 activity where Slo3 acts as a direct or indirect reporter molecule, e.g., as part of a chimera with another channel protein such as Slo1. Such uses of Slo3 as a reporter molecule in assay and detection systems have broad applications, e.g., Slo3 can be used as a reporter molecule to measure changes in potassium concentration, membrane potential, current flow, ion flux, transcription, signal transduction, receptor-ligand interactions, second messenger concentrations, in vitro, in vivo, and ex vivo. In one embodiment, Slo3 can be used as an indicator of current flow in a particular direction (e.g., outward or inward potassium flow), and in another embodiment, Slo3 can be used as an indirect reporter via attachment to a second reporter molecule such as green fluorescent protein.

II. Definitions

Unless otherwise indicated, nucleic acids are written left to right in 5' to 3' orientation; amino acid sequences are written left to right in amino to carboxy orientation, respectively. Numeric ranges are inclusive of the numbers defining the range. The terms defined below are more fully defined by reference to the specification as a whole.

By "pH sensitive potassium channel" or "Slo3 channel" is meant a membrane channel which is voltage-gated, pH sensitive (e.g., with increased activity as measured by increased current amplitude above about pHi 7.1), and has a unitary conductance of from about 80–120 pS when measured under a symmetrical potassium concentration of 160 mM in a Xenopus oocyte using the conditions specified in Example IV. An Slo3 channel comprises multiple Slo3 channel proteins as subunits, typically four Slo3 channel proteins (e.g., full length or substantially full length Slo3 channel proteins).

A "Slo3 core domain" refers to the amino acids corresponding to the S0–S8 region of a Slo3 polypeptide, e.g., amino acids 35–641 of mSlo3 (SEQ ID NO:1).

By "pH sensitive potassium channel subunit" or "Slo3 channel protein" is meant a polypeptide of a molecular weight of between about 120–156 kDa havin a core domain with at least about 60% identity to the core domain of SEQ ID NO:1, 3, 16 or 18, and having the characteristic of pH sensitivity and/or voltage gating. These proteins serve as monomers of the Slo3 channel. Thus, a Slo3 channel protein can have the functional characteristics to form a heteromeric or homomeric protein with the functional characteristics of an Slo3 channel, or be a peptide fragment thereof. This term refers both to recombinant and naturally occurring forms of Slo3. Both recombinant and naturally occurring Slo3 can be used in the methods of the invention described herein, e.g., in assays to identify inhibitors or activators of Slo3.

The term Slo3 therefore refers to polymorphic variants, alleles, mutants, and interspecies variants of Slo3 that: (1) have greater than 60% amino acid sequence identity to a Slo3 core domain; or (2) bind to antibodies raised against an immunogen comprising an amino acid sequence selected from the group consisting of SEQ ID NO:1, SEQ ID NO:3, SEQ ID NO:16, or SEQ ID NO:18 and conservatively modified variants thereof; or (3) specifically hybridize under stringent hybridization conditions to a sequence selected from the group consisting of SEQ ID NO:2, SEQ ID NO:17, SEQ ID NO:19 and conservatively modified variants thereof; or (4) are amplified by primers that specifically hybridize under stringent ,bridization conditions to the same sequence as a primer set consisting of SEQ ID NOS:8 and 9, 10 and 11, 12 and 13 or 14 and 15.

"pH sensitive" refers to a characteristic of Slo3 channels, where the channels have increased current amplitude in response to changes in intracellular pH (pHi). Typically, pH sensitive channels show increased current amplitude above approximately pHi 7.1. For example, mSlo3 at a pHi of 6.8 did not show increased activity, while activity was substantially increased at pHi 7.8. pH sensitivity can be measure using a number of assays. For example, single channel recordings are made from inside out patches that have been perfused with saline of different pHs and the open probability of the channel vs. the pH is plotted to determine pH sensitivity. In another example, macroscopic current is examined with an inside out patch perfused with saline of varying pHs, and the amplitude of the current is measured. In another example, a whole cell recording is made with a two electrode voltage clamp, where the cell is in sodium bicarbonate solution (lowers intracellular pH) or ammonium chloride solution (raises intracellular pH).

The phrase "voltage-gated" activity or "voltage-gating" refers a characteristic of a potassium channel composed of individual polypeptide monomers or subunits. Generally, the probability of a voltage-gated potassium channel opening increases as a cell is depolarized. Voltage-gated potassium channels primarily allow efflux of potassium because they have greater probabilities of being open at membrane potentials more positive than the equilibrium potential for potassium (EK) in typical cells. EK is the combination of the voltage potential and [K$^+$] potential at which there is no net flow of potassium ion. This value, also known as the "reversal potential" or the "Nernst" potential for potassium, depends on the relative concentrations of potassium found inside and outside the membrane, and is typically between −60 and −100 mV for mammalian cells. Some voltage-gated potassium channels undergo inactivation, which can reduce potassium efflux at higher membrane potentials. These channels can also allow potassium influx in certain instances when they remain open at membrane potentials negative to EK (see, e.g., Adams & Nonner, in *Potassium Channels*, pp. 40–60 (Cook, ed., 1990)).

Typically, the channel is composed of four subunits and the channel can be heteromeric or homomeric. "Homomeric" refers to a potassium channel composed of the same type of subunit, while "heteromeric" refers to a potassium channel composed of two or more different types of subunits. Voltage-gated potassium channels composed of Slo are typically homomeric, having four Slo subunits. The characteristic of voltage gating can be measured by a variety of techniques for measuring changes in current flow and ion flux through a channel, e.g., by changing the [K$^+$] of the external solution and measuring the activation potential of the channel current (see, e.g., U.S. Pat. No. 5,670,335), by measuring current with patch clamp techniques or voltage clamp under different conditions, and by measuring ion flux with radiolabeled tracers or voltage-sensitive dyes under different conditions.

The terms "isolated" "purified" or "biologically pure" refer to material that is substantially or essentially free from components which normally accompany it as found in its native state. Purity and homogeneity are typically determined using analytical chemistry techniques such as polyacrylamide gel electrophoresis or high performance liquid chromatography. A protein that is the predominant species present in a preparation is substantially purified. In particular, an isolated Slo3 nucleic acid is separated from open reading frames which flank the Slo3 gene and encode proteins other than Slo3. The term "purified" denotes that a nucleic acid or protein gives rise to essentially one band in an electrophoretic gel. Particularly, it means that the nucleic acid or protein is at least 85% pure, more preferably at least 95% pure, and most preferably at least 99% pure.

The term "subsequence" in the context of a referenced nucleic acid sequence includes reference to a contiguous sequence from the nucleic acid having fewer nucleotides in length than the referenced nucleic acid. In the context of a referenced protein, polypeptide, or peptide sequence, "subsequence" refers to a contiguous sequence from the referenced protein having fewer amino acids than the referenced protein.

The term "heterologous" when used with reference to portions of a nucleic acid indicates that the nucleic acid comprises two or more subsequences which are not found in the same relationship to each other in nature. For instance, the nucleic acid is typically recombinantly produced, having two or more sequences from unrelated genes arranged to make a new functional nucleic acid.

"Nucleic acid" refers to deoxyribonucleotides or ribonucleotides and polymers thereof in either single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs).

Unless otherwise indicated, a particular nucleic acid sequence also implicitly encompasses conservatively modified variants thereof (e.g., degenerate codon substitutions, as described below) and complementary sequences, as well as the sequence explicitly indicated. The term nucleic acid is used interchangeably with gene, cDNA, mRNA, oligonucleotide, and polynucleotide.

The terms "polypeptide," "peptide" and "protein" are used interchangeably herein to refer to a polymer of amino acid residues. The terms apply to amino acid polymers in which one or more amino acid residue is an analog or mimetic of a corresponding naturally occurring amino acid, as well as to naturally occurring amino acid polymers.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605–2608 (1985); Rossolini et al., *Mol. Cell. Probes* 8:91–98 (1994)). Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following groups each contain amino acids that are conservative substitutions for one another:

1) Alanine (A), Glycine (G);
2) Serine (S), Threonine (T);
3) Aspartic acid (D), Glutamic acid (E);
4) Asparagine (N), Glutamine (Q);
5) Cysteine (C), Methionine (M);
6) Arginine (R), Lysine (K), Histidine (H);
7) Isoleucine (I), Leucine (L), Valine (V); and
8) Phenylalanine (F), Tyrosine (Y), Tryptophan (W). (see, e.g., Creighton, *Proteins* (1984)).

A "label" is a composition detectable by spectroscopic, photochemical, biochemical, immunochemical, or chemical means. For example, useful labels include 32P, fluorescent dyes, electron-dense reagents, enzymes (e.g., as commonly used in an ELISA), biotin, dioxigenin, or haptens and proteins for which antisera or monoclonal antibodies are available (e.g., the peptide of SEQ ID NO:1 can be made detectable, e.g., by incorporating a radio-label into the peptide, and used to detect antibodies specifically reactive with the peptide).

As used herein a "probe or primer" is defined as a nucleic acid capable of binding to a target nucleic acid of complementary sequence through one or more types of chemical bonds, usually through complementary base pairing, usually through hydrogen bond formation. It will be understood by one of skill in the art that probes may bind target sequences lacking complete complementarity with the probe sequence depending upon the stringency of the hybridization conditions. The probes are preferably directly labeled as with isotopes, chromophores, lumiphores, chromogens, or indirectly labeled such as with biotin to which a streptavidin complex may later bind. By assaying for the presence or absence of the probe, one can detect the presence or absence of the select sequence or subsequence.

A "labeled nucleic acid probe or oligonucleotide" is one that is bound, either covalently, through a linker, or through ionic, van der Waals or hydrogen bonds to a label such that the presence of the probe may be detected by detecting the presence of the label bound to the probe.

"Amplification" primers are oligonucleotides comprising either natural or analog nucleotides that can serve as the basis for the amplification of a select nucleic acid sequence. They include, e.g., polymerase chain reaction primers and ligase chain reaction oligonucleotides. Amplification primers are used to "amplify" a target nucleic acid sequence.

The term "recombinant" when used with reference to a cell, or protein, nucleic acid, or vector, includes reference to a cell, protein, or nucleic acid, or vector, that has been modified by the introduction of a heterologous nucleic acid or the alteration of a native nucleic acid to a form not native to that cell, or that the cell is derived from a cell so modified. Thus, for example, recombinant cells express genes and proteins that are not found within the native (non-recombinant) form of the cell or express native genes that are otherwise abnormally expressed, under expressed or not expressed at all.

An "expression vector" is a nucleic acid construct, generated recombinantly or synthetically, with a series of specified nucleic acid elements which permit transcription of a particular nucleic acid in a host cell. The expression vector can be part of a plasmid, virus, or nucleic acid fragment. Typically, the expression vector includes a nucleic acid to be transcribed operably linked to a promoter.

The terms "identical" or percent "identity," in the context of two or more nucleic acids or polypeptide sequences, refer to two or more sequences or subsequences that are the same or have a specified percentage of amino acid residues or nucleotides that are the same, when compared and aligned for maximum correspondence over a comparison window, as measured using one of the following sequence comparison algorithms or by manual alignment and visual inspection. This definition also refers to the complement of a test sequence, which has a designated percent sequence or subsequence complementarity when the test sequence has a designated or substantial identity to a reference sequence. Preferably, the amino acid or nucleotide sequence identity is at least about 60%, more preferably at least about 75–80%, more preferably about 90–95%. For example, a designated amino acid percent identity of 60% refers to sequences or subsequences that have at least about 60% amino acid identity when aligned for maximum correspondence over a comparison window as measured using one of the following sequence comparison algorithms or by manual alignment and visual inspection. Preferably, the percent identity exists over a region of the sequence that is at least about 25 amino acids in length, more preferably over a region that is 50–100 amino acids in length.

When percentage of sequence identity is used in reference to proteins or peptides, it is recognized that residue positions that are not identical often differ by conservative amino acid substitutions, where amino acids residues are substituted for other amino acid residues with similar chemical properties (e.g., charge or hydrophobicity) and therefore do not change the functional properties of the molecule. Where sequences differ in conservative substitutions, the percent sequence identity may be adjusted upwards to correct for the conservative nature of the substitution. Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated according to, e.g., the algorithm of Meyers & Miller, *Computer Applic. Biol. Sci.* 4:11–17 (1988) e.g., as implemented in the program PC/GENE (Intelligenetics, Mountain. View, Calif., USA).

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identity for the test sequence(s) relative to the reference sequence, based on the designated or default program parameters.

A "comparison window", as used herein, includes reference to a segment of any one of the number of contiguous positions selected from the group consisting of from 25 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Ausubel et al., supra).

One example of a useful algorithm is PILEUP. PILEUP creates a multiple sequence alignment from a group of related sequences using progressive, pairwise alignments to show relationship and percent sequence identity. It also plots a tree or dendogram showing the clustering relationships used to create the alignment. PILEUP uses a simplification of the progressive alignment method of Feng & Doolittle, *J. Mol. Evol.* 35:351–360 (1987). The method used is similar to the method described by Higgins & Sharp, *CABIOS* 5:151–153 (1989). The program can align up to 300 sequences, each of a maximum length of 5,000 nucleotides or amino acids. The multiple alignment procedure begins with the pairwise alignment of the two most similar sequences, producing a cluster of two aligned sequences. This cluster is then aligned to the next most related sequence or cluster of aligned sequences. Two clusters of sequences are aligned by a simple extension of the pairwise alignment of two individual sequences. The final alignment is achieved by a series of progressive, pairwise alignments. The program is run by designating specific sequences and their amino acid or nucleotide coordinates for regions of sequence comparison and by designating the program parameters. Using PILEUP, a reference sequence is compared to other test sequences to determine the percent sequence identity relationship using the following parameters: default gap weight (3.00), default gap length weight (0.10), and weighted end gaps. PILEUP can be obtained from the GCG sequence analysis software package, e.g., version 7.0 (Devereaux et al., *Nuc. Acids Res.* 12:387–395 (1984).

Another example of algorithm that is suitable for determining percent sequence identity (i.e., substantial similarity or identity) is the BLAST algorithm, which is described in Altschul et al., *J. Mol. Biol.* 215:403–410 (1990). Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues, always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=4, and a comparison of both strands. For amino acid sequences, the BLASTP program uses as default parameters a wordlength (W) of 3, an expectation (E) of 10, and the BLOSUM62 scoring matrix (see Henikoff & Henikoff, *Proc. Natl. Acad. Sci. USA* 89:10915 (1989)).

The BLAST algorithm also performs a statistical analysis of the similarity between two sequences (see, e.g., Karlin & Altschul, *Proc. Nat'l. Acad. Sci. USA* 90:5873–5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

An indication that two nucleic acid sequences or polypeptides are substantially identical, i.e., they have a designated percent identity, is that the polypeptide encoded by the first nucleic acid is immunologically cross reactive with the antibodies raised against the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below. A further indication that two polynucleotides are substantially identical is if the reference sequence, amplified by a pair of oligonucleotide primers or a pool of degenerate primers that encode a conserved amino acid sequence, can then be used as a probe under stringent hybridization conditions to isolate the test sequence from a cDNA or genomic library, or to identify the test sequence in, e.g., a northern or Southern blot. Alternatively, another indication that the sequences are substantially identical is if the same set of PCR primers can be used to amplify both sequences.

The phrase "selectively (or specifically) hybridizes to" refers to the binding, duplexing, or hybridizing of a molecule to a particular nucleotide sequence under stringent hybridization conditions when that sequence is present in a complex mixture (e.g., total cellular or library DNA or RNA), wherein the particular nucleotide sequence is detected at least at twice background, preferably 10 times background.

The phrase "stringent hybridization conditions" refers to conditions under which a probe will hybridize to its target subsequence, typically in a complex mixture of nucleic acid, but to no other sequences. Stringent conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology—Hybridization with Nucleic Probes*, "Overview of principles of hybridization and the strategy of nucleic acid assays" (1993). Generally, stringent conditions are selected to be about 5–10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. For selective or specific hybridization, a positive signal is at least two times background, preferably 10 time background hybridization. Exemplary "highly stringent" hybridization conditions include hybridization in a buffer comprising 50% formamide, 5×SSC, and 1% SDS at 42° C., or hybridization in a buffer comprising 5×SSC and 1% SDS at 65° C., both with a wash of 0.2×SSC and 0.1% SDS at 65° C.

Exemplary "moderately stringent hybridization conditions" include a hybridization in a buffer of 40% formamide, 1 M NaCl, and 1% SDS at 37° C., and a wash in 1×SSC at 45° C. A positive hybridization is at least twice background. Those of ordinary skill will readily recognize that alternative hybridization and wash conditions can be utilized to provide conditions of similar stringency. Nucleic acids which do not hybridize to each other under moderately stringent or stringent hybridization conditions are still substantially identical if the polypeptides which they encode are substantially identical. This may occur, e.g., when a copy of a nucleic acid is created using the maximum codon degeneracy permitted by the genetic code.

The phrase "encodes a protein which could be encoded by a nucleic acid that selectively hybridizes under moderate stringency hybridization conditions to a sequence" in the context of nucleic acids refers to those nucleic acids encoding naturally occurring proteins or derivatives of natural proteins, but which are deliberately modified or engineered to no longer hybridize to the protein of natural origin under the stated conditions.

The term "antibody" also includes antigen binding forms of antibodies (e.g., Fab, F(ab)2). The term "antibody" refers to a polypeptide substantially encoded by an immunoglobulin gene or immunoglobulin genes, or fragments thereof which specifically bind and recognize an antigen. The recognized immunoglobulin genes include the kappa, lambda, alpha, gamma, delta, epsilon and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

An exemplary immunoglobulin (antibody) structural unit comprises a tetramer. Each tetramer is composed of two identical pairs of polypeptide chains, each pair having one "light" (about 25 kD) and one "heavy" chain (about 50–70 kD). The N-terminus of each chain defines a variable region of about 100 to 110 or more amino acids primarily responsible for antigen recognition. The terms variable light chain (VL) and variable heavy chain (VH) refer to these light and heavy chains respectively.

Antibodies exist e.g., as intact immunoglobulins or as a number of well characterized fragments produced by digestion with various peptidases. Thus, for example, pepsin digests an antibody below the disulfide linkages in the hinge region to produce F(ab)'2, a dimer of Fab which itself is a light chain joined to VH-CH1 by a disulfide bond. The F(ab)'2 may be reduced under mild conditions to break the disulfide linkage in the hinge region, thereby converting the F(ab)'2 dimer into an Fab' monomer. The Fab' monomer is essentially an Fab with part of the hinge region (see, e.g., *Fundamental Immunology* (Paul ed., 3d ed. 1993). While various antibody fragments are defined in terms of the digestion of an intact antibody, one of skill will appreciate that such fragments may be synthesized de novo either chemically or by utilizing recombinant DNA methodology. Thus, the term antibody, as used herein, also includes antibody fragments such as single chain Fv, chimeric antibodies (i.e., comprising constant and variable regions from different species), humanized antibodies (i.e., comprising a complementarity determining region (CDR) from a non-human source) and heteroconjugate antibodies (e.g., bispecific antibodies).

An "anti-Slo3" antibody is an antibody or antibody fragment that specifically binds a polypeptide encoded by a Slo3 gene, cDNA, or a subsequence thereof. The antibody can be either a monoclonal or polyclonal antibody.

A "chimeric antibody" is an antibody molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region having a different or altered antigen specificity.

The term "immunoassay" is an assay that uses an antibody to specifically bind an antigen. The immunoassay is characterized by the use of specific binding properties of a particular antibody to isolate, target, and/or quantify the antigen.

The phrase "specifically (or selectively) binds to an antibody" or "specifically (or selectively) immunoreactive with," when referring to a protein or peptide, refers to a binding reaction that is determinative of the presence of the protein in a heterogeneous population of proteins and other biologics. Thus, under designated immunoassay conditions, the specified antibodies bind to a particular protein and do not bind in a significant amount to other proteins present in the sample. Specific binding to an antibody under such conditions may require an antibody that is selected for its specificity for a particular protein.

For example, antibodies raised to mSlo3 or hSlo3 with the amino acid sequence encoded in SEQ ID NO:1, SEQ ID NO:3, SEQ ID NO:16, and SEQ ID NO:18 respectively, can be selected to obtain polyclonal antibodies specifically immunoreactive with that protein and not with other proteins, except for polymorphic variants and alleles. This selection may be achieved by subtracting out antibodies that cross-react with Slo3 molecules from other species. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, *Antibodies, A Laboratory Manual* (1988), for a description of immunoassay formats and conditions that can be used to determine specific immunoreactivity). Typically a specific or selective reaction will be at least twice background signal or noise and more typically more than 10 to 100 times background.

The phrase "selectively associates with" refers to the ability of a nucleic acid to "selectively hybridize" with another as defined above, or the ability of an antibody to "selectively (or specifically) bind to a protein, as defined above.

The phrase "functional effects" in the context of assays for testing compounds affecting the channel includes the determination of any parameter that is indirectly or directly under the influence of the channel. It includes changes in ion flux, membrane potential, voltage gating, and pH sensitivity and also includes other physiologic effects such increases or decreases of transcription or hormone release.

By "determining the functional effect" is meant examining the effect of a compound that increases or decreases ion flux on a cell or cell membrane in terms of cell and cell membrane function. The ion flux can be any ion that passes through the channel and analogs thereof, e.g., potassium, rubidium, sodium, and radioisotopes thereof. Preferably, the term refers to the functional effect of the compound on Slo3 channel activity, e.g., changes in ion flux, current amplitude, voltage gating, pH sensitivity, and the like. Such functional effects can be measured by any means known to those skilled in the art, e.g., patch clamping, whole cell currents, pH and voltage sensitive dyes, radioisotope efflux, inducible markers, and the like.

"Inhibitors," "activators," and "modulators" of Slo3 refer to inhibitory or activating molecules identified using in vitro assays for Slo3 function. Inhibitors are compounds that decrease, block, prevent, delay activation, inactivate, desensitize, or down regulate the channel. Activators are compounds that increase, open, activate, facilitate, enhance activation, sensitize or up regulate channel activity. Such assays for inhibitors and activators include e.g., expressing Slo in cells or cell membranes and then measuring flux of ions through the channel and determining changes in polarization (i.e., electrical potential). Methods of measuring changes of cell membrane polarization and ion flux include voltage-clamp techniques, determination of whole cell currents, radiolabeled rubidium flux assays, and fluorescence assays using voltage-sensitive dyes. Samples or assays that are treated with a potential Slo3 activator or inhibitor are compared to control samples without the inhibitor, to examine the extent of inhibition. Control samples (untreated with inhibitors) are assigned a relative Slo3 activity value of 100. Inhibition of Slo3 is achieved when the Slo3 activity value relative to the control is about 90%, preferably 50%, more preferably 25%. Activation of Slo3 is achieved when the Slo3 activity value relative to the control is 110%, more preferably 150%, more preferable 200% higher.

By "host cell" is meant a cell which contains an expression vector and supports the replication or expression of the expression vector. Host cells may be prokaryotic cells such as *E. coli*, or eukaryotic cells such as yeast; insect, amphibian, e.g., Xenopus, or mammalian cells such as CHO, HeLa and the like. The Slo3 channel can also be expressed in a cell membrane derived from such a cell.

"Biological sample" as used herein is a sample of biological tissue or fluid that contains a Slo3 channel protein or nucleic acid encoding the corresponding Slo3 channel protein. Such samples include, but are not limited to, seminal fluid containing sperm, sperm cells, testis tissue, and brain tissue. Biological samples may also include sections of tissues such as frozen sections taken for histological purposes. A biological sample is typically obtained from a eukaryotic organism, preferably a multicellular eukaryotes such as insect, protozoa, birds, fish, reptiles, and preferably a mammal such as rat, mice, cow, dog, guinea pig, or rabbit, and most preferably a primate such as macaques, chimpanzees, or humans.

By "conductance" is meant electrical conductance. Electrical conductance is conveniently measured in Siemens (1/ohm=mho). Unitary conductance is determined by measuring single channel currents using a patch clamp protocol under conditions set forth in Examples III and IV (i.e., in a Xenopus oocyte) using a symmetrical potassium ion concentration of 160 mM (see generally, Hille, *Ionic Channels of Excitable Membranes* (2d ed.) In the context of the present invention, "conductance" refers to the unitary electrical conductance of a single homomeric protein of the referenced Slo3 channel protein.

"Functional tetrameric form" refers to expression of a Slo3 protein or monomer in which a plurality of the Slo3 proteins are assembled to form, by themselves or in conjunction with other endogenous Xenopus oocyte molecules, an Slo3 potassium channel. Expression within a Xenopus oocyte is disclosed in the Examples provided herein, e.g., Example III. Typically the Slo3 channel is a homotetramer formed of four Slo3 monomer proteins.

By "contiguous amino acids from" in the context of a specified number of amino acid residues from a specified sequence, is meant a sequence of amino acids of the specified number from within the specified reference sequence which has the identical order of amino acids each of which is directly adjacent to the same amino acids as in the reference sequence.

III. Nucleic acids encoding Slo3

The present invention provides isolated nucleic acids of RNA, DNA, or chimeras thereof, which encode Slo3 channel proteins. Nucleic acids of the present invention can be used as probes, for example, in detecting deficiencies in the level of mRNA, mutations in the gene (e.g., substitutions, deletions, or additions), for monitoring up regulation of Slo3 channels in drug screening assays, or for recombinant expression of Slo3 channel proteins for use as inmmunogens in the preparation of antibodies or for in vitro or in vivo expression assays.

A. General Recombinant DNA Methods

This invention relies on routine techniques in the field of recombinant genetics. Basic texts disclosing the general methods of use in this invention include Sambrook et al., *Molecular Cloning, A Laboratory Manual* (2nd ed. 1989); Kriegler, *Gene Transfer and Expression: A Laboratory Manual* (1990); and *Current Protocols in Molecular Biology* (Ausubel et al., eds., 1994)).

For nucleic acids, sizes are given in either kilobases (kb) or base pairs (bp). These are estimates derived from agarose or acrylamide gel electrophoresis, from sequenced nucleic acids, or from published DNA sequences. For proteins, sizes are given in kilodaltons (kDa) or amino acid residue numbers. Proteins sizes are estimated from gel electrophoresis, from sequenced proteins, from derived amino acid sequences, or from published protein sequences.

Oligonucleotides that are not commercially available can be chemically synthesized according to the solid phase phosphoramidite triester method first described by Beaucage & Caruthers, *Tetrahedron Letts.* 22:1859–1862 (1981), using an automated synthesizer, as described in Van Devanter et. al., *Nucleic Acids Res.* 12:6159–6168 (1984). Purification of oligonucleotides is by either native acrylamide gel electrophoresis or by anion-exchange HPLC as described in Pearson & Reanier, *J. Chrom.* 255:137–149 (1983).

The sequence of the cloned genes and synthetic oligonucleotides can be verified after cloning using, e.g., the chain termination method for sequencing double-stranded templates of Wallace et al., *Gene* 16:21–26 (1981).

B. Cloning Methods for the Isolation of Nucleotide Sequences Encoding Slo3

In general, the nucleic acid sequences encoding Slo3 and related nucleic acid sequence homologs are cloned from cDNA and genomic DNA libraries or isolated using amplification techniques with oligonucleotide primers. For example, Slo3 sequences are typically isolated from human nucleic acid (genomic or cDNA) libraries by hybridizing with a nucleic acid probe, the sequence of which can be derived from SEQ ID NO:2, 4, 17, or 19, preferably from the core domain. A suitable tissue from which Slo3 RNA and cDNA can be isolated is testis.

Amplification techniques using primers can also be used to amplify and isolate Slo3 from DNA or RNA. For example, nucleic acids encoding a mSlo3 channel protein of SEQ ID NO:1 may be obtained by amplification of a mouse testis cDNA library or reverse transcribed from mouse testis RNA using isolated nucleic acid primer pairs having the sequence:

CTCGAACTCCCTAAAATCTTACAGAT (SEQ ID NO:8) and
TTCCGTTGAGCCAGGGGTCACCAGAATT (SEQ ID NO:9);
TCTGCTTTGTGAAGCTAAATCT (SEQ ID NO:10) and
TTTCAAAGCCTCTTTAGCGGTAA (SEQ ID NO:11); or
TTATGCCTGGATCTGCACTCTACATG (SEQ ID NO:12) and
ATAGTTTCCGTCTACTACCGAAA (SEQ ID NO:13).

Nucleic acids encoding an hSlo3 channel protein may also be obtained by amplification of a human testis cDNA library or reverse transcribed human testis RNA, using the following primers:

GGCAGCGCTCATTCTTTCCTCCTT (SEQ ID NO:14) and
TGCCCAAAACCTCAACCCAAAATA (SEQ ID NO:15).

These primers can be used, e.g., to amplify either the full length sequence or a probe of one to several hundred nucleotides, which is then used to screen a human library for full-length Slo3. Nucleic acids encoding Slo3 can also be isolated from expression libraries using antibodies as probes. Such polyclonal or monoclonal antibodies can be raised using the sequence of SEQ ID NO:1, 3, 16, or 18.

Slo3 polymorphic variants, alleles, and interspecies homologs that are substantially identical to the core domain of Slo3 can be isolated using Slo3 nucleic acid probes and oligonucleotides under stringent hybridization conditions, by screening libraries. Alternatively, expression libraries can be used to clone Slo3 polymorphic variants, alleles, and interspecies homologs, by detecting expressed homologs immunologically with antisera or purified antibodies made against the core domain of Slo3, which also recognize and selectively bind to the Slo3 homolog.

To make a cDNA library, one should choose a source that is rich in Slo3 mRNA, e.g., testis tissue. The mRNA is then made into cDNA using reverse transcriptase, ligated into a recombinant vector, and transfected into a recombinant host for propagation, screening and cloning. Methods for making and screening cDNA libraries are well known (see, e.g., Gubler & Hoffnan, *Gene* 25:263–269 (1983); Sambrook et al., supra; Ausubel et al., supra).

For a genomic library, the DNA is extracted from the tissue and either mechanically sheared or enzymatically digested to yield fragments of about 12–20 kb. The fragments are then separated by gradient centrifugation from undesired sizes and are constructed in bacteriophage lambda vectors. These vectors and phage are packaged in vitro. Recombinant phage are analyzed by plaque hybridization as described in Benton & Davis, *Science* 196:180–182 (1977). Colony hybridization is carried out as generally described in Grunstein et al., *Proc. Natl. Acad. Sci. USA.*, 72:3961–3965 (1975).

An alternative method of isolating Slo3 nucleic acid and its homologs combines the use of synthetic oligonucleotide primers and amplification of an RNA or DNA template (see U.S. Pat. Nos. 4,683,195 and 4,683,202; PCR Protocols: A Guide to Methods and Applications (Innis et al., eds, 1990)). Methods such as polymerase chain reaction (PCR) and ligase chain reaction (LCR) can be used to amplify nucleic acid sequences of Slo3 directly from mRNA, from cDNA, from genomic libraries or cDNA libraries. Degenerate oligonucleotides can be designed to amplify Slo3 homologs using the sequences provided herein. Restriction endonuclease sites can be incorporated into the primers. Polymerase chain reaction or other in vitro amplification methods may also be useful, for example, to clone nucleic acid sequences that code for proteins to be expressed, to make nucleic acids to use as probes for detecting the presence of Slo3 encoding mRNA in physiological samples, for nucleic acid sequencing, or for other purposes. Genes amplified by the PCR reaction can be purified from agarose gels and cloned into an appropriate vector.

Gene expression of Slo3 can also be analyzed by techniques known in the art, e.g., reverse transcription and amplification of mRNA, isolation of total RNA or poly A+ RNA, northern blotting, dot blotting, in situ hybridization, RNase protection, probing DNA microchip arrays, and the like.

Synthetic oligonucleotides can be used to construct recombinant Slo3 genes for use as probes or for expression of protein. This method is performed using a series of overlapping oligonucleotides usually 40–120 bp in length, representing both the sense and non-sense strands of the gene. These DNA fragments are then annealed, ligated and cloned. Alternatively, amplification techniques can be used with precise primers to amplify a specific subsequence of the Slo3 gene. The specific subsequence is then ligated into an expression vector. As described below in Example VI, Slo3 chimeras can be made, which combine, e.g., either the core or the tail domain of Slo3 with another domain of a heterologous potassium channel protein to create a chimeric, functional potassium channel subunit.

The gene for Slo3 is typically cloned into intermediate vectors before transformation into prokaryotic or eukaryotic cells for replication and/or expression. These intermediate vectors are typically prokaryote vectors, e.g., plasmids, or shuttle vectors. Isolated nucleic acids encoding Slo3 channel proteins comprise a nucleic acid sequence encoding a Slo3 channel protein selected from the group consisting of SEQ ID NO:1, 3, 16, and 18 and subsequences, interspecies homologs, alleles and polymorphic variants thereof In preferred embodiments, the isolated nucleic acid encoding a Slo3 channel protein is selected from the group consisting of: SEQ ID NO:2, 4, 17, and 19, and subsequences thereof.

C. Expression in Prokaryotes and Eukaryotes

To obtain high level expression of a cloned gene, such as those cDNAs encoding Slo3, one typically subclones Slo3 into an expression vector that contains a strong promoter to direct transcription, a transcription/translation terminator, and if for a nucleic acid encoding a protein, a ribosome binding site for translational initiation. Suitable bacterial promoters are well known in the art and described, e.g., in Sambrook et al. and Ausubel et al. Bacterial expression systems for expressing the Slo3 protein are available in, e.g., *E. coli*, Bacillus sp., and Salmonella (Palva et al., *Gene* 22:229–235 (1983); Mosbach et al., *Nature* 302:543–545 (1983). Kits for such expression systems are commercially available. Eukaryotic expression systems for mammalian cells, yeast, and insect cells are well known in the art and are also commercially available.

The promoter used to direct expression of a heterologous nucleic acid depends on the particular application. The promoter is preferably positioned about the same distance from the heterologous transcription start site as it is from the transcription start site in its natural setting. As is known in the art, however, some variation in this distance can be accommodated without loss of promoter function.

In addition to the promoter, the expression vector typically contains a transcription unit or expression cassette that contains all the additional elements required for the expression of the Slo3 encoding nucleic acid in host cells. A typical expression cassette thus contains a promoter operably linked to the nucleic acid sequence encoding Slo3 and signals required for efficient polyadenylation of the transcript, ribosome binding sites, and translation termination. The nucleic acid sequence encoding Slo3 may typically be linked to a cleavable signal peptide sequence to promote secretion of the encoded protein by the transformed cell. Such signal peptides would include, among others, the signal peptides from tissue plasminogen activator, insulin, and neuron growth factor, and juvenile hormone esterase of *Heliothis virescens*. Additional elements of the cassette may include enhancers and, if genomic DNA is used as the structural gene, introns with functional splice donor and acceptor sites.

In addition to a promoter sequence, the expression cassette should also contain a transcription termination region downstream of the structural gene to provide for efficient termination. The termination region may be obtained from the same gene as the promoter sequence or may be obtained from different genes.

The particular expression vector used to transport the genetic information into the cell is not particularly critical. Any of the conventional vectors used for expression in eukaryotic or prokaryotic cells may be used. Standard bacterial expression vectors include plasmids such as pBR322 based plasmids, pSKF, pET23D, and fusion expression systems such as GST and LacZ. Epitope tags can also be added to recombinant proteins to provide convenient methods of isolation, e.g., c-myc.

Expression vectors containing regulatory elements from eukaryotic viruses are typically used in eukaryotic expression vectors, e.g., SV40 vectors, papilloma virus vectors, and vectors derived from Epstein-Barr virus. Other exemplary eukaryotic vectors include pMSG, pAV009/A+, pMTO10/A+, pMAMneo-5, baculovirus pDSVE, and any other vector allowing expression of proteins under the direction of the SV40 early promoter, SV40 later promoter, metallothionein promoter, murine mammary tumor virus promoter, Rous sarcoma virus promoter, polyhedrin promoter, or other promoters shown effective for expression in eukaryotic cells.

Some expression systems have markers that provide gene amplification such as thymidine kinase, hygromycin B phosphotransferase, and dihydrofolate reductase. Alternatively, high yield expression systems not involving gene amplification are also suitable, such as using a baculovirus vector in insect cells, with a Slo3 encoding sequence under the direction of the polyhedrin promoter or other strong baculovirus promoters.

The elements that are typically included in expression vectors also include a replicon that functions in *E. coli*, a gene encoding antibiotic resistance to permit selection of bacteria that harbor recombinant plasmids, and unique restriction sites in nonessential regions of the plasmid to allow insertion of eukaryotic sequences. The particular antibiotic resistance gene chosen is not critical., any of the many resistance genes known in the art are suitable. The prokaryotic sequences are preferably chosen such that they do not interfere with the replication of the DNA in eukaryotic cells, if necessary.

Standard transfection methods are used to produce bacterial, mammalian, yeast or insect cell lines that express large quantities of Slo3 protein, which are then purified using standard techniques (see, e.g., Colley et al., *J. Biol. Chem.* 264:17619–17622 (1989); *Guide to Protein Purification, in Methods in Enzymology*, vol. 182 (Deutscher, ed., 1990)). Transformation of eukaryotic and prokaryotic cells are performed according to standard techniques (see, e.g., Morrison, *J. Bact.* 132:349–351 (1977); Clark-Curtiss & Curtiss, *Methods in Enzymology* 101:347–362 (Wu et al., eds, 1983).

Any of the well known procedures for introducing foreign nucleotide sequences into host cells may be used. These include the use of calcium phosphate transfection, polybrene, protoplast fusion, electroporation, liposomes, microinjection, plasma vectors, viral vectors and any of the other well known methods for introducing cloned genomic DNA, cDNA, synthetic DNA or other foreign genetic material into a host cell (see, e.g., Sambrook et al., supra). It is only necessary that the particular genetic engineering procedure used be capable of successfully introducing at least one gene into the host cell capable of expressing Slo3.

After the expression vector is introduced into the cells, the transfected cells are cultured under conditions favoring expression of Slo3, which is recovered from the culture using standard techniques identified below.

IV. Purification of Slo3

Either naturally occurring or recombinant Slo3 can be purified for use in functional assays. Naturally occurring Slo3 is purified, e.g., from tissue such as testis tissue, and any other source of a Slo3 homolog. Recombinant Slo3 is purified from any suitable expression system.

Slo3 may be purified to substantial purity by standard techniques, including selective precipitation with such substances as ammonium sulfate; column chromatography, immunopurification methods, and others (see, e.g., Scopes, *Protein Purification: Principles and Practice* (1982); U.S. Pat. No. 4,673,641; Ausubel et al., supra; and Sambrook et al., supra).

A number of procedures can be employed when recombinant Slo3 is being purified. For example, proteins having established molecular adhesion properties can be reversible fused to Slo3. With the appropriate ligand, Slo3 can be selectively adsorbed to a purification column and then freed from the column in a relatively pure form. The fused protein is then removed by enzymatic activity. Finally Slo3 could be purified using immunoaffinity columns.

A. Purification of Slo3 from Recombinant Bacteria

Recombinant proteins are expressed by transformed bacteria in large amounts, typically after promoter induction; but expression can be constitutive. Promoter induction with IPTG is a one example of an inducible promoter system. Bacteria are grown according to standard procedures in the art. Fresh or frozen bacteria cells are used for isolation of protein.

Proteins expressed in bacteria may form insoluble aggregates ("inclusion bodies"). Several protocols are suitable for purification of Slo3 inclusion bodies. For example, purification of inclusion bodies typically involves the extraction, separation and/or purification of inclusion bodies by disruption of bacterial cells, e.g., by incubation in a buffer of 50 mM TRIS/HCL pH 7.5, 50 mM NaCl, 5 mM $MgCl_2$, 1 mM DTT, 0.1 mM ATP, and 1 mM PMSF. The cell suspension can be lysed using 2–3 passages through a French Press, homogenized using a Polytron (Brinkman Instruments) or sonicated on ice. Alternate methods of lysing bacteria are apparent to those of skill in the art (see, e.g., Sambrook et al., supra; Ausubel et al., supra).

If necessary, the inclusion bodies are solubilized, and the lysed cell suspension is typically centrifuged to remove unwanted insoluble matter. Proteins that formed the inclusion bodies may be renatured by dilution or dialysis with a compatible buffer. Suitable solvents include, but are not limited to urea (from about 4 M to about 8 M), formamide (at least about 80%, volume/volume basis), and guanidine hydrochloride (from about 4 M to about 8 M). Some solvents which are capable of solubilizing aggregate-forming proteins, for example SDS (sodium dodecyl sulfate), 70% formic acid, are inappropriate for use in this procedure due to the possibility of irreversible denaturation of the proteins, accompanied by a lack of immunogenicity and/or activity. Although guanidine hydrochloride and similar agents are denaturants, this denaturation is not irreversible and renaturation may occur upon removal (by dialysis, for example) or dilution of the denaturant, allowing reformation of immunologically and/or biologically active protein. Other suitable buffers are known to those skilled in the art. Slo3 is separated from other bacterial proteins by standard separation techniques, e.g., with Ni-NTA agarose resin.

Alternatively, it is possible to purify Slo3 from bacteria periplasm. After lysis of the bacteria, when Slo3 is exported into the periplasm of the bacteria, the periplasmic fraction of the bacteria can be isolated by cold osmotic shock in addition to other methods known to skill in the art. To isolate recombinant proteins from the periplasm, the bacterial cells are centrifuged to form a pellet. The pellet is resuspended in a buffer containing 20% sucrose. To lyse the cells, the bacteria are centrifuged and the pellet is resuspended in ice-cold 5 mM $MgSO_4$ and kept in an ice bath for approximately 10 minutes. The cell suspension is centrifuged and the supernatant decanted and saved. The recombinant proteins present in the supernatant can be separated from the host proteins by standard separation techniques well known to those of skill in the art.

B. Standard Protein Separation Techniques For Purifying Slo3

Solubility Fractionation

Often as an initial step, particularly if the protein mixture is complex, an initial salt fractionation can separate many of the unwanted host cell proteins (or proteins derived from the cell culture media) from the recombinant protein of interest. The preferred salt is ammonium sulfate. Ammonium sulfate precipitates proteins by effectively reducing the amount of water in the protein mixture. Proteins then precipitate on the basis of their solubility. The more hydrophobic a protein is, the more likely it is to precipitate at lower ammonium sulfate concentrations. A typical protocol includes adding saturated ammonium sulfate to a protein solution so that the resultant ammonium sulfate concentration is between 20–30%. This concentration will precipitate the most hydrophobic of proteins. The precipitate is then discarded (unless the protein of interest is hydrophobic) and ammonium sulfate is added to the supernatant to a concentration known to precipitate the protein of interest. The precipitate is then solubilized in buffer and the excess salt removed if necessary, either through dialysis or diafiltration. Other methods that rely on solubility of proteins, such as cold ethanol precipitation, are well known to those of skill in the art and can be used to fractionate complex protein mixtures.

Size Differential Filtration

The molecular weight of Slo3 can be used to isolated it from proteins of greater and lesser size using ultrafiltration through membranes of different pore size (for example, Amicon or Millipore membranes). As a first step, the protein mixture is ultrafiltered through a membrane with a pore size that has a lower molecular weight cut-off than the molecular weight of the protein of interest. The retentate of the ultrafiltration is then ultrafiltered against a membrane with a molecular cut off greater than the molecular weight of the protein of interest. The recombinant protein will pass through the membrane into the filtrate. The filtrate can then be chromatographed as described below.

Column Chromatopraphy

Slo3 can also be separated from other proteins on the basis of its size, net surface charge, hydrophobicity, and affinity for ligands. In addition, antibodies raised against proteins can be conjugated to column matrices and the proteins immunopurified. All of these methods are well known in the art. It will be apparent to one of skill that chromatographic techniques can be performed at any scale and using equipment from many different manufacturers (e.g., Pharmacia Biotech).

Alternatively, Slo3 protein can be expressed transiently in a cell by introducing into a cell an RNA encoding the Slo3 protein. The RNA is transcribed in vitro according to standard procedures and then introduced into a cell by means such as injection or electroporation. The RNA then expresses the Slo3 protein. Such systems are useful for measuring single channel and whole cell conductance of a Slo3 channel protein, e.g., when the RNA is transiently expressed in cells such as Xenopus oocytes, CHO, and HeLa cells.

V. Immunological Detection of Slo3

In addition to the detection of Slo3 genes and gene expression using nucleic acid hybridization technology, one can also use immunoassays to detect Slo3. Immunoassays can be used to qualitatively or quantitatively analyze Slo3.

A general overview of the applicable technology can be found in Harlow & Lane, *Antibodies: A Laboratory Manual* (1988).

A. Antibodies to Slo3

Methods of producing polyclonal and monoclonal antibodies that react specifically with Slo3 are known to those of skill in the art (see, e.g., Coligan, *Current Protocols in Immunology* (1991); Harlow & Lane, supra; Goding, *Monoclonal Antibodies: Principles and Practice* (2d ed. 1986); and Kohler & Milstein, *Nature*, 256:495–497 (1975). Such techniques include antibody preparation by selection of antibodies from libraries of recombinant antibodies in phage or similar vectors, as well as preparation of polyclonal and monoclonal antibodies by immunizing rabbits or mice (see, e.g., Huse et al., *Science* 246:1275–1281 (1989); Ward et al., *Nature* 341:544–546 (1989)).

A number of Slo3 comprising immunogens may be used to produce antibodies specifically reactive with Slo3, for example, recombinant Slo3 or a antigenic fragment thereof such as the core or tail domain, is isolated as described herein. Recombinant protein can be expressed in eukaryotic or prokaryotic cells as described above, and purified as generally described above. Recombinant protein is the preferred immunogen for the production of monoclonal or polyclonal antibodies. Alternatively, a synthetic peptide derived from the sequences disclosed herein and conjugated to a carrier protein can be used an immunogen. Naturally occurring protein may also be used either in pure or impure form. The product is then injected into an animal capable of producing antibodies. Either monoclonal or polyclonal antibodies may be generated, for subsequent use in immunoassays to measure the protein.

Methods of production of polyclonal antibodies are known to those of skill in the art. An inbred strain of mice or rabbits is immunized with the protein using a standard adjuvant, such as Freund's adjuvant, and a standard immunization protocol. The animal's immune response to the immunogen preparation is monitored by taking test bleeds and determining the titer of reactivity to Slo3. When appropriately high titers of antibody to the immunogen are obtained, blood is collected from the animal and antisera are prepared. Further fractionation of the antisera to enrich for antibodies reactive to the protein can be done if desired (see Harlow & Lane, supra).

Monoclonal antibodies may be obtained by various techniques familiar to those skilled in the art. Briefly, spleen cells from an animal immunized with a desired antigen are immortalized, commonly by fusion with a myeloma cell (see Kohler & Milstein, *Eur. J. Immunol.* 6:511–519 (1976)). Alternative methods of immortalization include transformation with Epstein Barr Virus, oncogenes, or retroviruses, or other methods well known in the art. Colonies arising from single immortalized cells are screened for production of antibodies of the desired specificity and affinity for the antigen, and yield of the monoclonal antibodies produced by such cells may be enhanced by various techniques, including injection into the peritoneal cavity of a vertebrate host. Alternatively, one may isolate DNA sequences which encode a monoclonal antibody or a binding fragment thereof by screening a DNA library from human B cells according to the general protocol outlined by Huse et al., *Science* 246:1275–1281 (1989).

Monoclonal antibodies and polyclonal sera are collected and titered against the immunogen protein in an immunoassay, for example, a solid phase immunoassay with the immunogen immobilized on a solid support. Polyclonal antisera with a titer of $10^4$ or greater are selected and tested for their cross reactivity against non-Slo3 proteins or even other homologous proteins from other organisms, using a competitive binding immunoassay. Specific polyclonal antisera and monoclonal antibodies will usually bind with a KD of at least about 0.1 mM, more usually at least about 1 $\mu$M, preferably at least about 0.1 $\mu$M or better, and most preferably, 0.01 $\mu$M or better.

Once Slo3 specific antibodies are available, Slo3 can be detected by a variety of immunoassay methods. For a review of immunological and immunoassay procedures, see *Basic and Clinical Immunology* (Stites & Terr eds., 7th ed. 1991). Moreover, the immunoassays of the present invention can be performed in any of several configurations, which are reviewed extensively in *Enzyme Immunoassay* (Maggio, ed., 1980); and Harlow & Lane, supra.

B. Immunological Binding Assays

As explained above, Slo3 expression is associated with sperm physiology, e.g., capacitation and acrosome reactions. Thus, Slo3 provides a marker with which to examine these reactions in sperm. In a preferred embodiment, Slo3 is detected and/or quantified using any of a number of well recognized immunological binding assays (see, e.g., U.S. Pat. Nos. 4,366,241; 4,376,110; 4,517,288; and 4,837,168). For a review of the general immunoassays, see also *Methods in Cell Biology* Volume 37: *Antibodies in Cell Biology* (Asai, ed. 1993); *Basic and Clinical Immunology* (Stites & Terr, eds., 7th ed. 1991).

Immunoassays also often utilize a labeling agent to specifically bind to and label the binding complex formed by the antigen and antibody. The labeling agent may itself be one of the moieties comprising the antibody/antigen complex. Thus, the labeling agent may be a labeled Slo3 polypeptide or a labeled anti-Slo3 antibody. Alternatively, the labeling agent may be another antibody, which specifically binds to the antibody/Slo3 complex. In a one embodiment, the labeling agent is a second Slo3 polypeptide bearing a label. Alternatively, the second antibody may lack a label, but it may, in turn, be bound by a labeled third antibody specific to antibodies of the species from which the second antibody is derived. The second antibody can be modified with a detectable moiety, such as biotin, to which a third labeled molecule can specifically bind, such as enzyme-labeled streptavidin. Other proteins capable of specifically binding immunoglobulin constant regions, such as protein A or protein G, may also be used.

Throughout the assays, incubation and/or washing steps may be required after each combination of reagents. Incubation steps can vary from about 5 seconds to several hours, preferably from about 5 minutes to about 24 hours. However, the incubation time will depend upon the assay format, antigen, volume of solution, concentrations, and the like. Usually, the assays will be carried out at ambient temperature, although they can be conducted over a range of temperatures, such as 10° C. to 40° C.

Non-competitive Assay Formats

Immunoassays for detecting Slo3 in samples may be either competitive or noncompetitive. Noncompetitive immunoassays are assays in which the amount of antigen (in this case the protein) is directly measured. In one preferred "sandwich" assay, for example, the anti-Slo3 antibodies can be bound directly to a solid substrate on which they are immobilized. These immobilized antibodies then capture Slo3 present in the test sample. Slo3 is thus immobilized is then bound by a labeling agent.

Competitive Assay Formats

In competitive assays, the amount of Slo3 present in the sample is measured indirectly by measuring the amount of an added (exogenous) antigen (i.e., the Slo3) displaced (or competed away) from the anti-Slo3 antibody by the antigen present in the sample. In one competitive assay, a known amount of, in this case, the Slo3 is added to the sample and the sample is then contacted with an antibody that specifically binds to the Slo3. The amount of Slo3 bound to the antibody is inversely proportional to the concentration of Slo3 present in the sample. In a particularly preferred embodiment, the antibody is immobilized on a solid substrate. The amount of the Slo3 bound to the antibody may be determined either by measuring the amount of Slo3 present in a Slo3/antibody complex, or alternatively by measuring the amount of remaining uncomplexed protein. The amount of Slo3 may be detected by providing a labeled Slo3 molecule.

A hapten inhibition assay is another preferred competitive assay. In this assay Slo3 is immobilized on a solid substrate. A known amount of anti-Slo3 antibody is added to the sample, and the sample is then contacted with the immobilized Slo3. The amount of anti-Slo3 antibody bound to the immobilized Slo3 is inversely proportional to the amount of Slo3 present in the sample. Again, the amount of immobilized antibody may be detected by detecting either the immobilized fraction of antibody or the fraction of the antibody that remains in solution. Detection may be direct where the antibody is labeled or indirect by the subsequent addition of a labeled moiety that specifically binds to the antibody as described above.

Immunoassays in the competitive binding format can be used for crossreactivity determinations. For example, a protein partially encoded by SEQ ID NO:1, 3, 16, or 18 can be immobilized to a solid support. Proteins are added to the assay that compete with the binding of the antisera to the immobilized antigen. The ability of the above proteins to compete with the binding of the antisera to the immobilized protein is compared to Slo3 encoded by SEQ ID NO:1, 3, 16, or 18. The percent crossreactivity for the above proteins is calculated, using standard calculations. Those antisera with less than 10% crossreactivity with each of the proteins listed above are selected and pooled. The cross-reacting antibodies are optionally removed from the pooled antisera by immunoabsorption with the considered proteins, e.g., distantly related homologs.

The immunoabsorbed and pooled antisera are then used in a competitive binding immunoassay as described above to compare a second protein, thought to be perhaps the protein of this invention, to the immunogen protein (i.e., Slo3 comprising SEQ ID NO:1, 3, 16, or 18). In order to make this comparison, the two proteins are each assayed at a wide range of concentrations and the amount of each protein required to inhibit 50% of the binding of the antisera to the immobilized protein is determined. If the amount of the second protein required to inhibit 50% of binding is less than 10 times the amount of the protein partially encoded by SEQ ID NO:1, 3, 16, or 18 that is required to inhibit 50% of binding, then the second protein is said to specifically bind to the polyclonal antibodies generated to a Slo3 immunogen.

Other Assay Formats

Western blot (immunoblot) analysis is used to detect and quantify the presence of Slo3 in the sample. The technique generally comprises separating sample proteins by gel electrophoresis on the basis of molecular weight, transferring the separated proteins to a suitable solid support, (such as a nitrocellulose filter, a nylon filter, or derivatized nylon filter), and incubating the sample with the antibodies that specifically bind the Slo3. The anti-Slo3 antibodies specifically bind to the Slo3 on the solid support. These antibodies may be directly labeled or alternatively may be subsequently detected using labeled antibodies (e.g., labeled sheep anti-mouse antibodies) that specifically bind to the anti-Slo3 antibodies.

Other assay formats include liposome immunoassays (LIA), which use liposomes designed to bind specific molecules (e.g., antibodies) and release encapsulated reagents or markers. The released chemicals are then detected according to standard techniques (see Monroe et al., *Amer. Clin. Prod. Rev.* 5:34–41 (1986)).

Reduction of Non-specific Binding

One of skill in the art will appreciate that it is often desirable to minimize non-specific binding in immunoassays. Particularly, where the assay involves an antigen or antibody immobilized on a solid substrate it is desirable to minimize the amount of non-specific binding to the substrate. Means of reducing such non-specific binding are co well known to those of skill in the art. Typically, this technique involves coating the substrate with a proteinaceous composition. In particular, protein compositions such as bovine serum albumin (BSA), nonfat powdered milk, and gelatin are widely used with powdered milk being most preferred.

Labels

The particular label or detectable group used in the assay is not a critical aspect of the invention, as long as it does not significantly interfere with the specific binding of the antibody used in the assay. The detectable group can be any material having a detectable physical or chemical property. Such detectable labels have been well-developed in the field of immunoassays and, in general, most any label useful in such methods can be applied to the present invention. Thus, a label is any composition detectable by spectroscopic, photochemical, biochemical, immunochemical, electrical, optical or chemical means. Useful labels in the present invention include magnetic beads (e.g., Dynabeads™), fluorescent dyes (e.g., fluorescein isothiocyanate, Texas red, rhodamine, and the like), radiolabels (e.g., $^3$H, $^{125}$I, $^{35}$S, $^{14}$C, or $^{32}$P), enzymes (e.g., horse radish peroxidase, alkaline phosphatase and others commonly used in an ELISA), and colorimetric labels such as colloidal gold or colored glass or plastic beads (e.g., polystyrene, polypropylene, latex, etc.). The label may be coupled directly or indirectly to the desired component of the assay according to methods well known in the art. As indicated above, a wide variety of labels may be used, with the choice of label depending on sensitivity required, ease of conjugation with the compound, stability requirements, available instrumentation, and disposal provisions.

Non-radioactive labels are often attached by indirect means. Generally, a ligand molecule (e.g., biotin) is covalently bound to the molecule. The ligand then binds to an anti-ligand (e.g., streptavidin) molecule which is either inherently detectable or covalently bound to a signal system, such as a detectable enzyme, a fluorescent compound, or a chemiluminescent compound. A number of ligands and anti-ligands can be used in conjunction with the labeled, naturally occurring anti-ligands. Alternatively, any haptenic or antigenic compound can be used in combination with an antibody.

The molecules can also be conjugated directly to signal generating compounds, e.g., by conjugation with an enzyme or fluorophore. Enzymes of interest as labels will primarily be hydrolases, particularly phosphatases, esterases and glycosidases, or oxidotases, particularly peroxidases. Fluorescent compounds include fluorescein and its derivatives, rhodamine and its derivatives, dansyl, umbelliferone, etc.

Chemiluminescent compounds include luciferin, and 2,3-dihydrophthalazinediones, e.g., luminol. For a review of various labeling or signal producing systems which may be used, see U.S. Pat. No. 4,391,904.

Means of detecting labels are well known to those of skill in the art. Thus, for example, where the label is a radioactive label, means for detection include a scintillation counter or photographic film as in autoradiography. Where the label is a fluorescent label, it may be detected by exciting the fluorochrome with the appropriate wavelength of light and detecting the resulting fluorescence. The fluorescence may be detected visually, by means of photographic film, by the use of electronic detectors such as charge coupled devices (CCDs) or photomultipliers and the like. Similarly, enzymatic labels may be detected by providing the appropriate substrates for the enzyme and detecting the resulting reaction product. Finally simple colorimetric labels may be detected simply by observing the color associated with the label. Thus, in various dipstick assays, conjugated gold often appears pink, while various conjugated beads appear the color of the bead.

Some assay formats do not require the use of labeled components. For instance, agglutination assays can be used to detect the presence of the target antibodies. In this case, antigen-coated particles are agglutinated by samples comprising the target antibodies. In this format, none of the components need be labeled and the presence of the target antibody is detected by simple visual inspection.

VI. Assays for Compounds that Increase or Decrease Ion Flux

Slo3 and its alleles, polymorphic variants, and interspecies homologs are subunits of pH sensitive, voltage-gated channels. The activity of such a channel comprising a Slo3 subunit can be assess using a variety of in vitro and in vivo assays, e.g., measuring current, measuring membrane potential, measuring ion flux, e.g., potassium or rubidium, measuring potassium concentration, measuring second messengers and transcription levels, and using e.g., voltage-sensitive dyes, radioactive tracers, and patch-clamp electrophysiology. Furthermore, such assays can be used to test for inhibitors and activators of channels comprising Slo3. Such modulators of voltage-gated channel activity are useful for investigating and regulating sperm capacitation and the acrosome reaction, as well as for treating disorders related to sperm physiology.

Modulators of Slo3 activity are tested using biologically active Slo3, either recombinant or naturally occurring. The protein can be isolated, expressed in a cell, or expressed in a membrane derived from a cell. Modulation is tested using one of the in vitro or in vivo assays described herein. Samples or assays that are treated with a potential Slo3 inhibitor or activator are compared to control samples without the test compound, to examine the extent of modulation. Compounds that increase the flux of ions will cause a detectable increase in the ion current density by increasing the probability of a channel comprising Slo3 being open, by decreasing the probability of it being closed, increasing conductance through the channel, and allowing the passage of ions.

Increased or decreased flux of ions may be assessed by determining changes in polarization (i.e., electrical potential) of the cell or membrane expressing the Slo3 channel. A preferred means to determine changes in cellular polarization is by measuring changes in current (thereby measuring changes in polarization) with voltage clamp and patch-clamp techniques, e.g., the "cell-attached" mode, the "inside-out" mode, and the "whole cell" mode (see, e.g., Ackerman et al., *New Engl. J. Med.* 336:1575–1595 (1997)). Whole cell currents are conveniently determined using the standard methodology (see, e.g., Hamil et al., *PFlugers. Archiv.* 391:85 (1981). Whole cell currents are also conveniently determined using the conditions set forth in Example IV. Other known assays include: radiolabeled rubidium flux assays and fluorescence assays using voltage-sensitive dyes (see, e.g., Vestergarrd-Bogind et al., *J. Membrane Biol.* 88:67–75 (1988); Daniel et al., *J. Pharmacol. Meth.* 25:185–193 (1991); Holevinsky et al., *J. Membrane Biology* 137:59–70 (1994)).

The effects of the test compounds upon the function of the channels can also be measured by changes in the electrical currents or ionic flux or by the consequences of changes in currents and flux. Changes in electrical current or ionic flux are measured by either increases or decreases in flux of cations such as potassium or rubidium ions. The cations can be measured in a variety of standard ways. They can be measured directly by concentration changes of the ions or indirectly by membrane potential or by radiolabeling of the ions. Consequences of the test compound on ion flux can be quite varied. Accordingly, any suitable physiological change can be used to assess the influence of a test compound on the channels of this invention. The effects of a test compound can be measured by a toxin binding assay. When the functional consequences are determined using intact cells or animals, one can also measure a variety of effects such as transmitter release (e.g., dopamine), hormone release (e.g., insulin), transcriptional changes to both known and uncharacterized genetic markers (e.g., northern blots), cell volume changes (e.g., in red blood cells), immuno-responses (e.g., T cell activation), changes in cell metabolism such as cell growth or pH changes, changes in intracellular second messengers such as $Ca^{2+}$ or IP3, and changes in the sperm capacitation or acrosome reactions.

Assays for compounds capable of inhibiting or increasing potassium flux through the channel proteins comprising Slo3 can be performed by application of the compounds to a bath solution in contact with and comprising cells having an channel of the present invention (see, e.g., Blatz et al., *Nature* 323:718–720 (1986); Park, *J. Physiol.* 481:555–570 (1994)). Generally, the compounds to be tested are present in the range from 1 pM to 100 mM.

Preferably, the Slo3 channel of the assay will be selected from a channel protein of SEQ ID NO:1, 16, or 18 conservatively modified variant thereof. Alternatively, the Slo3 channel of the assay will be derived from a eukaryote and include an amino acid subsequence having sequence similarity to the core domain (S0–S8 of Slo3) of mSlo3 and hSlo3 channel proteins. Generally, the functional Slo3 channel protein will be at least 100, 200, 300, or 400–500 amino acids in length. Generally, the sequence similarity will be at least 60%, typically at least 70%, generally at least 75%, preferably at least 80%, more preferably at least 85%, most preferably at least 90%, and often at least 95%. Thus, Slo3 channel homologs will hybridize, under at least moderate hybridization conditions, to a nucleic acid of at least about 100 nucleotides in length from the core domain of an mSlo3 or hSlo3 nucleic acid and complementary sequences thereof.

The Slo3 channel homologs will generally have substantially similar conductance characteristics (e.g., 80–120 pS) and pH sensitivity characteristics, as described above. Chimeras formed by expression of at least two of mSlo3 and hSlo3 also be used, as well as chimera formed by fusing Slo3 or a Slo3 subsequence to another Slo molecule such as Slo1 or another potassium channel subunit. In a preferred embodiment, the cell placed in contact with a compound which is assayed for increasing or decreasing ion flux is a eukaryotic cell, e.g., an oocyte of Xenopus (e.g., *Xenopus laevis*) or a mammalian cell such as a CHO or HeLa cell.

As described in Example VI, chimeric Slo3 molecules can be made, which combine a subsequence such as either the pore or the tail region of Slo3 with a portion of another molecule, e.g., the pore or tail of another potassium channel subunit such as Slo1, or the pore region from a bacterial channel such as KcsA (McKinnon et al., *Science* 280:106–109 (1998)). Such chimeras provide opportunities to screen and identify modulators of a specific Slo3 region, such as the pore or the tail.

Yet another assay for compounds that increase or decrease potassium flux in pH sensitive potassium channels involves computer assisted drug design, in which a computer system is used to generate a three-dimensional structure of Slo3 proteins based on the structural information encoded by the amino acid sequence. The amino acid sequence interacts directly and actively with a preestablished algorithm in a computer program to yield secondary, tertiary, and quatemary structural models of the protein. The models of the protein structure are then examined to identify regions of the structure that have the ability to bind to ligands. These regions are then used to identify ligands that bind to the protein or regions in which Slo3 interacts with other subunits.

The three-dimensional structural model of the protein is generated by entering channel protein amino acid sequences of at least 10 amino acid residues or corresponding nucleic acid sequences encoding a channel protein into the computer system. The amino acid sequence of the channel protein is selected from the group consisting of: SEQ ID NOS:1, 3, 16, and 18 and conservatively modified versions thereof. The amino acid sequence represents the primary sequence of the protein, which encodes the structural information of the protein. At least 10 residues are entered into the computer system from computer keyboards or computer readable substrates that include, but are not limited to, electronic storage media (e.g., magnetic diskettes, tapes, cartridges, and chips), optical media (e.g., CD ROM), information distributed by internet sites, and RAM. The three-dimensional structural model of the channel protein is then generated by the interaction of the amino acid sequence and the computer system. The software is known to those skilled in the art.

The amino acid sequence represents a primary structure that encodes the information necessary to form the secondary, tertiary and quaternary structure of the monomer protein and channel. The software looks at certain parameters encoded by the primary sequence to generate the structural model. These parameters are referred to as "energy terms," and primarily include electrostatic potentials, hydrophobic potentials, solvent accessible surfaces, and hydrogen bonding. Secondary energy terms include van der Waals potentials. Biological molecules form the structures that minimize the energy terms in a cumulative fashion. The computer program is therefore using these terms encoded by the primary structure or amino acid sequence to create the secondary structural model.

The tertiary structure of the protein encoded by the secondary structure is then formed on the basis of the energy terms of the secondary structure. The user at this point can enter additional variables such as whether the protein is membrane bound or soluble, its location in the body, and its cellular location, e.g., cytoplasmic, surface, or nuclear. These variables along with the energy terms of the secondary structure are used to form the model of the tertiary structure. In modeling the tertiary structure, the computer program matches hydrophobic faces of secondary structure with like, and hydrophilic faces of secondary structure with like.

Finally, quaternary structure of multi-subunit proteins can be modeled in a similar fashion, using anisotropy terms. These terms interface different protein subunits to energetically minimize the interaction of the subunits. In the case of channel proteins, typically four identical subunits make up the quaternary structure of the channel.

Once the structure has been generated, potential ligand binding regions are identified by the computer system. Three-dimensional structures for potential ligands are generated by entering amino acid or nucleotide sequences or chemical formulas of compounds, as described above. The three-dimensional structure of the potential ligand is then compared to that of the channel protein to identify ligands that bind to the channel protein. Binding affinity between the protein and ligands is determined using energy terms to determine which ligands have an enhanced probability of binding to the protein.

Computer systems are also used to screen for mutations of Slo3 genes. Such mutations can be associated with disease states. Once the mutations are identified, diagnostic assays can be used to identify patients having such mutated genes associated with disease states. Identification of the mutated Slo3 genes involves receiving input of a first nucleic acid sequence encoding a pH sensitive potassium channel protein having an amino acid sequence selected from the group consisting of SEQ ID NOS:1, 3, 16, 18 and conservatively modified versions thereof. The sequence is entered into the computer system as described above. The first nucleic acid sequence is then compared to a second nucleic acid sequence that has substantial identity to the first nucleic acid sequence. The second nucleic acid sequence is entered into the computer system in the manner described above. Once the first and second sequences are compared, nucleotide differences between the sequences are identified. Such sequences can represent allelic differences in Slo3 genes, and mutations associated with disease states.

VII. Cellular Transfection and Gene Therapy

The present invention provides packageable Slo3 channel protein nucleic acids (cDNAs), supra, for the transfection of cells in vitro and in vivo. These packageable nucleic acids can be inserted into any of a number of well known vectors for the transfection of target cells and organisms as described below. The nucleic acids are transfected into cells, ex vivo or in vivo, through the interaction of the vector and the target cell. The Slo3 channel protein nucleic acid, under the control of a promoter, then expresses the pH sensitive potassium channel protein of the present invention thereby mitigating the effects of absent, partial inactivation, or abnormal expression of the Slo3 channel protein gene. For example, the Slo3 gene may be used to treat infertility conditions due to its involvement in sperm physiology, e.g., capacitation and acrosome reactions.

Such gene therapy procedures have been used to correct acquired and inherited genetic defects, cancer, and viral infection in a number of contexts. The ability to express artificial genes in humans facilitates the prevention and/or cure of many important human diseases, including many diseases which are not amenable to treatment by other therapies. As an example, in vivo expression of cholesterolregulating genes, genes which selectively block the replication of HIV, and tumor-suppressing genes in human patients dramatically improves the treatment of heart disease, AIDS, and cancer, respectively. For a review of gene therapy procedures, see Anderson, *Science* 256:808–813 (1992); Nabel & Felgner, *TIBTECH* 11:211–217 (1993); Mitani & Caskey, *TIBTECH* 11:162–166 (1993); Dillon, *TIBTECH* 11: 167–175 (1993); Miller, *Nature* 357:455–460 (1992); Van Brunt, *Biotechnology* 6(10):1149–1154 (1988); Vigne, *Restorative Neurology and Neuroscience* 8:35–36 (1995); Kremer & Perricaudet, *British Medical Bulletin* 51(1):31–44 (1995); Haddada et al., in *Current Topics in Microbiology and Immunology*, (Doerfler & Böhm eds., 1995); and Yu et al., *Gene Therapy*, 1:13–26 (1994).

Delivery of the gene or genetic material into the cell is the first critical step in gene therapy treatment of disease. A large number of delivery methods are well known to those of skill in the art. Such methods include, for example liposome-based gene delivery (Mannino & Gould-Fogerite, *BioTechniques* 6:682–691 (1988); U.S. Pat No. 5,279,833; WO 91/06309; and Felgner et al., *Proc. Natl. Acad. Sci. USA* 84:7413–7414 (1987)), and replication-defective retroviral vectors harboring a therapeutic polynucleotide sequence as part of the retroviral genome (see, e.g., Miller et al., *Mol. Cell. Biol.* 10:4239 (1990); Kolberg, *J. NIH Res.* 4:43 (1992); and Cometta et al. *Hum. Gene Ther.* 2:215 (1991)). Widely used retroviral vectors include those based upon murine leukemia virus (MuLV), gibbon ape leukemia virus (GaLV), simian immunodeficiency virus (SIV), human immuno deficiency virus (HIV), and combinations thereof (see, e.g., Buchscher et al., *J. Virol.* 66:2731–2739 (1992); Johann et al., *J. Virol.* 66:1635–1640 (1992); Sommerfelt et al., *Virol.* 176:58–59 (1990); Wilson et al., *J. Virol.* 63:2374–2378 (1989); Miller et al., *J. Virol.* 65:2220–2224 (1991); PCT/US94/05700.

AAV-based vectors are also used to transduce cells with target nucleic acids, e.g., in the in vitro production of nucleic acids and peptides, and for in vivo and ex vivo gene therapy procedures (see, e.g., West et al., *Virology* 160:38–47 (1987); U.S. Pat. No. 4,797,368; WO 93/24641; Kotin, *Human Gene Therapy* 5:793–801 (1994); Muzyczka, *J. Clin. Invest.* 94:1351 (1994). Construction of recombinant AAV vectors are described in a number of publications, including U.S. Pat. No. 5,173,414; Tratschin et al., *Mol. Cell. Biol.* 5:3251–3260 (1985); Tratschin et al., *Mol. Cell. Biol.* 4:2072–2081 (1984); Hermonat & Muzyczka, *Proc. Natl. Acad. Sci. USA* 81:6466–6470 (1984); and Samulski et al., *J. Virol.* 63:03822–3828 (1989). Cell lines that can be transfected by rAAV include those described in Lebkowski et al., *Mol. Cell. Biol.* 8:3988–3996 (1988).

A. Ex vivo Transfection of Cells

Ex vivo cell transfection for diagnostics, research, or for gene therapy (e.g., via re-infusion of the transfected cells into the host organism) is well known to those of skill in the art. In a preferred embodiment, cells are isolated from the subject organism, transfected with an Slo3 channel protein nucleic acid (gene or cDNA), and re-infused back into the subject organism (e.g., patient). Various cell types suitable for ex vivo transfection are well known to those of skill in the art (see, e.g., Freshney et al., *Culture of Animal Cells, a Manual of Basic Technique* (3d ed. 1994)).

As indicated above, in a preferred embodiment, the packageable nucleic acid which encodes an Slo3 channel protein is under the control of an activated or constitutive promoter. The transfected cell(s) express a functional Slo3 channel protein, which mitigates the effects of deficient or abnormal Slo3 channel protein gene expression.

B. In vivo Transfection

Vectors (e.g., retroviruses, adenoviruses, liposomes, etc.) containing therapeutic nucleic acids can be administered directly to the organism for transduction of cells in vivo. Administration is by any of the routes normally used for introducing a molecule into ultimate contact with blood or tissue cells. The packaged nucleic acids are administered in any suitable manner, preferably with pharmaceutically acceptable carriers. Suitable methods of administering such packaged nucleic acids are available and well known to those of skill in the art, and, although more than one route can be used to administer a particular composition, a particular route can often provide a more immediate and more effective reaction than another route.

Pharmaceutically acceptable carriers are determined in part by the particular composition being administered, as well as by the particular method used to administer the composition. Accordingly, there is a wide variety of suitable formulations of pharmaceutical compositions of the present invention.

The packaged nucleic acids, alone or in combination with other suitable components, can be made into aerosol formulations (i.e., they can be "nebulized") to be administered via inhalation. Aerosol formulations can be placed into pressurized acceptable propellants, such as dichlorodifluoromethane, propane, nitrogen, and the like.

Formulations suitable for parenteral administration, such as, for example, by intravenous, intramuscular, intradermal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. In the practice of this invention, compositions can be administered, for example, by intravenous infusion, orally, topically, intraperitoneally, intravesically or intrathecally. The formulations of packaged nucleic acid can be presented in unit-dose or multi-dose sealed containers, such as ampules and vials.

Injection solutions and suspensions can be prepared from sterile powders, granules, and tablets of the kind previously described. Cells transduced by the packaged nucleic acid as described above in the context of ex vivo therapy can also be administered intravenously or parenterally as described above.

The dose administered to a patient, in the context of the present invention should be sufficient to effect a beneficial therapeutic response in the patient over time. The dose will be determined by the efficacy of the particular vector employed and the condition of the patient, as well as the body weight or surface area of the patient to be treated. The size of the dose also will be determined by the existence, nature, and extent of any adverse side-effects that accompany the administration of a particular vector, or transduced cell type in a particular patient.

In determining the effective amount of the vector to be administered in the treatment or prophylaxis of conditions owing to diminished or aberrant expression of Slo3 channel protein, the physician evaluates circulating plasma levels of the vector, vector toxicities, progression of the disease, and the production of anti-vector antibodies. In general, the dose equivalent of a naked nucleic acid from a vector is from about 1 $\mu$g to 100 $\mu$g for a typical 70 kilogram patient, and doses of vectors which include a retroviral particle are calculated to yield an equivalent amount of therapeutic nucleic acid.

For administration, inhibitors and transduced cells of the present invention can be administered at a rate determined by the LD-50 of the inhibitor, vector, or transduced cell type, and the side-effects of the inhibitor, vector or cell type at various concentrations, as applied to the mass and overall health of the patient. Administration can be accomplished via single or divided doses.

Transduced cells are prepared for reinfusion according to established methods (see, e.g., Abrahamsen et al., *J. Clin. Apheresis* 6:48–53 (1991); Carter et al., *J. Clin. Apheresis*, 4:113–117 (1988); Aebersold et al., *J. Immunol. Meth.* 112:1–7 (1988); Muul et al., *J. Immunol. Methods* 101:171–181 (1987); and Carter et al., *Transfusion* 27:362–365 (1987)). After a period of about 24 weeks in culture, the cells should number between $1 \times 10^8$ and $1 \times 10^{12}$. In this regard, the growth characteristics of cells vary from patient to patient and from cell type to cell type. About 72 hours prior to reinfusion of the transduced cells, an aliquot is taken for analysis of phenotype, and percentage of cells expressing the therapeutic agent.

VIII. Chromosomal Assignment of the hSlo3 Gene

To identify the chromosomal location of hSlo3, the cDNA sequences encoding hSlo3 and the 5' and 3' untranslated DNA sequence, as well as DNA sequence derived from genomic DNA may be used to map the hSlo3 gene to a site on a number of different types of genetic maps. This may be accomplished by mapping methods which are well known in molecular genetics, including somatic cell hybrid mapping, radiation hybrid (RH) mapping, and chromosome mapping using fluorescent in situ hybridization (FISH).

An example of one of these methods which is commonly used to map a DNA sequence is the method of radiation hybrid mapping. This procedure allows one to establish with high resolution the position of a DNA sequence within the RH map by comparison of the experimental results with those obtained with known DNA markers, and evaluating the statistical probability that such a map assignment is non-random (see, e.g., Cox et al., *Science* 250:245–250 (1990)).

Typically, a human/hamster somatic cell hybrid panel is used for this purpose. These panels are commercially available, an example of which is the commonly used Stanford G3 panel, available from Research Genetics Inc. The panel is composed of genomic DNA from each of 83 different clonal human/hamster cell hybrid cell lines. Each cell line contains fragments of human genomic DNA in addition to the genomic host DNA of the hamster cell line from which they were derived. Since the human genomic DNA is distributed unevenly among the 83 clonal lines, PCR amplification of a specific human DNA fragment using genomic DNA from each of the clonal lines results in an amplified product in only those clonal lines containing the fragment of the corresponding human genomic DNA. Identification of the lines which produce a positive signal and which do not give a pattern that may be deconvoluted to a map position is determined by comparison of the pattern with patterns derived from other markers in a database, for example the RH server database at the Stanford Human Genome Center. Localization of the RH mapped DNA sequence to a site on a human chromosome may then be established using physical map information derived from nearby known RH markers that have already been assigned a locus on the physical map. This assignment may be accomplished using publicly available databases such as the Genome Database.

The chromosomal localization of Slo3 may be used to determine whether a disease or genetic defect is attributable to changes in the genomic DNA containing the Slo3 gene. Examples of such changes are well known in the literature and include point mutations, insertions, and deletions. Examples of human diseases attributable to changes in genomic DNA sequence include cystic fibrosis and long Q-T syndrome. Association of a disease with changes in the gene coding for a Slo3 may be accomplished by examination of the genetics literature to find diseases for which the chromosomal assignment is already known but for which a specific mutation has not been determined. This can also be accomplished by examining genomic DNA sequence of an individual or group of individuals directly to determine if a mutation has occurred using established methods or a combination of both. Examples of such methods include but are not limited to PCR, single strand conformational polymorphism (SSCP) analysis, and direct sequencing of genomic DNA.

Alternatively, a disease may be mapped to a chromosomal location or a specific gene without prior knowledge of its identity by positional cloning or other methods know to those of skill. The identification of the gene may then be established by comparing the chromosomal location or actual DNA sequence with those derived from the literature or from databases containing known sequence data such as Genbank IX. Kits Slo3 and its homologs are a useful tool for examining expression and regulation of pH sensitive, voltage-gated potassium channels, particularly in developing sperm. Slo3 specific reagents that specifically hybridize to Slo3 nucleic acid, such as Slo3 probes and primers, and Slo3 specific reagents that specifically bind to the Slo3 protein, e.g., Slo3 antibodies are used to examine expression and regulation.

Nucleic acid assays for the presence of Slo3 DNA and RNA in a sample include numerous techniques are known to those skilled in the art, such as Southern analysis, northern analysis, dot blots, RNase protection, SI analysis, amplification techniques such as PCR and LCR, and in situ hybridization. In in situ hybridization, for example, the target nucleic acid is liberated from its cellular surroundings in such as to be available for hybridization within the cell while preserving the cellular morphology for subsequent interpretation and analysis. The following articles provide an overview of the art of in situ hybridization: Singer et al., *Biotechniques* 4:230–250 (1986); Haase et al., *Methods in Virology*, vol. VII, pp. 189–226 (1984); and *Nucleic Acid Hybridization: A Practical Approach* (Hames et al., eds. 1987). In addition, Slo3 protein can be detected with the various immunoassay techniques described above, e.g., ELISA, western blots, etc. The test sample is typically compared to both a positive control (e.g., a sample expressing recombinant Slo3) and a negative control.

The present invention also provides for kits for screening for modulators of Slo3. Such kits can be prepared from readily available materials and reagents. For example, such kits can comprise any one or more of the following materials: biologically active Slo3, reaction tubes, and instructions for testing Slo3 activity. Preferably, the kit contains biologically active Slo3. A wide variety of kits and components can be prepared according to the present invention, depending upon the intended user of the kit and the particular needs of the user. For example, the kit can be tailored for in vitro or in vivo assays for measuring the activity of a homomeric voltage-gated potassium channel comprising an Slo3 subunit.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the appended claims.

EXAMPLES

The following examples are provided by way of illustration only and not by way of limitation. Those of skill in the art will readily recognize a variety of noncritical parameters that could be changed or modified to yield essentially similar results.

Example I

Cloning mSlo3, a pH Sensitive Potassium Channel

The nucleotide sequence for mSlo3 was cloned by searching a database for EST sequences with homology to mSlo1, generating a probe based on the EST sequence using PCR, and screening a library with the EST probe.

A. Methods

By tBlastn (NCBI), an EST (GenBank accession No. AA072586) was identified by homology to the C-terminal "tail" of mSlo1. The EST derived from a mouse promyelocytic WEHI-3 cell line cDNA library. A 32P-labeled 1254 bp PCR ffl product generated from the EST-pBluescript plasmid (Genome Systems) was employed to isolate cDNA clones from a WEHI-3 library (Stratagene) by hybridization. The oligonucleotides used to generate theprobe were 5' GTGGA-TGATACC-GACATGC-TGGAC 3' (sense) (SEQ ID NO:23) 5' GAGACCACCTCTC TCCCGTGTCGT 3' (antisense) (SEQ ID NO:24). mSlo3 expression in the WEHI-3 cell line is apparently anomalous; all isolated cDNAs were inappropriately spliced or truncated, and PCR analysis of the WEHI-3 cDNA bank using combinations of primers homologous to mSlo3 and vector sequence indicated that complete cDNAs were not represented.

Subsequent screening of a mouse testis cDNA library (Dr. Graeme Mardon) yielded cDNAs that extended to the putative initiator methionine, as shown in FIG. 1. The reading frame was closed upstream from the indicated methionine. A full length cDNA was constructed from two overlapping cDNAs and the presence of full length transcripts in testis corresponding to this cDNA was verified by RT-PCR from total testis RNA. The entire cDNA was sequenced in both directions.

For expression in Xenopus oocytes, a Kozak initiator sequence was introduced by PCR and the entire open reading firame was subcloned into the pOocyte-Xpress vector, containing Xenopus 5' and 3' β-globin UTRs. The 5' end generated by PCR was checked for errors by sequencing in both directions.

B. Results mSlo3 cDNA was isolated from a testis cDNA library based on its homology to the large-conductance calcium-activated (BK) potassium channel, mSlo1 (Butler et al., Science 261:221–224 (1993)). The probe was generated from an expressed sequence tag identified in the GenBank database. The new channel was termed mSlo3 ("m" denoting derivation from mouse). FIGS. 1A(1–8) illustrates that the 1113 amino acid mSlo3 is similar to the 1196 amino acid mSlo1 protein (Butler et al., 1993, supra) as well as Drosophila Slo1 (Atlinson et al., Science 253:551–553 (1991); Adelman et al., 1992, supra). The hydrophilicity profiles of both sequences indicate 11 hydrophobic segments, S0 through S10 (FIG. 1B). As with mSlo1, these can be divided into "core" and "tail" domains. Homology of mSlo3 to mSlo1 in the core domain (S0–S8) (51%), which is generally conserved in the voltage-gated superfamily of $K^+$ channels, is much higher than in the tail domain, which is involved in calcium sensing (Wei et al., Neuron 13:671–681 (1994)).

Two notable differences between mSlo3 and mSlo1 demonstrate their functional distinctions. First, the "Calcium Bowl," a hyperconserved aspartate-rich region involved in calcium sensing, is absent in mSlo3 (Schreiber & Salkoff, Biophys. J. 73:1355–1363 (1997)). This absence showed that mSlo3 is gated by factors other than calcium. Second, mSlo3 contained GFG rather than GYG in the conserved pore signature sequence involved in $K^+$ ion selectivity (Yool & Schwarz, Nature 349:700–704 (1991); Hartmann et al., Science 251:942–944 (1991); Heginbotham & MacKinnon, Biophys. J. 66:1061–1067 (1994)). Most $K^+$ selective channels contain GYG. This difference demonstrated that ionic selectivity differs between the two channels: mSlo3 has greater permeability to $Na^+$ than Slo1 channels. A block of conservation containing arginine at regular intervals in the beginning of the S4 region may underlie the fact that, in addition to other factors, both mSlo3 and Slo1 channels are gated by voltage. mSlo3 core residues 35 through 641 share 51% identity with mSlo1. Overall, mSlo3 shares less than 30% amino acid identity with mSlo1.

Example II mRNA Expression of mSlo3

In situ hybridization, northern analysis, RT-PCR, and cDNA cloning were used to investigate mSlo3 expression in a variety of tissues. These experiments demonstrated that mSlo3 is abundant in spermatocytes.

A. Methods

For each tissue tested with RT-PCR, MMLV reverse transcriptase (GIBCO) was used on 5 mg total RNA primed with 25 mM random hexanucleotides (Boehringer Mannheim) and 200 mM dNTPs at 42° C., for 1 hr. 0.1% of each first strand synthesis was assayed by PCR, using 1.0 mM oligonucleotide primers, 200 mM dNTPs and 0.0075 units KlenTaq, cycling 30 times. Reaction products were electrophoresed on 1.5% and 3.0% agarose gels, using standard Tris-borate (TBE) buffer, and visualized by staining with ethidium bromide. PCR primer pairs used were:

mSlo3 (S4 to S5). 5' CTCGAACTCCCTAAAATCTTA-CAGAT 3' (sense) (SEQ ID NO:25) and 5' TTCCGT-TGAGCCAGGGGTCACCAGAATT 3' (antisense) (SEQ ID NO:26) to generate a 156 bp product; mSlo3 (S8 to S9). 5' TCTGCTTTGTGAAGCTAAKTCT 3' sense (SEQ ID NO:27) and 5' TTTCAAAGCCTCTTTAGCGGTAA 3' (antisense) (SEQ ID NO:28) to generate a 690 bp product; mSlo3 (S9 to S10); 5' TTATGCCTGGATCTGCACTCTA-CATG 3' (sense) (SEQ ID NO:29) and 5' ATAGTTTC-CGTCTACTACCGAAA 3' (antisense) (SEQ ID NO:30) to generate a 221 bp product. As a control, Human β-actin. 5' GATGATATCGCCGCGCTCGTCGTCGAC 3' (sense) (SEQ ID NO:31) and 5' TCGGTCCAGGTCTGCGTC-CTACCGTAC 3' (antisense) (SEQ ID NO:32) to generate a 535 bp product.

For northern blot analysis, total RNA or poly A+ RNA was isolated from freshly dissected mouse and human tissue using Trizol (GIBCO). The mouse tissues were brain, heart, skeletal muscle, kidney, lung, liver and testis, the human tissues were spleen, thymus, prostate, testis, uterus, small intestine, colon, and leukocytes. 20 mg total RNA or 2 mg poly A+ RNA from each tissue was electrophoresed on a 1% agarose denaturing gel, using MOPS-formaldehyde buffer, then transferred to nitrocellulose. The human tissue blot was obtained commercially (Clontech). A PCR product generated using primers 5' CGGAAACGTCATGTACAATC-GAAATCCA 3' (sense) (SEQ ID NO:33) and 5' TTCC-GTTG-AGCC-AGGG-GTCACCAGAATT 3' (antisense) (SEQ ID NO:34) was labeled using random hexanucleotides (Boehringer-Mannheim). Blots were hybridized and washed under standard high stringency conditions and exposed to X-ray film for 16 hours. After hybridization with mSlo3 probes, blots were rehybridized with a human β-actin probe to verify RNA loading. For examination of human tissues, 2 mg of poly A+ RNA from the tissues described above were electrophoresed as described. The probe was the mSlo3 probe described above.

For in situ hybridization, testes from white mice >30 days old were dissected, frozen, sectioned immediately with a cryostat, collected on slides, and stored at −20° C. A partial mSlo3 cDNA (approximately 1 kb, corresponding to coding sequence for residues 170–510) was subcloned into pBluescript II KS+ (Stratagene). T3 and T7 RNA polymerase (Stratagene) were used to synthesize 32P-UTP-labeled antisense and sense probes, respectively, from linearized plasmid. Slides were hybridized overnight at 55° C. After washing, slides were dipped in NTB-2 liquid emulsion (Kodak), air dried, and placed in light protected boxes at 4° C. for 10 days.

B. Results

For RT-PCR and northern analysis, mouse brain, skeletal muscle, lung, liver, kidney, and heart tissue were examined; only testis produced a positive signal (FIG. 3). Total RNA blots from the same tissues showed a transcript size of approximately 4 kb, also restricted to testis. Using the mouse Slo3 probe, in human tissues, poly A+ RNA on a northern blot again showed a transcript size of approximately 4 kb, again only in testis.

For in situ hybridization experiments, testes from white mice >30 days old were dissected, frozen, and sectioned immediately with a cryostat, collected on slides, and stored at −20° C. A partial cDNA (approximately 1 kb) for the potassium channel mSlo3 was cloned into the Bluescript expression vector (Stratagene). Both sense and antisense RNA probes were labeled with uridine 5'-[α-$^{32}$P]-triphosphate (10 μCi/μl). Slides were coverslipped and allowed to hybridized overnight at 55° C. Following washing, slides were dehydrated, air dried and dipped in Kodak NTB-2 liquid emulsion, then placed in air tight light boxes at 4° C. for 10 days.

Labeling was observed in annular rings corresponding to the positions of spermatocytes in seminiferous tubules. Positive hybridization signals appeared as white dots on darkfield micrographs. Dense circular patterns of hybridization signals corresponded to the annular clusters of spermatocytes. The annular structure shows the cross-section of a single seminiferous tubule, composed largely of developing spermatocytes. Stem cells and primary spermatocytes were at the outer edges, while more mature spermatocytes were found near the lumen. Supporting Sertoli cells and Leydig cells, difficult to distinguish at this resolution, were present in lower numbers. Hybridization signals at the inner margins of the circular patterns of seminiferous tubules corresponded to the positions of secondary spermatocytes and possibly even spermatids. Dark-field microscopy of the same view shows intense hybridization of antisense probe with mSlo3 mRNA in developing spermatocytes. The outer edges and interstices between tubules are unstained, suggesting that primary and secondary spermatocytes are the predominant cell type expressing the message, rather than spermatogonia (spermatic stem cells). Staining of the innermost regions of the tubule suggests that even early spermatids may be expressing the message. The high density of labeling demonstrates a high degree of mSlo3 expression in spermatocytes.

In addition to the dense patterns of staining in testis in situ, two additional experiments indicated that mSlo3 is abundantly expressed in testis. Northern analysis of total RNA isolated from testis gives a positive signal after only 10 hrs. of exposure. In addition, cDNAs encoding mSlo3 were abundant in a cDNA library constructed from adult testis derived RNA (unique cDNAs encoding mSlo3 represented approximately 0.01% of total cDNAs in the library). In contrast to its abundance in testes, mSlo3 was absent or expressed at much lower levels in other tissues, such as brain, skeletal muscle, and heart.

Example III

Xenopus Oocyte Expression of mSlo3 mSlo3 clones were expressed in Xenopus oocytes, in order to analyze potassium channel function.

A. Methods

As described above in Example I, the entire open reading frame of mSlo3 was assembled in a modified Bluescript II KS+ vector (Stratagene) containing Xenopus 5' and 3' β-globin UTRs. For expression, cRNA was generated from template linearized at a unique vector NotI site and transcribed using the mMessage mMachine T3 kit (Ambion).

B. Results

A full-length mSlo3 cDNA was cloned into pBSC-MXT, a Bluescript-derived plasmid (Stratagene) containing Xenopus β-globin 5' and 3' untranslated sequences. cDNA expression constructs were linearized at a unique Not-I site, and capped cRNA was synthesized using the mMessage mMachine (Ambion). Reactions were precipitated with LiCl to remove the DNA template and resuspended in nuclease-free water at a final concentration of approximately 1 mg/ml. Oocytes were prepared for injection as previously described (Wei et al., Science 248:599–603 (1990)), except for the use of a Drummond nanojector. Approximately 50 nl of RNA in nuclease-free water was injected into each oocyte. Oocytes were incubated in ND96 medium (Wei et al., 1994, supra) and analyzed 1–8 days after injection.

Example IV

Electrophysiology mSlo3 clones expressed in Xenopus oocytes, as described above in Example III, were analyzed for electrophysiological characteristics.

A. Methods cRNA (40 nl at approximately 1 mg/l) was injected into mature Xenopus oocytes; recordings were made 1–8 days later. For whole cell-recording, medium nd96 (concentrations in mM; 96 NaCl, 2 KCl, 1.8 $CaCl_2$, 1 $MgCl_2$, 5 HEPES, pH 7.5) supplemented with 1 mM DIDS (to block endogenous chloride currents) employed as bath solution, or modified as noted in figure legends. Patches were perfused with either 0 $Ca^{2+}$ EGTA solutions (160 K gluconate, 34 KOH, 10 HEPES, and 10 EGTA) or $Ca^{2+}$- containing (184 K gluconate, 10 KOH, 10 HEPES, 200 mM hemicalcium gluconate) solutions. HCl was used to adjust pH. Pipet solution contained 0.5 K gluconate, 0.5 KCl, 1.1 KOH, 10 HEPES, 159 Na gluconate, and 2 hemiMg gluconate, pH 7.1. Recording. Two-electrode voltage clamp was carried out with a TEV-200 amplifier (Dagan). Patch currents were recorded on either an Axopatch 1B or 200A amplifier (Axon), and digitized at either 3.4, 5 or 10 kHz. Data acquisition and analysis programs were CCURRENT and CQUANT (Dr. Keith Baker) or pClamp6 (Axon). Recordings were made at room temperature except tail currents which were recorded at 11° C. using a Peltier device (Cambion).

B. Results

Figure 3A:
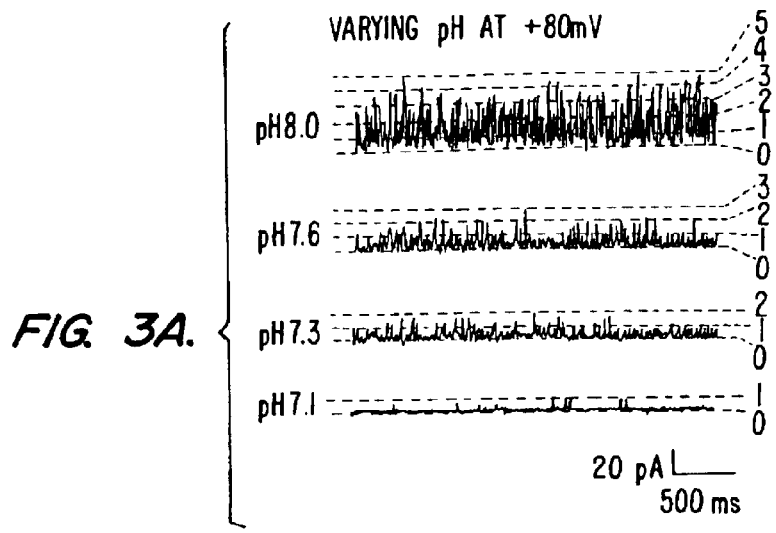
Figure 3B:
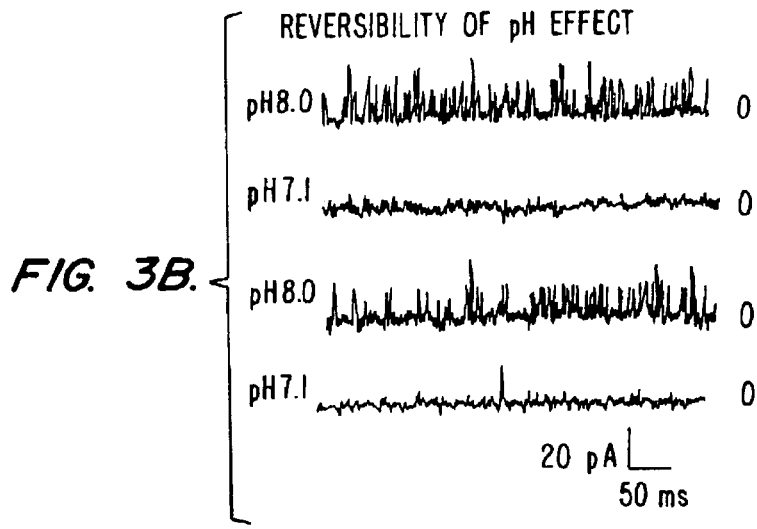
Figure 3C:
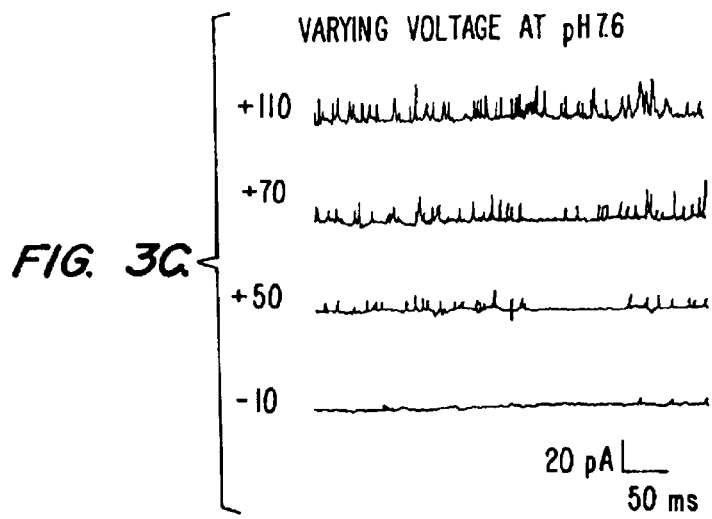
Figure 4A:
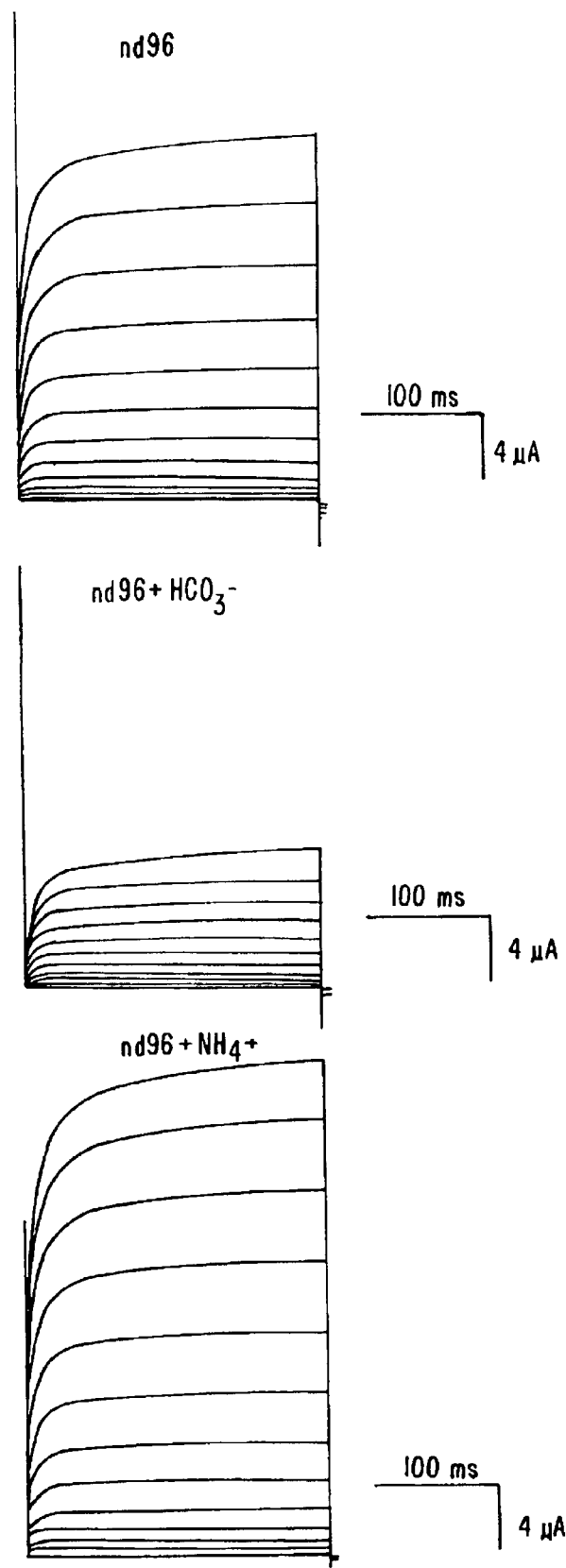
FIGS. 4A–D: mSlo3 whole cell currents from Xenopus oocytes
Figure 4B:
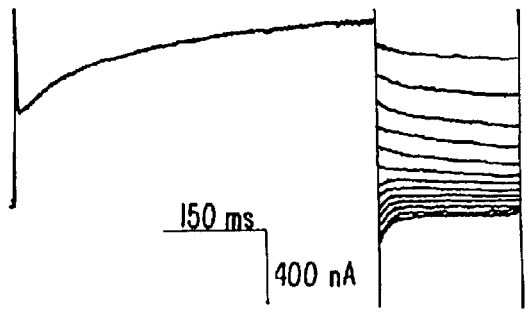
Figure 4C:
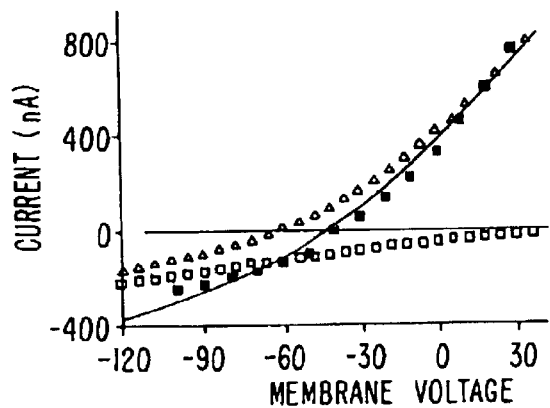
Figure 4D:
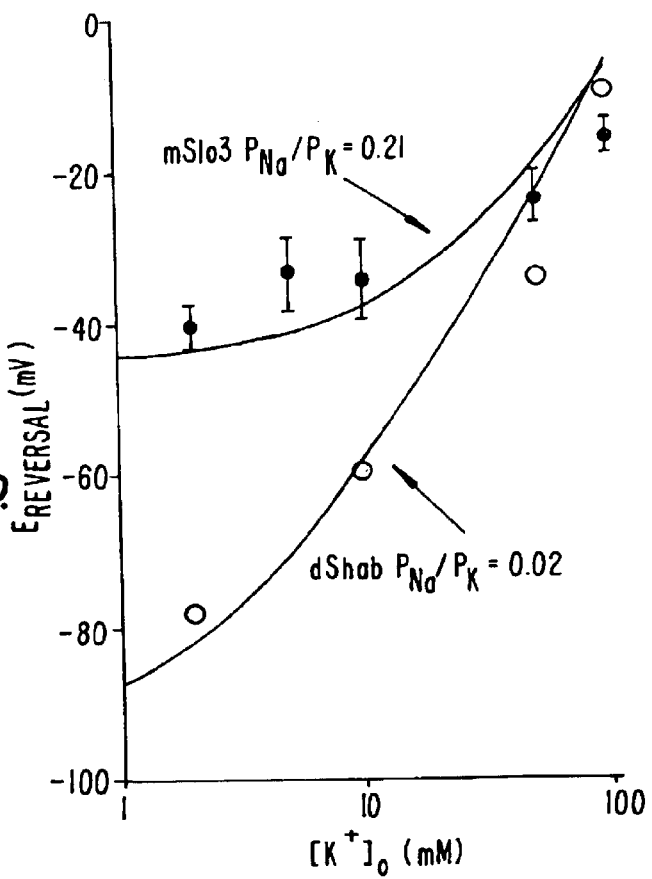

When expressed in the Xenopus oocyte expression system, mSlo3 cRNA produced currents that were sensitive to pH and voltage. Since pHi regulation is critical in spermatic function, mSlo3 activity was tested over a range of pHi in detached, perfused patches (FIG. 3). mSlo3 currents were small or absent at a pHi of 7.1 or lower, while raising pHi resulted in sharp increases in channel activity. Whole-cell mSlo3 currents were also sensitive to manipulations of intracellular pH (FIG. 4). Acidification of the oocyte using bicarbonate-based bath solution strongly attenuated currents, while alkalinization by ammonium chloride reversed this decrease (Fakler et al., *EMBO J.* 15:4093–4099 (1996); Sasaki et al., *Biochim. et Biophys. Acta* 1137:45–51 (1992)). These results are consistent with those obtained with perfused patches. Despite channel rundown, which occurred rapidly over the course of minutes, macroscopic currents could be elicited from large-diameter patch electrodes (FIG. 3D). These currents revealed that although mSlo3 is similar in primary structure to the high conductance $Ca^{2+}$-activated potassium channel mSlo1, mSlo3 activation is not sensitive to $Ca^{2+}$ (FIG. 3D). Channel activity was robust even in the presence of 10 mM EGTA (0 M $Ca^{2+}$ conditions in FIG. 3D, and all experiments in FIGS. 3A–C).

Several other mSlo3 properties were distinct from its closest homolog, mSlo1. mSlo3 single-channel conductance was lower than mSlo1 (approximately 100 pS vs. 270 pS in symmetric $K^+$ as derived from the slope of the unit current amplitude versus voltage relation; Butler et al., 1992, supra). Unlike Slo1, Slo3 was relatively insensitive to TEA (EC50 approximately 100 mM versus less than 0.2 mM for mSlo1), consistent with a Y to V change at residue 283 near the $K^+$ selective pore (Butler et al., 1992, supra; Kavanaugh et al., *J. Biol. Chem.* 266:7583–7587 (1991)). The highly selective mSlo1channel toxin blockers charybdotoxin (50 nM) and iberiotoxin (20 nM) did not affect mSlo3 currents (Miller et al., *Nature*, 313:316–318 (1985); Galvez et al., *J. Biol. Chem.* 265:11083–11090 (1990)). Of particular note, tail current analysis revealed that mSlo3 is less selective for $K^+$ over $Na^+$ than Slo1, having a PK/PNa of approximately 5 versus >50 for mSlo1 (FIGS. 4C, D; Tseng-Crank et al., 1994, supra).

These experiments demonstrated that mSlo3 has the following electrophysiological characteristics when expressed in Xenopus oocytes:

1. mSlo3 is sensitive to pH, being very active above pH 7.1. mSlo3 is outwardly rectifying.
2. Although mSlo3 is structurally related to the Maxi K calcium-activated channel, mSlo1, mSlo3 is insensitive to calcium.
3. In Xenopus oocytes with the symmetric $K^+$ concentrations used above (160 mM KCL), mSlo3 has a single channel conductance of approximately 100 pS.
4. mSlo3 has a relativity high conductivity to $Na^+$ for a $K^+$ channel; the PNa/PK ratio is about 0.25.

Example V

Cloning hSlo3; a Human Homolog of the mSlo3 Channel

Sequence of hSlo3 was obtained by PCR and human testis cDNA library screening, using the mSlo3 sequence as a probe.

A. Methods

The nucleotide sequence of mSlo3 was examined in the core domain, and PCR primers were synthesized to amplify the corresponding segment from a human testis cDNA library (Clontech). The primers were 5' GGCAGCGCTCATTCTTTCCTCCTT-3' and 5' TGCCCAAAACCTCAACCCAAAATA-3' (SEQ ID NO:36). PCR was performed at an annealing temperature of 50° C. for 30 seconds and an extension time of 30 seconds at 72° C. for 40 cycles. PCR fragments were subcloned into pCR II (Invitrogen) and sequenced.

The cDNA library (2×10⁶ pfu) was subsequently screened with a mSlo3 probe. A 2.6 kb BamHI fragment of mSlo3 was labeled with 32P by random primer extension, and bacteriophage lambda plaque filter lifts were hybridized in 30% formamide, 1×Denhardt's, Tris-HCl 20 mM (pH 7.4), 4×SSC, 0.1% SDS, denatured sheared salmon sperm DNA 20 µg/ml, yeast tRNA 20 µg/ml at 42° C. overnight. Filters were washed in 2×SSC/0.1% SDS at 42° C. for 15 minutes× 2, then in 0.2×SSC/0.1% SDS at 42° C. for 30 minutes. Filters were exposed to x-ray film overnight at −80° C. and developed. Bacteriophage plaques that showed corresponding labeling on the autoradiograms were purified to homogeneity, the phage DNA prepared and cDNA inserts excised with EcoRI and subcloned into pBluescript II SK (Stratagene) for sequencing. Sequencing was performed on an ABI automated sequencer.

B. Results

DNA fragments generated by PCR of a human testis cDNA library were sequenced, and the nucleotide sequence obtained (SEQ ID NO:4) was highly homologous with mSlo3, showing approximately 70% sequence identity on the nucleotide level. The translated amino acid sequence (SEQ ID NO:3) was 61.5% identical to mSlo3 on the amino acid level over the sequence region, with 94% identity in the SI region. PCR of human cDNA libraries derived from brain, pancreas, heart, retina, and leukemia cell line (Jurkat) failed to produce the expected band.

Screening of a human testis cDNA library at moderate stringency produced 6 clones, all of which were identified as being hSlo3 by PCR using specific internal primers. One clone was partially sequenced, producing a nucleotide sequence which was identical to the DNA fragments derived from the PCR of the library. Although the clones have not been sequenced in their entirety, the high sequence identity in conjunction with the localization of the channel mRNA to human testis by northern blot (Example II) and PCR establishes the identity of the human Slo3 channel.

Example VI

Slo3/Slo1 Chimeras

In this experiment, a Slo1 core-Slo3 tail chimera has been made, to demonstrate that two distinct regions of the Slo1 tail are involved in calcium sensing. These regions were demonstrated by re-introducing small regions of the Slo1 tail into a calcium-insensitive BK channel constructed from two Slo family members, Slo1 and Slo3 (Schreiber et al., *J. Biol. Chem*. 273:3509–3516 (1998)). Although these regions are adjacent, it is possible that they contribute independently to calcium sensitivity. This independence is supported by the fact that one of the regions that we describe, the Calcium Bowl (Schreiber et al., *Biophys. J*. 73:1355–1363 (1997)) has been modified in another family member, mSlo2, to be a site of chloride regulation, while the channel retains regulation by calcium at a second site.

A. Methods

Wild-type channel constructs. mSlo1 constructs were based on the mbr5 cDNA construct described previously Butler et al., *Science* 261:221–224 (1993)); the mSlo1 and tail were as described in Wei et al., *Neuron* 13:671–681 (1994). Briefly, the mSlo1 core begins at the initiator methionine and terminates after S8 in the unconserved linker region. The mSlo1 tail construct begins at a native internal methionine before the S9 hydrophobic domain. The mSlo3 tail construct is derived form the mSlo3 cDNA (GenBank accession number AF039213; Schreiber. et al., *J. Biol. Chem*. 273:3509–3516 (1998)).

Chimeric mSlo1–mSlo3 tail constructs: mSlo3 and chimeric tail constructs were cloned into pOocyte-Xpress, a Bluescript-derived plasmid (Stratagene) containing Xenopus β-globin 5' and 3' untranslated sequences (Melton et al., *Nucl. Acids Res*. 12:7035–7056 (1984)). Chimeric constructs were generated by standard overlap PCR techniques (Horton et al., *Gene* 77:61–68 (1989)). Oligonucleotides were synthesized at the Washington University Protein and Nucleic Acid Laboratory. The mSlo3 tail construct consisted of the C-terminal region of mSlo3 corresponding to that included in the mSlo1 tail, starting with methion e number 687 in mSlo3 (so that N-terminal residues were MLDS) (SEQ ID NO:5). The iniator methionine was placed into a Kozak consensus sequence (Kozak, *Mol. Biol*. 196:947–950 (1987)). To generate chimeras, the tail domain was divided into segments A through D. First and last residues of each segment are as follows: Region A: replaces mSlo3 792 IAVN . . . LTEL 870 (SEQ ID NOS:37 and 38) with mSlo1 793 RAVN . . . ITEL 885. (SEQ ID NOS:39 and 40) This region begins after S9 and runs to a point just N-terminal to the Calcium Bowl. Region B: replaces mSlo3 871 KNPS GAVF . . . GAVF 906 (SEQ ID NOS:41 and 42) with mSlo1 886 VNDT . . . GTAF 918, (SEQ ID NOS:43 and 44) except that the C-terminal end of this fragment is a hybrid of the mSlo1 and mSlo3 sequences reading GAAF (SEQ ID NO:45). Chimera B tail includes the entire Calcium Bowl region. Region C: replaces mSlo3 899 STSF . . . SEME 941 (SEQ ID NOS:46 and 47) with mSlo1 909 TQPF . . . PELE 963 (SEQ ID NOS:48 and 49). This region includes S10 and 20 residues followving S10. Region D: replace mSlo3 939EMEH . . . HLLP 1034 (SEQ ID NOS:50 and 51) with mSlo1 951 ELEA) . . . ELVP (SEQ ID NO:52) 1048. Region D is a large segment near the C-terminal of the protein. Larger pieces were also generated and denoted by their composition, e.g. BC was a chimeric beginning at the N-tenminal end of B through the C-terminal end of C. Reciprocal experiments, the coexpression of mSlo1tail with mSlo3 core, failed to produce functional channels.

Xenopus oocyte expression: mSlo3 and chimeric tail constructs were linearized at a unique NotI site, and capped cRNA was synthesized using the T3 mMessage mMachine kit (Ambion). Reactions were precipitated with LiCl and resuspended in nuclease-free distilled water at a final concentration of approximately 1.0 mg/mi. Oocytes were prepared for injection as previously described (Wei et al., *Science* 248:599–603 (1990)) except for the use of a Drummond nanojector. Approximately 50 nl was injected into each oocyte. Oocytes were incubated in ND96 medium (Wei et al., *Neuron* 13:671–681 (1994)) and analyzed 1–8 days after injection.

Electrophysiology: Before patch recording, vitelline membranes were removed from oocytes in hypertonic stripping solution (200 mM potassium aspartate, 20 mM KCl, 1 mM $MgCl_2$, 10 mM EGTA, 10 mM HEPES). Inside-out patch recordings were made using buffered calcium perfusion solutions as described previously (Wei. et al, *Neuron* 13:671–681 (1994)). Methanesulfonate-based perfusion and pipet (extracellular) solutions contained symmetric $K^+$ (160 mM), pH 7.0. mSlo1 core+mSlo3 channels were not sensitive to pH in terms of either changes in V50 or Gmax when tested with solutions at pH 7 or 8 containing 184 K gluconate, 10 KOH, 10 HEPES, and 200 μM hemiCa gluconate, pH adjusted with HCl; the pH 7 solution was used in the pipet to provide symrmetric $[K^+]$. From pH 7 to pH 8, $\Delta V50=8.1\pm2.1$ mV; n=6 patches. The ratio of maximal conductances for at pH 8 to that at pH 7 was 0.89±0.12; n=6 patches. Similar results (no effect of pH) were obtained with pH 7 and pH 8 solutions containing nominally zero calcium (10 mM EGTA). Macroscopic currents were measured with an Axopatch 1B amplifier (Axon Instruments), digitized at 10 kHz, and filtered at 5 kHz. Analysis was carried out using pClamp (Axon Instruments). For characterization, each patch was subjected to a family of voltage clamp step pulses in I0 mV increments. Conductance-voltage relations were plotted and fitted with Boltzmann functions. Conductance was then normalized to the maximal conductance of the Boltzmann fit.

B. Results

Considering the role of calcium in Slo1 channel activation, it was surprising to find a closely related channel, Slo3, which was lacking in calcium sensitivity (Schreiber et al., *J. Biol. Chem*. 273:3509–3516 (1998)). Like mSlo1, mSlo3 is a large-conductance, voltage-gated potassium channel with corresponding core and tail domains. However, despite their overall homology, mSlo3 is insensitive to calcium. This lack of calcium sensitivity has allowed production of a chimeric channel with properties similar to the Slo1 core, but lacking calcium sensitivity. This was accomplished by fusing the mSlo3 tail with the mSlo1 core. The Slo1 core construct included the N-terminal two-thirds of mouse Slo1, ending downstream of the S8 hydrophobic segment, in the "linker" region; the Slo3 tail began at a native internal methionine upstream from S9. Remarkably, the Slo3 tail +Slo1 core hybrid channels produced robust expression. The ability of the Slo3 tail to form functional channels with the Slo1 core indicates that the Slo3 tail can supply a function necessary for channel assembly, similar to that of a chaperone, in lieu of the Slo1 tail. This function is likely to be encoded by regions that are conserved between the mSlo1 an mSlo3 tails.

Hybrid channels consisting of Slo3 tail and Slo1 core exhibit voltage sensitivity (as reflected in the slope of the Boltzmann fit to the G-V curve) characteristic of the Slo1 core. This is to be expected if the core determines voltage sensitivity. Most importantly, the chimeric channels were calcium insensitive, which is a characteristic of Slo3 channels. Thus, changing $[Ca^{2+}]$ did not alter the voltage range of activation or the activation kinetics of the chimeric channels, two gating parameters strongly altered by $Ca^{2+}$ in wild-type Slo1 channels (DiChiara et al., *J. Physiol*. 489:403–418 (1995); Cui et al., *J. Gen. Physiol*. 109:647–673 (1997); Cox et al., *J. Gen. Physiol*. 109:633–646 (1997)). These experiments are further evidence for the importance of the Slo1 tail in calcium sensing. This chimeric calcium-insensitive BK channel has been used to identify specific regions of the Slo1 tail involved in calcium sensing.

Chimera ABCD tail produces wild-type Slo1 calcium sensitivity: To map the regions involved in calcium sensitivity, the Slo1 tail was divided into four segments, A through D. To verify that all calcium sensing regions were included, regions A, B, C, and D, when transplanted as a unit (chimera ABCD) were shown to completely restore wild-type calcium sensing to the mSlo3 tail. This indicates that the structures essential to Slo1 calcium sensing are contained within ABCD, a region comprising approximately 56% of the total length of the tail domain. These four regions are contiguous or slightly overlapping and encompass 269 amino acid residues out of a total of 480 Slo tail residues. The hydrophobic region S9 is not included in ABCD. In addition, this result suggests that the remaining N- and C-terminal-most regions of the Slo1 tail that were not transplanted, including the S9 hydrophobic segment and the C-terminal~120 amino acids, are unlikely to make any direct contribution to calcium sensing. However, the regions outside of ABCD may be involved in other roles of the tail that are conserved between Slo1 and Slo3. As mentioned above, one possible function of these regions might be to promote proper channel assembly or targeting to the plasma membrane. Each region (A, B, C, or D) was then tested for its ability to restore calcium sensitivity by adding it back to the Slo3 tail, and testing its calcium sensitivity in Slo3 tail chimera+Slo1 core channels.

The Calcium Bowl (Region B) restores a portion of wild-type calcium sensitivity: In a previous paper a series of mutations in the Calcium Bowl region of the tail was created to show its involvement in the calcium-sensing process (Schreiber et al., *Biophys. J.* 73:1355–1363 (1997)). Further evidence showing the involvement of this region in $Ca^{2+}$ sensing would be provided by adding this region back to the $Ca^{2+}$-insensitive channel and restoring $Ca^{2+}$ sensitivity. Thus, this small region was added (Region B) into the calcium-insensitive Slo3 tail; and then assayed for the calcium-sensitivity of the channels formed from this Slo3 modified tail coexpressed with Slo1 core (chimera B tail+Slo1 core). The results of this experiment show that the Calcium Bowl does, in fact, restore significant calcium sensitivity to the channel. In this experiment, 34 residues encompassing the Calcium Bowl from mSlo1 replaced 37 residues of the mSlo3 tail. Within this region, 12 amino acids were identical; of the 22 additional Slo1 residues added back, 8 represented conservative changes. Overall similarity between the sequences included conservative changes was 59%. The 12 amino acids in conserved positions allowed an accurate alignment through this region. Of the 22 amino acids that differ between the two constructs, seven are negatively charged amino acids present in Slo1 but absent in Slo3; negatively charged amino acids are favored to coordinate calcium (Marsden, *Biochem. Cell. Biol.* 68:587–601 (1990)).

The qualitative effect on $Ca^{2+}$ on channels formed from chimera B tail+Slo1 core was similar to that observed for wild-type mSlo1 (or mSlo1 tail+mSlo1 core) channels; as $[Ca^{2+}]$ was raised, the G-V curve shifted to more negative voltages. Thus, higher $[Ca^{2+}]$ permits the channel to activate at more negative voltages. As with wild-type Slo1, $[Ca^{2+}]$ had little or no effect on the voltage sensitivity of the current, as reflected in the slope of the G-V curve. Although the response to $Ca^{2+}$ was significant in channels formed from chimera B tail+Slo1 core, the magnitude of the $Ca^{2+}$-induced voltage shifts were not equal to that of wild-type channels; The $\Delta V50$ from 4 to 300 $\mu M$ $Ca^{2+}$ was approximately $-58$ $\mu V$ for chimera B tail+Slo1 core, compared with $-84$ mV for wild-type Slo1 tail+Slo1 core. The fact that the magnitude of change in the position of the G-V curve, $\Delta V50/\Delta[Ca^{2+}]$, is less than that with the complete Slo1 tail could be due to several factors, but it is also consistent with previous observations that there is likely to be more than one calcium sensing site per subunit in mSlo1 (Schreiber et al., *Biophys. J.* 73:1355–1363 (1997)). One possibility is that the Calcium Bowl is an autonomous region that is sufficient to confer $Ca^{2+}$ sensing, and an additional region also contributes to the calcium-sensing function.

A region downstream from the Calcium Bowl also contributes to calcium sensing: The region downstream from the Calcium Bowl, which includes the S10 hydrophobic segment (region C), also produced calcium-sensitive channels when incorporated into the Slo3 tail and coexpressed with the Slo1 core (chimera C tail+Slo1core channels. However, increasing $Ca^{2+}$ had a proportionally smaller effect on chimera C tail+Slo1 core channels than on chimera B tail+Slo1 core channels, as reflected in the slope of the V50 versus $[Ca^{2+}]$ relation. As with chimera B tail+Slo1 core channels, the magnitude of the $\Delta V50/\Delta[Ca^{2+}]$ was less than that for mSlo1 tail, suggesting neither region B nor C can separately account for Slo1 calcium sensitivity.

B and C make additive contributions to calcium sensitivity: To assay the effect of combining regions B and C, the chimeric tail construct BC was created. Regions B and C together produce channels with higher calcium than either B or C alone. This shows simple additivity. Over the range of calcium from 0 to 300 $\mu M$ the difference between the V50 for the control mSlo3 tail alone and each chimera was $-77$ mV for chimera B tail and $-27$ mV for chimera C tail. For chimera BC tail, the difference was $-100$ mV. This is remarkably close to the $-104$ mV obtained by adding the values for chimera B and C tails. Thus, these regions appear to make independent contributions to the channel's calcium sensitivity.

Other regions of the tail do not confer calcium sensitivity: In addition to testing regions B and C, the remaining segments of the Slo1 tail were tested. Neither region A nor D produced calcium sensitive channels when incorporated in to the Slo3 tail. Thus, only two limited regions of the tail, B and C, confer calcium sensing properties. Both chimera A tail and D tail shift the starting position of the G-V curve along the voltage axis, but calcium ion has very little effect on the magnitude of the shift. this indicates that in addition to conferring calcium sensitivity, distinct regions of the tail play a role in determining the voltage range of activation of the channel, perhaps by transducing an allosteric interaction of tail and core.

Chimera A, a 93 aa region of mSlo1 tail between S9 and S10 N-terininal to the Calcium Bowl, was also considerably larger than either of the regions that conferred calcium sensitivity. Channels with this tail construct showed no significant response to calcium. However, the voltage range of activation of channels with the chimera tail regions, with a V50 in zero calcium 40 mV more positive than that obtained with the Slo3 tail. In addition chimera A tail showed a slightly reduced G-V slope, quite similar to the decrease in slope seen in 0 $\mu M$ calcium with wild-type mSlo1 tail (Stefani et al., *Proc. Natl. Acad. Sci (USA)* 94:5427–5431 (1997); Cui et al., *J. Gen. Physiol.* 109:647–673 (1997)). A similar effect of region A in shifting the voltage operating range can be seen in comparing channels formed with chimera ABCD tail versus chimera BCD tail: the V50 of chimera ABCD tail+Slo1 core is shifted approximately +60 to +80 mV versus chimera BCD tail at all [$Ca^{2+}$]. Viewed simply as a voltage-dependent channel in the absence of calcium ion, these results suggest region A could be an inhibitory domain responsible for setting the voltage range of activation to very positive values in Wild-type Slo1 channels.

Chimera D, a 98 residue region C-terminal to S10 was the largest single domain transplanted. Like chimera A, channels formed with chimera D tail+Slo1 core also showed no sensitivity to calcium ion. However, the voltage range of activation was repositioned approximately −40 mV relative to that of the Slo3 tail–Slo1 core channels. Although this shift is in the opposite direction of that conferred by chimera A tail, the net effect of having both regions, A and B, is apparently inhibitory, because including both regions (in chimera ABCD tail) produced channels with a very positively shifted current/voltage relation. It is inferred than both region A and B may include, or allosterically influence, the transduction interface between core and tail. In contrast, regions B and C may influence the transduction interface only in a calcium-dependent allosteric manner.

What is claimed is:

1. An isolated nucleic acid encoding a polypeptide monomer of a pH sensitive potassium channel, the monomer:
   (i) forming a potassium channel having a unit conductance of approximately 80–120 pS and having increased potassium channel current activity above approximately intracellular pH of 7.1, when the monomer is expressed in a Xenopus oocyte; and
   (ii) encoded by a nucleic acid that selectively hybridizes under highly stringent hybridization conditions to a nucleic acid comprising a nucleotide sequence of SEQ ID NO:2, SEQ ID NO:17, or SEQ ID NO:19, wherein the hybridization reaction is incubated at 42° C. in a solution comprising 50% formamide, 5×SSC, and 1% SDS and washed at 65° C. in a solution comprising 0.2×SSC and 0.1% SDS.

2. An isolated nucleic acid of claim 1, wherein the nucleic acid encodes, SEQ ID NO:1.

3. An isolated nucleic acid of claim 1, wherein the nucleic acid encodes SEQ ID NO:16 or 18.

4. An isolated nucleic acid sequence of claim 1, wherein the nucleic acid has a nucleotide sequence of SEQ ID NO:2.

5. An isolated nucleic acid sequence of claim 1, wherein the nucleic acid has a nucleotide sequence of SEQ ID NO:17, or SEQ ID NO:19.

6. An expression vector comprising a nucleic acid of claim 1.

7. A host cell transfected with the vector of claim 6.

8. The nucleic acid of claim 1, wherein the nucleic acid encodes a polypeptide monomer having a calculated molecular weight of between 120–156 kDa, the molecular weight calculated from amino acid sequence.

9. The nucleic acid of claim 1, wherein the nucleic acid encodes a polypeptide monomer forming a homomeric potassium channel.

10. The nucleic acid of claim 1, wherein the nucleic acid encodes a polypeptide monomer forming a heteromeric potassium channel.

* * * * *

SEQUENCE LISTING

<160> NUMBER OF SEQ ID NOS: 53

<210> SEQ ID NO 1
<211> LENGTH: 1112
<212> TYPE: PRT
<213> ORGANISM: Mus musculus
<220> FEATURE:
<223> OTHER INFORMATION: mouse Slo3 (mSlo3)
<220> FEATURE:
<221> NAME/KEY: VARIANT
<222> LOCATION: (5)
<223> OTHER INFORMATION: polymorphic variant #2 Leu -> Ile
<220> FEATURE:
<221> NAME/KEY: VARIANT
<222> LOCATION: (21)
<223> OTHER INFORMATION: polymorphic variant #1 Ile -> Val
<220> FEATURE:
<221> NAME/KEY: VARIANT
<222> LOCATION: (25)
<223> OTHER INFORMATION: polymorphic variant #3 Ala -> Ser

<400> SEQUENCE: 1

Met Ser Gln Thr Leu Leu Asp Ser Leu Asn Gln Lys Glu Leu Thr Glu
 1               5                  10                  15

Thr Ser Cys Thr Ile Glu Ile Gln Ala Ala Phe Ile Leu Ser Ser Leu
                20                  25                  30

Ala Thr Phe Phe Gly Gly Leu Ile Ile Leu Phe Leu Phe Arg Ile Ala
            35                  40                  45

Leu Lys Ser Ser Arg Ser Trp Lys Tyr Val Lys Gly Pro Arg Gly Leu
    50                  55                  60

Leu Glu Leu Phe Ser Ser Arg Arg Ile Glu Ala Asn Pro Leu Arg Lys
65                  70                  75                  80

Leu Tyr Phe His Gly Val Phe Arg Gln Arg Ile Glu Met Leu Leu Ser
                85                  90                  95

Ala Gln Thr Val Val Gly Gln Val Leu Val Ile Leu Val Phe Val Leu
            100                 105                 110

Ser Ile Gly Ser Leu Val Ile Tyr Phe Ile Asn Ser Met Asp Pro Val
        115                 120                 125

Arg Arg Cys Ser Ser Tyr Glu Asp Lys Ile Val His Gly Asp Leu Ser
    130                 135                 140

Phe Asn Ala Phe Phe Ser Phe Tyr Phe Gly Leu Arg Phe Trp Ala Ala
145                 150                 155                 160

Glu Asp Lys Ile Lys Phe Trp Leu Glu Met Asn Ser Ile Val Asp Ile
                165                 170                 175

Phe Thr Ile Pro Pro Thr Phe Ile Ser Tyr Tyr Leu Lys Ser Asn Trp
            180                 185                 190

Leu Gly Leu Arg Phe Leu Arg Ala Leu Arg Leu Leu Glu Leu Pro Lys
        195                 200                 205

-continued

```
Ile Leu Gln Ile Leu Gln Val Ile Lys Thr Ser Asn Ser Val Lys Leu
    210                 215                 220
Ser Lys Leu Leu Ser Ile Val Ile Ser Thr Trp Phe Thr Ala Ala Gly
225                 230                 235                 240
Phe Leu His Leu Val Glu Asn Ser Gly Asp Pro Trp Leu Asn Gly Arg
                245                 250                 255
Asn Ser Gln Thr Met Ser Tyr Phe Glu Ser Ile Tyr Leu Val Thr Ala
            260                 265                 270
Thr Met Ser Thr Val Gly Phe Gly Asp Val Val Ala Lys Thr Ser Leu
        275                 280                 285
Gly Arg Ile Phe Ile Val Phe Phe Thr Leu Gly Ser Leu Ile Leu Phe
    290                 295                 300
Ala Asn Tyr Ile Pro Glu Met Val Glu Leu Phe Ser Thr Arg Lys Lys
305                 310                 315                 320
Tyr Thr Lys Pro Tyr Glu Ala Val Lys Gly Lys Lys Phe Ile Val Val
                325                 330                 335
Cys Gly Asn Ile Thr Val Asp Ser Val Thr Ala Phe Leu Arg Asn Phe
            340                 345                 350
Leu His Trp Lys Ser Gly Glu Ile Asn Ile Glu Ile Val Phe Leu Gly
        355                 360                 365
Glu Thr Leu Pro Cys Leu Glu Leu Glu Thr Leu Leu Lys Cys His Thr
    370                 375                 380
Ser Cys Thr Asn Phe Val Cys Gly Thr Ala Leu Lys Phe Glu Asp Leu
385                 390                 395                 400
Lys Arg Val Ala Val Glu Asn Ser Glu Ala Cys Leu Ile Leu Ala Asn
                405                 410                 415
His Phe Cys Ser Asp Leu His Asp Glu Asp Asn Ser Asn Ile Met Arg
            420                 425                 430
Val Leu Ser Ile Lys Asn Tyr Tyr Pro Gln Thr Arg Val Ile Ile Gln
        435                 440                 445
Ile Leu Gln Ser Gln Asn Lys Val Phe Leu Ser Lys Ile Pro Asn Trp
    450                 455                 460
Asp Trp Ser Ala Gly Asp Asn Ile Leu Cys Phe Ala Glu Leu Lys Leu
465                 470                 475                 480
Gly Phe Ile Ala Gln Gly Cys Leu Val Pro Gly Leu Cys Thr Phe Leu
                485                 490                 495
Thr Thr Leu Phe Ile Glu Gln Asn Gln Lys Val Phe Pro Lys His Pro
            500                 505                 510
Trp Gln Lys His Phe Leu Asn Gly Leu Lys Asn Lys Ile Leu Thr Gln
        515                 520                 525
Arg Leu Ser Asn Asp Phe Val Gly Met Thr Phe Pro Gln Val Ser Arg
    530                 535                 540
Leu Cys Phe Val Lys Leu Asn Leu Met Leu Ile Ala Ile Gln His Lys
545                 550                 555                 560
Pro Phe Phe His Ser Cys Cys Thr Leu Ile Leu Asn Pro Ser Ser Gln
                565                 570                 575
Val Arg Leu Asn Lys Asp Thr Leu Gly Phe Phe Ile Ala Asp Ser Ser
            580                 585                 590
Lys Ala Val Lys Arg Ala Phe Tyr Cys Ser Asn Cys His Ser Asp
        595                 600                 605
Val Cys Asn Pro Glu Leu Ile Gly Lys Cys Asn Cys Lys Ile Lys Ser
    610                 615                 620
```

```
Arg Gln Gln Leu Ile Ala Pro Thr Ile Met Val Met Lys Ser Ser Leu
625                 630                 635                 640

Thr Asp Phe Thr Thr Ser Ser His Ile His Ala Ser Met Ser Thr Glu
            645                 650                 655

Ile His Thr Cys Phe Ser Arg Glu Gln Pro Ser Leu Ile Thr Ile Thr
                660                 665                 670

Thr Asn Arg Pro Thr Thr Asn Asp Thr Val Asp Asp Thr Asp Met Leu
            675                 680                 685

Asp Ser Ser Gly Met Phe His Trp Cys Arg Ala Met Pro Leu Asp Lys
            690                 695                 700

Val Val Leu Lys Arg Ser Glu Lys Ala Lys His Glu Phe Gln Asn His
705                 710                 715                 720

Ile Val Val Cys Val Phe Gly Asp Ala Gln Cys Thr Leu Val Gly Leu
                725                 730                 735

Arg Asn Phe Val Met Pro Leu Arg Ala Ser Asn Tyr Thr Arg Gln Glu
                740                 745                 750

Leu Lys Asp Ile Val Phe Ile Gly Ser Leu Glu Tyr Phe Gln Arg Glu
            755                 760                 765

Trp Arg Phe Leu Arg Asn Phe Pro Lys Ile His Ile Met Pro Gly Ser
770                 775                 780

Ala Leu Tyr Met Gly Asp Leu Ile Ala Val Asn Val Glu Gln Cys Ser
785                 790                 795                 800

Met Cys Val Ile Leu Ala Thr Pro Tyr Lys Ala Leu Ser Ser Gln Ile
                805                 810                 815

Leu Val Asp Thr Glu Ala Ile Met Ala Thr Leu Asn Ile Gln Ser Leu
            820                 825                 830

Arg Ile Thr Ser Pro Thr Pro Gly Ser Ser Lys Ser Glu Val Lys Pro
            835                 840                 845

Ser Ser Ala Phe Asp Ser Lys Glu Arg Lys Gln Arg Tyr Lys Gln Ile
850                 855                 860

Pro Ile Leu Thr Glu Leu Lys Asn Pro Ser Asn Ile His Phe Ile Glu
865                 870                 875                 880

Gln Met Gly Gly Leu Asp Gly Met Leu Lys Gly Thr Ser Leu His Leu
                885                 890                 895

Ser Thr Ser Phe Ser Thr Gly Ala Val Phe Ser Asp Thr Phe Leu Asp
                900                 905                 910

Ser Leu Leu Ala Thr Ser Phe Tyr Asn Tyr His Val Val Glu Leu Leu
            915                 920                 925

Gln Met Leu Val Thr Gly Gly Ile Ser Ser Glu Met Glu His Tyr Leu
930                 935                 940

Val Lys Glu Lys Pro Tyr Lys Thr Thr Asp Asp Tyr Glu Ala Ile Lys
945                 950                 955                 960

Ser Gly Arg Thr Arg Cys Lys Leu Gly Leu Leu Ser Leu Asp Gln Thr
                965                 970                 975

Val Leu Ser Gly Ile Asn Pro Arg Lys Thr Phe Gly Gln Leu Phe Cys
            980                 985                 990

Gly Ser Leu Asp Asn Phe Gly Ile Leu Cys Val Gly Leu Tyr Arg Met
            995                 1000                1005

Ile Asp Glu Glu Glu Pro Ser Gln Glu His Lys Arg Phe Val Ile Thr
    1010                1015                1020

Arg Pro Ser Asn Glu Cys His Leu Leu Pro Ser Asp Leu Val Phe Cys
1025                1030                1035                1040

Ala Ile Pro Phe Asn Thr Thr Cys Gly Lys Ser Asp Ser Ser Pro Phe
```

```
                1045              1050             1055
Asn Phe Arg Leu Lys Thr Thr Leu Gln Thr Arg Arg His Trp Pro
        1060              1065             1070

Arg Gly Arg Ile Ser Ser Ile Arg Thr Met Pro Thr Ser Pro Thr Ile
    1075              1080             1085

Phe Thr Gln Ser Thr Thr Arg Glu Arg Gly Gly Leu Ser Thr Thr Thr
    1090              1095             1100

Pro Glu Ser Ile Leu Trp Thr Arg
1105            1110

<210> SEQ ID NO 2
<211> LENGTH: 3339
<212> TYPE: DNA
<213> ORGANISM: Mus musculus
<220> FEATURE:
<223> OTHER INFORMATION: mouse Slo3 (mSlo3)

<400> SEQUENCE: 2
atgtctcaaa cattgctaga cagtttaaat cagaaggagt tgacggaaac gtcatgtaca      60
atcgaaatcc aggcagcgtt cattctttcc tccttggcga cttcttcgg gggactcatc     120 atcttattcc ttttcagaat agccttgaaa agctcaagaa gttggaaata cgtcaagggg    180
ccaagaggac tcttgaact attctcatca cgtagaatcg aggctaatcc tttgaggaaa     240
ctttactttc atggagtatt tcgtcagcgc atcgaaatgc tgctttctgc acagaccgtc    300
gtggggcaag tgttggtgat ccttgtcttt gtactaagca tcgggtctct tgtgatctat    360
ttcatcaatt caatggatcc tgttcgaagg tgttcttcat atgaagacaa aattgtccat    420
ggggatttga gttcaacgc tttctttagc ttctattttg ggttgaggtt ttgggcagct     480
gaagacaaga tcaagttctg gttggagatg aattcaattg tagacatttt taccatcccg    540 ccaacctta tttcttatta tttgaagagt aattggctag gtttgagatt tctaagagct     600
ctgcggttgc tcgaactccc taaaatctta cagatcctac aagtcatcaa gaccagcaat    660
tcagtgaagc tttccaaact gttgtcaata gttatcagta cctggttcac ggcagcagga    720
ttccttcacc tggtggaaaa ttctggtgac cctggctca acggaagaaa ctcacagact     780
atgtcatact ttgagtctat ttatctggtg acagcaacaa tgtcaactgt tggctttggg    840
gacgtggtgg ccaagacatc cctaggacgg attttcattg ttttcttcac ccttgggagt    900
ttgatactat ttgcaaacta cattccagaa atggtggagc tcttttctac aggaagaaa    960 tacaccaagc cctacgaagc agtcaaagga aaaaagttca tcgtggtctg tggaaacatc   1020
acagttgaca gtgttactgc tttcctgagg aattttctcc actggaagtc cggggaaatc   1080
aatattgaga tcgtattcct tggagagact ctcccttgct tggaactgga ccttactg     1140 aagtgccaca catcctgtac caacttcgta tgcggcaccg cactgaagtt cgaggatctg   1200
aagcgagttg cagtggagaa ctcggaggcg tgcctgattc tagccaacca tttctgtagt   1260
gacttacatg acgaagacaa ctcaaacatt atgagggtgc tctcgatcaa gaactattat   1320
ccacagacca gagtcatcat tcagatactt cagtctcaaa acaaggtttt cctgtcaaaa   1380
atccccaact gggactggag tgctggagac aatatcctct gctttgcaga gctaaagctc   1440
ggatttatcg cccaaggctg cttggtgcca gggctgtgca cctttctcac gactctgttc   1500
attgaacaaa accaaaaggt ttttcctaaa catccctggc aaaaacattt cttgaatggc   1560
ttgaagaaca gattctgac acagcgcctc tctaacgact tcgtggggat gacatttccc   1620
caggtctccc ggctctgctt tgtgaagcta aatctcatgc tgatcgccat ccaacacaag   1680
```

-continued

```
ccctcttttc acagttgttg cactctgata ctaaacccat catcccaagt gaggctgaat    1740 aaggacaccct tagggttctt cattgcggac tcctccaaag ccgtcaaaag ggctttcttt    1800
tactgttcca actgtcacag cgatgtgtgc aatcctgagc taattggaaa gtgtaactgt    1860
aaaatcaaga gccgacaaca actcatagca ccgaccatca tggtgatgaa agcagcttg    1920 accgatttca ccacttcttc acacatccac gcttctatgt caacagaaat tcacacttgt    1980
ttttcaagag aacagcctag tttgatcacc attacaacca acagaccaac gacaaacgac    2040
acagtggatg ataccgacat gctggacagc agtggcatgt tcactggtg cagagcaatg     2100 cccttggaca aggtggttct gaaacgaagt gagaaggcaa aacacgagtt tcagaaccac    2160
attgtagtat gcgtgtttgg agatgcccaa tgtaccctgg tggggcttcg gaatttcgtg    2220
atgcccctga gagccagcaa ctacacccgg caggagctga aggacattgt ttttattggg    2280
tctctggagt acttccagag agaatggcga tttctccgaa actttcccaa gatacacatt    2340
atgcctggat ctgcactcta catgggagat ctgattgcag tcaatgtaga gcagtgctct    2400
atgtgcgtca tcttagccac accctacaag gcactgagca gccagattct ggtggacaca    2460
gaggccatca tggccaccct caacatccag tccctgcgga tcaccagtcc tactccaggg    2520
tcttcaaagt cagaagtaaa gccatcatct gcctttgata gtaaagaaag gaagcaaaga    2580
tacaaacaga tccccattct cactgaactg aagaatccct ccaacatcca ctttattgag    2640
cagatgggcg gactgatgg aatgctcaaa gggactagct tgcatctcag cacttctttc     2700
tccaccggtg ctgtcttttc agacaccttc ttggattctc tcctgccac gtccttctac     2760 aattaccatg tcgtggaatt acttcagatg ctagtgactg gaggcataag ctctgagatg    2820
gaacactatt tggttaagga gaagccctat aagacaactg acgactatga ggcaatcaag    2880
tctgggagga cgcggtgtaa gctgggactc ctctctttag accaaaccgt tctatcaggc    2940
attaatccaa gaaaaaccatt tggacagctg ttctgtggct cattggataa tttcgggatc    3000
ctatgtgtcg gcttataccg tatgattgat gaagaggaac ccagccaaga acacaaaagg    3060
tttgtgatca ccaggccatc caatgagtgc cacctgctgc cctcagatct cgtgttttgt    3120
gccatccctt tcaacaccac ctgtggcaaa tcagacagca gtccttttcaa tttcaggctc    3180 aaaacaactc tacaaacgcg acgacgccat tggcccaggg gtcgaattc ttcgattcgc      3240 accatgccga cgagtcccac gatctttacc cagtcgacga cacgggagag aggtggtctc    3300
agcaccacca ctcccgagtc tatcctttgg acacgttag                          3339
```

<210> SEQ ID NO 3
<211> LENGTH: 112
<212> TYPE: PRT
<213> ORGANISM: Homo sapiens
<220> FEATURE:
<223> OTHER INFORMATION: human Slo3-a (hSlo3-a)
<220> FEATURE:
<221> NAME/KEY: MOD_RES
<222> LOCATION: (29)
<223> OTHER INFORMATION: Xaa = any amino acid

<400> SEQUENCE: 3

```
Gly Leu Ala Ala Leu Ile Leu Ser Ser Phe Val Thr Leu Phe Ser Gly
  1               5                  10                  15

Leu Ile Ser Leu Leu Ile Phe Arg Leu Ile Trp Arg Xaa Val Lys Lys
             20                  25                  30

Trp Gln Ile Ile Lys Gly Thr Gly Ile Ile Leu Glu Leu Phe Thr Ser
         35                  40                  45
```

```
Gly Thr Ile Ala Arg Ser His Val Arg Ser Leu His Phe Gln Gly Gln
        50                  55                  60

Phe Arg Asp His Ile Glu Met Leu Leu Ser Ala Gln Thr Phe Val Gly
 65                  70                  75                  80

Gln Val Leu Val Ile Leu Val Phe Val Leu Ser Ile Gly Ser Leu Ile
                 85                  90                  95

Ile Tyr Phe Ile Asn Ser Ala Asp Pro Val Gly Thr Leu Phe Ile Ile
            100                 105                 110
```

<210> SEQ ID NO 4
<211> LENGTH: 416
<212> TYPE: DNA
<213> ORGANISM: Homo sapiens
<220> FEATURE:
<223> OTHER INFORMATION: human Slo3 (hSlo3)

<400> SEQUENCE: 4

```
ggcttggcag cgctcattct ttcctccttt gtgaccctct tcagtggact catcagcctg      60
ttgatcttca ggctgatctg gagayctgtt aaaaaatggc aaatcatcaa gggaacagga    120
attatcttgg aactgttcac atcaggtacc atcgctagga gccatgtaag aagcctccac    180
ttccagggac aatttcgtga tcatatagaa atgttgcttt cagcccagac ctttgtgggg    240
caagtgttgg tgatccttgt ctttgtacta agcattgggt ctcttataat ctatttcatc    300
aattcwgctg accctgttgg aacgctgttc atcatatgaa gacaaaacca ttcctattga    360
tttggttttc aatgctttct ttagtttcta ttttgggttg aggttttggc aaagcc        416
```

<210> SEQ ID NO 5
<211> LENGTH: 4
<212> TYPE: PRT
<213> ORGANISM: Mus musculus
<220> FEATURE:
<221> NAME/KEY: PEPTIDE
<222> LOCATION: (1)..(4)
<223> OTHER INFORMATION: mSlo3 peptide starting with amino acid 687

<400> SEQUENCE: 5

```
Met Leu Asp Ser
 1
```

<210> SEQ ID NO 6
<211> LENGTH: 112
<212> TYPE: PRT
<213> ORGANISM: Homo sapiens
<220> FEATURE:
<223> OTHER INFORMATION: human Slo3-b (hSlo3-b)
<220> FEATURE:
<221> NAME/KEY: MOD_RES
<222> LOCATION: (29)
<223> OTHER INFORMATION: Xaa = any amino acid

<400> SEQUENCE: 6

```
Gly Leu Ala Ala Leu Ile Leu Ser Ser Phe Val Thr Leu Phe Thr Gly
 1               5                  10                  15

Leu Ile Ser Leu Leu Ile Phe Arg Leu Ile Trp Arg Xaa Val Lys Lys
            20                  25                  30

Trp Gln Ile Ile Lys Gly Thr Gly Ile Ile Leu Glu Leu Phe Thr Ser
        35                  40                  45

Gly Thr Ile Ala Arg Ser His Val Arg Ser Leu His Phe Gln Gly Gln
     50                  55                  60

Phe Arg Asp His Ile Glu Met Leu Leu Ser Ala Gln Thr Phe Val Gly
```

```
                65                  70                  75                  80
Gln Val Leu Val Ile Leu Val Phe Val Leu Ser Ile Gly Ser Leu Ile
                    85                  90                  95
Ile Tyr Phe Ile Asn Ser Ala Asp Pro Val Gly Thr Leu Phe Ile Ile
                    100                 105                 110

<210> SEQ ID NO 7
<211> LENGTH: 112
<212> TYPE: PRT
<213> ORGANISM: Homo sapiens
<220> FEATURE:
<223> OTHER INFORMATION: human Slo3-c (hSLO3-c)
<220> FEATURE:
<221> NAME/KEY: MOD_RES
<222> LOCATION: (29)
<223> OTHER INFORMATION: Xaa = any amino acid

<400> SEQUENCE: 7

Gly Leu Ala Ala Leu Ile Leu Ser Ser Phe Val Thr Leu Phe Ser Gly
 1               5                  10                  15
Leu Ile Ser Leu Leu Ile Phe Arg Leu Ile Trp Arg Xaa Val Lys Lys
                    20                  25                  30
Trp Gln Ile Ile Lys Gly Thr Gly Ile Ile Leu Glu Leu Phe Thr Ser
                35                  40                  45
Gly Thr Ile Ala Arg Ser His Val Arg Ser Leu His Phe Gln Gly Gln
            50                  55                  60
Phe Arg Asp His Ile Glu Met Leu Leu Ser Ala Gln Thr Phe Val Gly
65                  70                  75                  80
Gln Val Leu Val Ile Leu Val Phe Val Leu Ser Ile Gly Ser Leu Ile
                    85                  90                  95
Ile Tyr Phe Ile Asn Ser Met Asp Pro Val Gly Thr Leu Phe Ile Ile
                    100                 105                 110

<210> SEQ ID NO 8
<211> LENGTH: 26
<212> TYPE: DNA
<213> ORGANISM: Artificial Sequence
<220> FEATURE:
<223> OTHER INFORMATION: Description of Artificial Sequence:mSlo3 primer

<400> SEQUENCE: 8
ctcgaactcc ctaaatctt acagat                                        26

<210> SEQ ID NO 9
<211> LENGTH: 28
<212> TYPE: DNA
<213> ORGANISM: Artificial Sequence
<220> FEATURE:
<223> OTHER INFORMATION: Description of Artificial Sequence:mSlo3 primer

<400> SEQUENCE: 9
ttccgttgag ccagggtca ccagaatt                                      28

<210> SEQ ID NO 10
<211> LENGTH: 22
<212> TYPE: DNA
<213> ORGANISM: Artificial Sequence
<220> FEATURE:
<223> OTHER INFORMATION: Description of Artificial Sequence:mSlo3 primer

<400> SEQUENCE: 10
tctgctttgt gaagctaaat ct                                           22
```

```
<210> SEQ ID NO 11
<211> LENGTH: 23
<212> TYPE: DNA
<213> ORGANISM: Artificial Sequence
<220> FEATURE:
<223> OTHER INFORMATION: Description of Artificial Sequence:mSlo3 primer

<400> SEQUENCE: 11
tttcaaagcc tctttagcgg taa                                           23

<210> SEQ ID NO 12
<211> LENGTH: 26
<212> TYPE: DNA
<213> ORGANISM: Artificial Sequence
<220> FEATURE:
<223> OTHER INFORMATION: Description of Artificial Sequence:mSlo3 primer

<400> SEQUENCE: 12
ttatgcctgg atctgcactc tacatg                                        26

<210> SEQ ID NO 13
<211> LENGTH: 23
<212> TYPE: DNA
<213> ORGANISM: Artificial Sequence
<220> FEATURE:
<223> OTHER INFORMATION: Description of Artificial Sequence:mSlo3 primer

<400> SEQUENCE: 13
atagtttccg tctactaccg aaa                                           23

<210> SEQ ID NO 14
<211> LENGTH: 24
<212> TYPE: DNA
<213> ORGANISM: Artificial Sequence
<220> FEATURE:
<223> OTHER INFORMATION: Description of Artificial Sequence:hSlo3 primer

<400> SEQUENCE: 14
ggcagcgctc attctttcct cctt                                          24

<210> SEQ ID NO 15
<211> LENGTH: 24
<212> TYPE: DNA
<213> ORGANISM: Artificial Sequence
<220> FEATURE:
<223> OTHER INFORMATION: Description of Artificial Sequence:hSlo3 primer

<400> SEQUENCE: 15
tgcccaaaac ctcaacccaa aata                                          24

<210> SEQ ID NO 16
<211> LENGTH: 1105
<212> TYPE: PRT
<213> ORGANISM: Homo sapiens
<220> FEATURE:
<223> OTHER INFORMATION: human Slo3-1 (hSlo3-1)
<220> FEATURE:
<221> NAME/KEY: VARIANT
<222> LOCATION: (6)
<223> OTHER INFORMATION: polymorphic variant #2 Leu -> Ile
<220> FEATURE:
<221> NAME/KEY: VARIANT
<222> LOCATION: (23)
<223> OTHER INFORMATION: polymorphic variant #1 Ile -> Val
<220> FEATURE:
<221> NAME/KEY: VARIANT
<222> LOCATION: (25)
<223> OTHER INFORMATION: polymorphic variant #3 Ala -> Ser
```

<400> SEQUENCE: 16

```
Met Phe Gln Thr Lys Leu Arg Asn Glu Thr Trp Glu Asp Leu Pro Lys
 1               5                  10                  15
Met Ser Cys Thr Thr Glu Ile Gln Ala Ala Phe Ile Leu Ser Ser Phe
                20                  25                  30
Val Thr Phe Phe Ser Gly Leu Ile Ile Leu Leu Ile Phe Arg Leu Ile
            35                  40                  45
Trp Arg Ser Val Lys Lys Trp Gln Ile Ile Lys Gly Thr Gly Ile Ile
        50                  55                  60
Leu Glu Leu Phe Thr Ser Gly Thr Ile Ala Arg Ser His Val Arg Ser
 65                  70                  75                  80
Leu His Phe Gln Gly Gln Phe Arg Asp His Ile Glu Met Leu Leu Ser
                85                  90                  95
Ala Gln Thr Phe Val Gly Gln Val Leu Val Ile Leu Val Phe Val Leu
            100                 105                 110
Ser Ile Gly Ser Leu Ile Ile Tyr Phe Ile Asn Ser Ala Asp Pro Val
        115                 120                 125
Gly Ser Cys Ser Ser Tyr Glu Asp Lys Thr Ile Pro Ile Asp Leu Val
130                 135                 140
Phe Asn Ala Phe Phe Ser Phe Tyr Phe Gly Leu Arg Phe Met Ala Ala
145                 150                 155                 160
Asp Asp Lys Ile Lys Phe Trp Leu Glu Met Asn Ser Ile Val Asp Ile
                165                 170                 175
Phe Thr Ile Pro Pro Thr Phe Ile Ser Tyr Tyr Leu Lys Ser Asn Trp
            180                 185                 190
Leu Gly Leu Arg Phe Leu Arg Ala Leu Arg Leu Leu Glu Leu Pro Gln
        195                 200                 205
Ile Leu Gln Ile Leu Arg Ala Ile Lys Thr Ser Asn Ser Val Lys Phe
210                 215                 220
Ser Lys Leu Leu Ser Ile Ile Leu Ser Thr Trp Phe Thr Ala Ala Gly
225                 230                 235                 240
Phe Ile His Leu Val Glu Asn Ser Gly Asp Pro Trp Leu Lys Gly Arg
                245                 250                 255
Asn Ser Gln Asn Ile Ser Tyr Phe Glu Ser Ile Tyr Leu Val Met Ala
            260                 265                 270
Thr Thr Ser Thr Val Gly Phe Gly Asp Val Val Ala Lys Thr Ser Leu
        275                 280                 285
Gly Arg Thr Phe Ile Met Phe Phe Thr Leu Gly Ser Leu Ile Leu Phe
290                 295                 300
Ala Asn Tyr Ile Pro Glu Met Val Glu Leu Phe Ala Asn Lys Arg Lys
305                 310                 315                 320
Tyr Thr Ser Ser Tyr Glu Ala Leu Lys Gly Lys Lys Phe Ile Val Val
                325                 330                 335
Cys Gly Asn Ile Thr Val Asp Ser Val Thr Ala Phe Leu Arg Asn Phe
            340                 345                 350
Leu Arg Asp Lys Ser Gly Glu Ile Asn Thr Glu Ile Val Phe Leu Gly
        355                 360                 365
Glu Thr Pro Pro Ser Leu Glu Leu Glu Thr Ile Phe Lys Cys Tyr Leu
370                 375                 380
Ala Tyr Thr Thr Phe Ile Ser Gly Ser Ala Met Lys Trp Glu Asp Leu
385                 390                 395                 400
Arg Arg Val Ala Val Glu Ser Ala Glu Ala Cys Leu Ile Ile Ala Asn
```

-continued

```
                405                 410                 415
Pro Leu Cys Ser Asp Ser His Ala Glu Asp Ile Ser Asn Ile Met Arg
            420                 425                 430
Val Leu Ser Ile Lys Asn Tyr Asp Ser Thr Thr Arg Ile Ile Ile Gln
            435                 440                 445
Ile Leu Gln Ser His Asn Lys Val Tyr Leu Pro Lys Ile Pro Ser Trp
            450                 455                 460
Asn Trp Asp Thr Gly Asp Asn Ile Ile Cys Phe Ala Glu Leu Lys Leu
465                 470                 475                 480
Gly Phe Ile Ala Gln Gly Cys Leu Val Pro Gly Leu Cys Thr Phe Leu
                485                 490                 495
Thr Ser Leu Phe Val Glu Gln Asn Lys Lys Val Met Pro Lys Gln Thr
                500                 505                 510
Trp Lys Lys His Phe Leu Asn Ser Met Lys Asn Lys Ile Leu Thr Gln
            515                 520                 525
Arg Leu Ser Asp Asp Phe Ala Gly Met Ser Phe Pro Glu Val Ala Arg
            530                 535                 540
Leu Cys Phe Leu Lys Met Tyr Leu Leu Leu Ile Ala Ile Glu Tyr Lys
545                 550                 555                 560
Ser Leu Phe Thr Asp Gly Phe Cys Gly Leu Ile Leu Asn Pro Pro Pro
                565                 570                 575
Gln Val Arg Ile Arg Lys Asn Thr Leu Gly Phe Phe Ile Ala Glu Thr
            580                 585                 590
Pro Lys Asp Val Arg Arg Ala Leu Phe Tyr Cys Ser Val Cys His Asp
            595                 600                 605
Asp Val Phe Ile Pro Glu Leu Ile Thr Asn Cys Gly Cys Lys Ser Arg
            610                 615                 620
Ser Arg Gln His Ile Thr Val Pro Ser Val Lys Arg Met Lys Lys Cys
625                 630                 635                 640
Leu Lys Gly Ile Ser Ser Arg Ile Ser Gly Gln Asp Ser Pro Pro Arg
                645                 650                 655
Val Ser Ala Ser Thr Ser Ser Ile Ser Asn Phe Thr Thr Arg Thr Leu
                660                 665                 670
Gln His Asp Val Glu Gln Asp Ser Asp Gln Leu Asp Ser Ser Gly Met
            675                 680                 685
Phe His Trp Cys Lys Pro Thr Ser Leu Asp Lys Val Thr Leu Lys Arg
            690                 695                 700
Thr Gly Lys Ser Lys Tyr Lys Phe Arg Asn His Ile Val Ala Cys Val
705                 710                 715                 720
Phe Gly Asp Ala His Ser Ala Pro Met Gly Leu Arg Asn Phe Val Met
                725                 730                 735
Pro Leu Arg Ala Ser Asn Tyr Thr Arg Lys Glu Leu Lys Asp Ile Val
            740                 745                 750
Phe Ile Gly Ser Leu Asp Tyr Leu Gln Arg Glu Trp Arg Phe Leu Arg
            755                 760                 765
Asn Phe Pro Gln Ile Tyr Ile Leu Pro Gly Cys Ala Leu Tyr Ser Gly
770                 775                 780
Asp Leu His Ala Ala Asn Ile Glu Gln Cys Ser Met Cys Ala Val Leu
785                 790                 795                 800
Ser Pro Pro Pro Gln Pro Ser Ser Asn Gln Thr Leu Val Asp Thr Glu
                805                 810                 815
Ala Ile Met Ala Thr Leu Thr Ile Gly Ser Leu Gln Ile Asp Ser Ser
            820                 825                 830
```

```
Ser Asp Pro Ser Pro Ser Val Ser Glu Glu Thr Pro Gly Tyr Thr Asn
        835                 840                 845

Gly His Asn Glu Lys Ser Asn Cys Arg Lys Val Pro Ile Leu Thr Glu
    850                 855                 860

Leu Lys Asn Pro Ser Asn Ile His Phe Ile Glu Gln Leu Gly Gly Leu
865                 870                 875                 880

Glu Gly Ser Leu Gln Glu Thr Asn Leu His Leu Ser Thr Ala Phe Ser
            885                 890                 895

Thr Gly Thr Val Phe Ser Ser Phe Leu Asp Ser Leu Leu Ala Thr
        900                 905                 910

Ala Phe Tyr Asn Tyr His Val Leu Glu Leu Leu Gln Met Leu Val Thr
    915                 920                 925

Gly Gly Val Ser Ser Gln Leu Glu Gln His Leu Asp Lys Asp Lys Val
    930                 935                 940

Tyr Gly Val Ala Asp Ser Cys Thr Ser Leu Leu Ser Gly Arg Asn Arg
945                 950                 955                 960

Cys Lys Leu Gly Leu Leu Ser Leu His Glu Thr Ile Leu Ser Asp Val
            965                 970                 975

Asn Pro Arg Asn Thr Phe Gly Gln Leu Phe Cys Gly Ser Leu Asp Leu
        980                 985                 990

Phe Gly Ile Leu Cys Val Gly Leu Tyr Arg Ile Ile Asp Glu Glu Glu
    995                 1000                1005

Leu Asn Pro Glu Asn Lys Arg Phe Val Ile Thr Arg Pro Ala Asn Glu
    1010                1015                1020

Phe Lys Leu Leu Pro Ser Asp Leu Val Phe Cys Ala Ile Pro Phe Ser
1025                1030                1035                1040

Thr Ala Cys Tyr Lys Arg Asn Glu Glu Phe Ser Leu Gln Lys Ser Tyr
            1045                1050                1055

Glu Ile Val Asn Lys Ala Ser Gln Thr Thr Glu Asp Thr Phe Arg His
        1060                1065                1070

Lys Leu Ser Ser His Pro Leu Ile Gln Leu Leu Arg His Cys Ile His
        1075                1080                1085

Gln Ser Ile Leu Thr Ser Arg Glu Leu Thr Pro Ser Leu Phe Leu Ser
    1090                1095                1100

Lys
1105

<210> SEQ ID NO 17
<211> LENGTH: 3319
<212> TYPE: DNA
<213> ORGANISM: Homo sapiens
<220> FEATURE:
<223> OTHER INFORMATION: human Slo3-1 (hSlo3-1)

<400> SEQUENCE: 17
atgtttcaga ctaagctacg aaatgaaact tgggaagact tgccaaaaat gtcctgcaca      60
actgagatcc aagcagcatt cattctctct tcctttgtga ccttcttcag tggactcatc     120
atcctgttga tcttcaggct gatctggaga tctgttaaaa aatggcaaat catcaaggga     180
acaggaatta tcttggaact gttcacatca ggtaccatcg ctaggagcca tgtaagaagc     240
ctccacttcc agggacaatt tcgtgatcat atagaaatgt tgctttcagc ccagaccttt     300
gtggggcaag tgttggtgat ccttgtcttt gtactaagca ttgggtctct tataatctat     360
ttcatcaatt ctgctgaccc tgttggaagc tgttcatcat atgaagacaa aaccattcct     420
```

```
attgatttgg ttttcaatgc tttctttagt ttctattttg gattgaggtt tatggcagct    480
gatgacaaga tcaagttctg gctggagatg aattcaatcg tagacatctt taccatccca    540
ccaaccttta tttcttatta tttgaagagc aattggctag gtttaaggtt cctaagagcc    600
ttgcgcctgc tagaactccc tcaaatcttg caaattctac gagccatcaa gaccagtaac    660
tcagtgaagt tttccaaact gctgtcaata attctcagta cctggttcac agctgcggga    720
ttcattcacc tggtggaaaa ttctggtgat ccctggctca aggtagaaa ttcacagaat    780 atatcatatt ttgagtcaat ttacctggtc atggcaacaa cgtcaaccgt tggatttgga    840
gatgtggtag ccaagacatc cttaggacgg accttcatca tgttcttcac actggggagt    900
ttgatattat ttgcgaacta tatacctgaa atggtggaac tgtttgctaa caagaggaaa    960
tacaccagtt cmtatgaagc actcaaagga agaagtttaa ttgtggtctg tggaaacatc   1020
actgtggaca gtgtgaccgc tttcctgagg aatttcctcc gcgacaagtc aggagagatc   1080
aacactgaaa ttgttttcct gggagaaacc cctccttctt tggaacttga aaccatattt   1140
aaatgctact tggcctacac aacgttcatt tctggatctg caatgaagtg ggaggatctg   1200
aggcgagttg cggtggaatc tgcagaggca tgcctgatta tagccaatcc tttgtgcagt   1260
gattcccatg ctgaagatat ttccaacatt atgagggtgc tctctatcaa gaactatgat   1320
tctaccacca gaatcatcat acagatactg caatcccata caaggtttta tctgccaaag   1380
attcccagct ggaactggga caccggagac aacatcatct gctttgctga attaaaactt   1440
ggatttatcg cccaaggctg tttggtgcca ggcttgtgta ccttcctaac atctctattt   1500
gtggagcaaa acaaaaaggt tatgcctaaa cagacctgga agaaacactt cttgaatagc   1560
atgaaaaaca aaattctgac ccaacgtctc tctgatgact ttgctggaat gagctttcct   1620
gaagttgccc ggctctgctt tctgaagatg tacctcctgt tgatagccat cgaatacaag   1680 tccctctttta cggatggttt ctgtggtctg atactaaatc cacctccaca agtgaggata   1740
cgtaagaaca cattagggtt cttttattgct gaaactccaa aggacgtcag aagagccttg   1800
ttttactgtt cagtctgtca tgatgatgtg ttcattcctg agctaattac aaactgtggc   1860
tgcaaaagca gaagccggca gcacatcaca gtgccatcgg taaagagaat gaaaaaatgt   1920
ctgaagggaa tctcctctcg tatatcaggg caggattctc cgccaagggt atctgcaagc   1980
acttcgagca tatcaaactt caccaccagg actcttcaac atgatgtaga acaagattct   2040
gaccagcttg atagcagtgg gatgtttcac tggtgcaaac caacctcttt ggacaaggtg   2100
actctgaaac gaactggcaa gtcaaagtat aagtttcgga accatattgt agcatgtgta   2160
tttggagatg cccactcagc cccgatgggg cttcggaact tgtaatgcc cttgagagcc   2220 agcaactata ccaggaagga gctgaaggac atagtgttca ttgggtctct ggactatcta   2280
cagagagaat ggcgatttct ccggaatttt ccccagatat acattctgcc tggatgtgca   2340
ctttattctg gagacctcca tgcggccaac atagagcaat gctccatgtg tgctgtcttg   2400 tccccccac cccagccatc aagcaaccag actttggtag acacagaagc catcatggca   2460
accctcacca tcggatcctt gcaaattgac tcctcctctg acccgtcacc ctcagtgtca   2520
gaggagactc caggttacac aaatggacat aatgagaaat caaactgccg aaaagtccct   2580
atccttactg aactgaaaaa tccttccaac attcacttta ttgaacagct tggtggactg   2640
gaagggtccc tccaagaaac aaatctgcat ctcagcactg ccttttctac gggcactgtt   2700
ttttccagca gcttcttgga ttctctgctg gccacggcct tctacaatta tcatgtcctg   2760
gaattgcttc agatgctggt gacaggagga gtaagttctc agctggaaca acatttagat   2820
```

-continued

| | |
|---|---|
| aaggataaag tctatggtgt ggcagatagc tgcacgtcgc tcttgtctgg aagaaaccgg | 2880 |
| tgtaagctgg ggcttctgtc cttacacgaa accattttat cagacgttaa tccaagaaac | 2940 |
| acctttggac aactgttctg tggctcatta gatcttttg gaatcctgtg tgttggctta | 3000 |
| taccgaataa ttgatgaaga ggagctcaac ccagaaaaca aaggtttgt gatcacccgg | 3060 |
| ccagccaatg agttcaagct gctgccttca gatcttgtgt tttgtgccat acccttcagc | 3120 |
| actgcttgtt ataaaaggaa tgaagagttc tcattgcaaa agtcatatga aattgtaaat | 3180 |
| aaagcatcac agacaacaga ggacacattc agacacaaat tgtcctccca cccattgatt | 3240 |
| cagttactga gacattgtat tcaccagtct attcttacca gccgagaact aactccctct | 3300 |
| cttttcctaa gcaaatagg | 3319 |

<210> SEQ ID NO 18
<211> LENGTH: 1081
<212> TYPE: PRT
<213> ORGANISM: Homo sapiens
<220> FEATURE:
<223> OTHER INFORMATION: human hSlo3-2 (hSlo3-2)

<400> SEQUENCE: 18

```
Met Phe Gln Thr Lys Leu Arg Asn Glu Thr Trp Glu Asp Leu Pro Lys
  1               5                  10                  15
Met Ser Cys Thr Thr Glu Ile Gln Ala Ala Phe Ile Leu Ser Ser Phe
                 20                  25                  30
Val Thr Phe Phe Ser Gly Leu Ile Ile Leu Leu Ile Phe Arg Leu Ile
             35                  40                  45
Trp Arg Ser Val Lys Lys Trp Gln Ile Ile Lys Gly Thr Gly Ile Ile
         50                  55                  60
Leu Glu Leu Phe Thr Ser Gly Thr Ile Ala Arg Ser His Val Arg Ser
 65                  70                  75                  80
Leu His Phe Gln Gly Gln Phe Arg Asp His Ile Glu Met Leu Leu Ser
                 85                  90                  95
Ala Gln Thr Phe Val Gly Gln Val Leu Val Ile Leu Val Phe Val Leu
            100                 105                 110
Ser Ile Gly Ser Leu Ile Ile Tyr Phe Ile Asn Ser Ala Asp Pro Val
        115                 120                 125
Gly Ser Cys Ser Ser Tyr Glu Asp Lys Thr Ile Pro Ile Asp Leu Val
    130                 135                 140
Phe Asn Ala Phe Phe Ser Phe Tyr Phe Gly Leu Arg Phe Met Ala Ala
145                 150                 155                 160
Asp Asp Lys Ile Lys Phe Trp Leu Glu Met Asn Ser Ile Val Asp Ile
                165                 170                 175
Phe Thr Ile Pro Pro Thr Phe Ile Ser Tyr Tyr Leu Lys Ser Asn Trp
            180                 185                 190
Leu Gly Leu Arg Phe Leu Arg Ala Leu Arg Leu Leu Glu Leu Pro Gln
        195                 200                 205
Ile Leu Gln Ile Leu Arg Ala Ile Lys Thr Ser Asn Ser Val Lys Phe
    210                 215                 220
Ser Lys Leu Leu Ser Ile Ile Leu Ser Thr Trp Phe Thr Ala Ala Gly
225                 230                 235                 240
Phe Ile His Leu Val Glu Asn Ser Gly Asp Pro Trp Leu Lys Gly Arg
                245                 250                 255
Asn Ser Gln Asn Ile Ser Tyr Phe Glu Ser Ile Tyr Leu Val Met Ala
            260                 265                 270
```

```
Thr Thr Ser Thr Val Gly Phe Gly Asp Val Val Ala Lys Thr Ser Leu
        275                 280                 285

Gly Arg Thr Phe Ile Met Phe Phe Thr Leu Gly Ser Leu Ile Leu Phe
    290                 295                 300

Ala Asn Tyr Ile Pro Glu Met Val Glu Leu Phe Ala Asn Lys Arg Lys
305                 310                 315                 320

Tyr Thr Ser Ser Tyr Glu Ala Leu Lys Gly Lys Lys Phe Ile Val Val
                325                 330                 335

Cys Gly Asn Ile Thr Val Asp Ser Val Thr Ala Phe Leu Arg Asn Phe
            340                 345                 350

Leu Arg Asp Lys Ser Gly Glu Ile Asn Thr Glu Ile Val Phe Leu Gly
        355                 360                 365

Glu Thr Pro Pro Ser Leu Glu Leu Glu Thr Ile Phe Lys Cys Tyr Leu
    370                 375                 380

Ala Tyr Thr Thr Phe Ile Ser Gly Ser Ala Met Lys Trp Glu Asp Leu
385                 390                 395                 400

Arg Arg Val Ala Val Glu Ser Ala Glu Ala Cys Leu Ile Ile Ala Asn
                405                 410                 415

Pro Leu Cys Ser Asp Ser His Ala Glu Asp Ile Ser Asn Ile Met Arg
            420                 425                 430

Val Leu Ser Ile Lys Asn Tyr Asp Ser Thr Thr Arg Ile Ile Ile Gln
        435                 440                 445

Ile Leu Gln Ser His Asn Lys Val Tyr Leu Pro Lys Ile Pro Ser Trp
    450                 455                 460

Asn Trp Asp Thr Gly Asp Asn Ile Ile Cys Phe Ala Glu Leu Lys Leu
465                 470                 475                 480

Gly Phe Ile Ala Gln Gly Cys Leu Val Pro Gly Leu Cys Thr Phe Leu
                485                 490                 495

Thr Ser Leu Phe Val Glu Gln Asn Lys Lys Val Met Pro Lys Gln Thr
            500                 505                 510

Trp Lys Lys His Phe Leu Asn Ser Met Lys Asn Lys Ile Leu Thr Gln
        515                 520                 525

Arg Leu Ser Asp Asp Phe Ala Gly Met Ser Phe Pro Glu Val Ala Arg
    530                 535                 540

Gly Leu Ile Leu Asn Pro Pro Gln Val Arg Ile Arg Lys Asn Thr
545                 550                 555                 560

Leu Gly Phe Phe Ile Ala Glu Thr Pro Lys Asp Val Arg Arg Ala Leu
                565                 570                 575

Phe Tyr Cys Ser Val Cys His Asp Asp Val Phe Ile Pro Glu Leu Ile
            580                 585                 590

Thr Asn Cys Gly Cys Lys Ser Arg Ser Arg Gln His Ile Thr Val Pro
        595                 600                 605

Ser Val Lys Arg Met Lys Lys Cys Leu Lys Gly Ile Ser Ser Arg Ile
    610                 615                 620

Ser Gly Gln Asp Ser Pro Pro Arg Val Ser Ala Ser Thr Ser Ser Ile
625                 630                 635                 640

Ser Asn Phe Thr Thr Arg Thr Leu Gln His Asp Val Glu Gln Asp Ser
                645                 650                 655

Asp Gln Leu Asp Ser Ser Gly Met Phe His Trp Cys Lys Pro Thr Ser
            660                 665                 670

Leu Asp Lys Val Thr Leu Lys Arg Thr Gly Lys Ser Lys Tyr Lys Phe
        675                 680                 685
```

-continued

```
Arg Asn His Ile Val Ala Cys Val Phe Gly Asp Ala His Ser Ala Pro
    690                 695                 700
Met Gly Leu Arg Asn Phe Val Met Pro Leu Arg Ala Ser Asn Tyr Thr
705                 710                 715                 720
Arg Lys Glu Leu Lys Asp Ile Val Phe Ile Gly Ser Leu Asp Tyr Leu
                725                 730                 735
Gln Arg Glu Trp Arg Phe Leu Arg Asn Phe Pro Gln Ile Tyr Ile Leu
            740                 745                 750
Pro Gly Cys Ala Leu Tyr Ser Gly Asp Leu His Ala Ala Asn Ile Glu
        755                 760                 765
Gln Cys Ser Met Cys Ala Val Leu Ser Pro Pro Gln Pro Ser Ser
    770                 775                 780
Asn Gln Thr Leu Val Asp Thr Glu Ala Ile Met Ala Thr Leu Thr Ile
785                 790                 795                 800
Gly Ser Leu Gln Ile Asp Ser Ser Asp Pro Ser Pro Ser Val Ser
                805                 810                 815
Glu Glu Thr Pro Gly Tyr Thr Asn Gly His Asn Glu Lys Ser Asn Cys
            820                 825                 830
Arg Lys Val Pro Ile Leu Thr Glu Leu Lys Asn Pro Ser Asn Ile His
        835                 840                 845
Phe Ile Glu Gln Leu Gly Gly Leu Gly Ser Leu Gln Glu Thr Asn
    850                 855                 860
Leu His Leu Ser Thr Ala Phe Ser Thr Gly Thr Val Phe Ser Ser
865                 870                 875                 880
Phe Leu Asp Ser Leu Leu Ala Thr Ala Phe Tyr Asn Tyr His Val Leu
                885                 890                 895
Glu Leu Leu Gln Met Leu Val Thr Gly Gly Val Ser Ser Gln Leu Glu
            900                 905                 910
Gln His Leu Asp Lys Asp Lys Val Tyr Gly Val Ala Asp Ser Cys Thr
        915                 920                 925
Ser Leu Leu Ser Gly Arg Asn Arg Cys Lys Leu Gly Leu Leu Ser Leu
    930                 935                 940
His Glu Thr Ile Leu Ser Asp Val Asn Pro Arg Asn Thr Phe Gly Gln
945                 950                 955                 960
Leu Phe Cys Gly Ser Leu Asp Leu Phe Gly Ile Leu Cys Val Gly Leu
                965                 970                 975
Tyr Arg Ile Ile Asp Glu Glu Leu Asn Pro Glu Asn Lys Arg Phe
            980                 985                 990
Val Ile Thr Arg Pro Ala Asn Glu Phe Lys Leu Leu Pro Ser Asp Leu
        995                 1000                1005
Val Phe Cys Ala Ile Pro Phe Ser Thr Ala Cys Tyr Lys Arg Asn Glu
    1010                1015                1020
Glu Phe Ser Leu Gln Lys Ser Tyr Glu Ile Val Asn Lys Ala Ser Gln
1025                1030                1035                1040
Thr Thr Glu Asp Thr Phe Arg His Lys Leu Ser Ser His Pro Leu Ile
                1045                1050                1055
Gln Leu Leu Arg His Cys Ile His Gln Ser Ile Leu Thr Ser Arg Glu
            1060                1065                1070
Leu Thr Pro Ser Leu Phe Leu Ser Lys
        1075                1080

<210> SEQ ID NO 19
<211> LENGTH: 3247
<212> TYPE: DNA
```

<213> ORGANISM: Homo sapiens
<220> FEATURE:
<223> OTHER INFORMATION: human Slo3-2 (hSlo3-2)

<400> SEQUENCE: 19

| | | | | | |
|---|---|---|---|---|---|
| atgtttcaga | ctaagctacg | aaatgaaact | tgggaagact | tgccaaaaat | gtcctgcaca | 60 |
| actgagatcc | aagcagcatt | cattctctct | tcctttgtga | ccttcttcag | tggactcatc | 120 |
| atcctgttga | tcttcaggct | gatctggaga | tctgttaaaa | aatggcaaat | catcaaggga | 180 |
| acaggaatta | tcttggaact | gttcacatca | ggtaccatcg | ctaggagcca | tgtaagaagc | 240 |
| ctccacttcc | agggacaatt | tcgtgatcat | atagaaatgt | tgctttcagc | ccagaccttt | 300 |
| gtggggcaag | tgttggtgat | ccttgtcttt | gtactaagca | ttgggtctct | tataatctat | 360 |
| ttcatcaatt | ctgctgaccc | tgttggaagc | tgttcatcat | atgaagacaa | aaccattcct | 420 |
| attgatttgg | ttttcaatgc | tttctttagt | ttctattttg | gattgaggtt | tatggcagct | 480 |
| gatgacaaga | tcaagttctg | gctggagatg | aattcaatcg | tagacatctt | taccatccca | 540 |
| ccaaccttta | tttcttatta | tttgaagagc | aattggctag | gtttaaggtt | cctaagagcc | 600 |
| ttgcgcctgc | tagaactccc | tcaaatcttg | caaattctac | gagccatcaa | gaccagtaac | 660 |
| tcagtgaagt | tttccaaact | gctgtcaata | attctcagta | cctggttcac | agctgcggga | 720 |
| ttcattcacc | tggtggaaaa | ttctggtgat | ccctggctca | aagtagaaa | ttcacagaat | 780 |
| atatcatatt | ttgagtcaat | ttacctggtc | atggcaacaa | cgtcaaccgt | ggatttgga | 840 |
| gatgtggtag | ccaagacatc | cttaggacgg | accttcatca | tgttcttcac | actgggagt | 900 |
| ttgatattat | ttgcgaacta | tatacctgaa | atggtggaac | tgtttgctaa | caagaggaaa | 960 |
| tacaccagtt | cmtatgaagc | actcaaagga | agaagtttta | ttgtggtctg | tggaaacatc | 1020 |
| actgtggaca | gtgtgaccgc | tttcctgagg | aatttcctcc | gcgacaagtc | aggagagatc | 1080 |
| aacactgaaa | ttgttttcct | gggagaaaacc | cctccttctt | tggaacttga | accatatt | 1140 |
| aaatgctact | tggcctacac | aacgttcatt | tctggatctg | caatgaagtg | ggaggatctg | 1200 |
| aggcgagttg | cggtggaatc | tgcagaggca | tgcctgatta | tagccaatcc | tttgtgcagt | 1260 |
| gattcccatg | ctgaagatat | tccaacatt | atgagggtgc | tctctatcaa | gaactatgat | 1320 |
| tctaccacca | gaatcatcat | acagatactg | caatccccata | acaaggttta | tctgccaaag | 1380 |
| attcccagct | ggaactggga | caccggagac | aacatcatct | gctttgctga | attaaaactt | 1440 |
| ggatttatcg | cccaaggctg | tttggtgcca | ggcttgtgta | ccttcctaac | atctctattt | 1500 |
| gtggagcaaa | acaaaaaggt | tatgcctaaa | cagacctgga | agaaacactt | cttgaatagc | 1560 |
| atgaaaaaca | aaattctgac | ccaacgtctc | tctgatgact | ttgctggaat | gagctttcct | 1620 |
| gaagttgccc | gtggtctgat | actaaatcca | cctccacaag | tgaggatacg | taagaacaca | 1680 |
| ttagggttct | ttattgctga | aactccaaag | gacgtcagaa | gagccttgtt | ttactgttca | 1740 |
| gtctgtcatg | atgatgtgtt | cattcctgag | ctaattacaa | actgtggctg | caaaagcaga | 1800 |
| agccggcagc | acatcacagt | gccatcggta | agagaatga | aaaatgtct | gaagggaatc | 1860 |
| tcctctcgta | tatcagggca | ggattctccg | ccaagggtat | ctgcaagcac | ttcgagcata | 1920 |
| tcaaacttca | ccaccaggac | tcttcaacat | gatgtagaac | aagattctga | ccagcttgat | 1980 |
| agcagtggga | tgtttcactg | gtgcaaacca | acctctttgg | acaaggtgac | tctgaaacga | 2040 |
| actggcaagt | caaagtataa | gtttcggaac | catattgtag | catgtgtatt | tggagatgcc | 2100 |
| cactcagccc | cgatggggct | tcggaacttt | gtaatgccct | tgagagccag | caactatacc | 2160 |
| aggaaggagc | tgaaggacat | agtgttcatt | gggtctctgg | actatctaca | gagagaatgg | 2220 |

-continued

```
cgatttctcc ggaatttttcc ccagatatac attctgcctg gatgtgcact ttattctgga    2280
gacctccatg cggccaacat agagcaatgc tccatgtgtg ctgtcttgtc ccccccaccc    2340
cagccatcaa gcaaccagac tttggtagac acagaagcca tcatggcaac cctcaccatc    2400
ggatccttgc aaattgactc ctcctctgac ccgtcaccct cagtgtcaga ggagactcca    2460
ggttacacaa atggacataa tgagaaatca aactgccgaa aagtccctat ccttactgaa    2520
ctgaaaaatc cttccaacat tcactttatt gaacagcttg gtggactgga agggtccctc    2580
caagaaacaa atctgcatct cagcactgcc ttttctacgg gcactgtttt ttccagcagc    2640
ttcttggatt ctctgctggc cacggccttc tacaattatc atgtcctgga attgcttcag    2700
atgctggtga caggaggagt aagttctcag ctggaacaac atttagataa ggataaagtc    2760
tatggtgtgg cagatagctg cacgtcgctc ttgtctggaa gaaaccggtg taagctgggg    2820
cttctgtcct tacacgaaac catttttatca gacgttaatc caagaaacac ctttggacaa    2880
ctgttctgtg gctcattaga tcttttttgga atcctgtgtg ttggcttata ccgaataatt    2940
gatgaagagg agctcaaccc agaaaacaaa aggtttgtga tcacccggcc agccaatgag    3000
ttcaagctgc tgccttcaga tcttgtgttt tgtgccatac ccttcagcac tgcttgttat    3060
aaaaggaatg aagagttctc attgcaaaag tcatatgaaa ttgtaaataa agcatcacag    3120
acaacagagg acacattcag acacaaattg tcctcccacc cattgattca gttactgaga    3180
cattgtattc accagtctat tcttaccagc cgagaactaa ctccctctct tttcctaagc    3240
aaatagt                                                               3247
```

<210> SEQ ID NO 20
<211> LENGTH: 1134
<212> TYPE: PRT
<213> ORGANISM: Mus musculus
<220> FEATURE:
<223> OTHER INFORMATION: mouse Slo3 (mSlo3)

<400> SEQUENCE: 20

```
Met Ser Gln Thr Leu Leu Asp Ser Leu Asn Gln Lys Glu Leu Thr Glu
 1               5                  10                  15

Thr Ser Cys Thr Ile Glu Ile Gln Ala Ala Phe Ile Leu Ser Ser Leu
             20                  25                  30

Ala Thr Phe Phe Gly Gly Leu Ile Ile Leu Phe Leu Phe Arg Ile Ala
         35                  40                  45

Leu Lys Ser Ser Arg Ser Trp Lys Tyr Val Lys Gly Pro Arg Gly Leu
     50                  55                  60

Leu Glu Leu Phe Ser Ser Arg Arg Ile Glu Ala Asn Pro Leu Arg Lys
 65                  70                  75                  80

Leu Tyr Phe His Gly Val Phe Arg Gln Arg Ile Glu Met Leu Leu Ser
                 85                  90                  95

Ala Gln Thr Val Val Gly Gln Val Leu Val Ile Leu Val Phe Val Leu
            100                 105                 110

Ser Ile Gly Ser Leu Val Ile Tyr Phe Ile Asn Ser Met Asp Pro Val
        115                 120                 125

Arg Arg Cys Ser Ser Tyr Glu Asp Lys Ile Val His Gly Asp Leu Ser
    130                 135                 140

Phe Asn Ala Phe Phe Ser Phe Tyr Phe Gly Leu Arg Phe Trp Ala Ala
145                 150                 155                 160

Glu Asp Lys Ile Lys Phe Trp Leu Glu Met Asn Ser Ile Val Asp Ile
                165                 170                 175
```

-continued

```
Phe Thr Ile Pro Pro Thr Phe Ile Ser Tyr Tyr Leu Lys Ser Asn Trp
            180                 185                 190

Leu Gly Leu Arg Phe Leu Arg Ala Leu Arg Leu Leu Glu Leu Pro Lys
        195                 200                 205

Ile Leu Gln Ile Leu Gln Val Ile Lys Thr Ser Asn Ser Val Lys Leu
        210                 215                 220

Ser Lys Leu Leu Ser Ile Val Ile Ser Thr Trp Phe Thr Ala Ala Gly
225                 230                 235                 240

Phe Leu His Leu Val Glu Asn Ser Gly Asp Pro Trp Leu Asn Gly Arg
                245                 250                 255

Asn Ser Gln Thr Met Ser Tyr Phe Glu Ser Ile Tyr Leu Val Thr Ala
            260                 265                 270

Thr Met Ser Thr Val Gly Phe Gly Asp Val Val Ala Lys Thr Ser Leu
        275                 280                 285

Gly Arg Ile Phe Ile Val Phe Phe Thr Leu Gly Ser Leu Ile Leu Phe
    290                 295                 300

Ala Asn Tyr Ile Pro Glu Met Val Glu Leu Phe Ser Thr Arg Lys Lys
305                 310                 315                 320

Tyr Thr Lys Pro Tyr Glu Ala Val Lys Gly Lys Lys Phe Ile Val Val
                325                 330                 335

Cys Gly Asn Ile Thr Val Asp Ser Val Thr Ala Phe Leu Arg Asn Phe
            340                 345                 350

Leu His Trp Lys Ser Gly Glu Ile Asn Ile Glu Ile Val Phe Leu Gly
        355                 360                 365

Glu Thr Leu Pro Cys Leu Glu Leu Glu Thr Leu Leu Lys Cys His Thr
    370                 375                 380

Ser Cys Thr Asn Phe Val Cys Gly Thr Ala Leu Lys Phe Glu Asp Leu
385                 390                 395                 400

Lys Arg Val Ala Val Glu Asn Ser Glu Ala Cys Leu Ile Leu Ala Asn
                405                 410                 415

His Phe Cys Ser Asp Leu His Asp Glu Asp Asn Ser Asn Ile Met Arg
            420                 425                 430

Val Leu Ser Ile Lys Asn Tyr Tyr Pro Gln Thr Arg Val Ile Ile Gln
        435                 440                 445

Ile Leu Gln Ser Gln Asn Lys Val Phe Leu Ser Lys Ile Pro Asn Trp
    450                 455                 460

Asp Trp Ser Ala Gly Asp Asn Ile Leu Cys Phe Ala Glu Leu Lys Leu
465                 470                 475                 480

Gly Phe Ile Ala Gln Gly Cys Leu Val Pro Gly Leu Cys Thr Phe Leu
                485                 490                 495

Thr Thr Leu Phe Ile Glu Gln Asn Gln Lys Val Phe Pro Lys His Pro
            500                 505                 510

Trp Gln Lys His Phe Leu Asn Gly Leu Lys Asn Lys Ile Leu Thr Gln
        515                 520                 525

Arg Leu Ser Asn Asp Phe Val Gly Met Thr Phe Pro Gln Val Ser Arg
    530                 535                 540

Leu Cys Phe Val Lys Leu Asn Leu Met Leu Ile Ala Ile Gln His Lys
545                 550                 555                 560

Pro Phe Phe His Ser Cys Cys Thr Leu Ile Leu Asn Pro Ser Ser Gln
                565                 570                 575

Val Arg Leu Asn Lys Asp Thr Leu Gly Phe Phe Ile Ala Asp Ser Ser
            580                 585                 590
```

-continued

```
Lys Ala Val Lys Arg Ala Phe Phe Tyr Cys Ser Asn Cys His Ser Asp
        595                 600                 605
Val Cys Asn Pro Glu Leu Ile Gly Lys Cys Asn Cys Lys Ile Lys Ser
    610                 615                 620
Arg Gln Gln Leu Ile Ala Pro Thr Ile Met Val Met Lys Ser Ser Leu
625                 630                 635                 640
Thr Asp Phe Thr Thr Ser Ser His Ile His Ala Ser Met Ser Thr Glu
                645                 650                 655
Ile His Thr Cys Phe Ser Arg Glu Gln Pro Ser Leu Ile Thr Ile Thr
            660                 665                 670
Thr Asn Arg Pro Thr Thr Asn Asp Thr Val Asp Asp Thr Asp Met Leu
        675                 680                 685
Asp Ser Ser Gly Met Phe His Trp Cys Arg Ala Met Pro Leu Asp Lys
    690                 695                 700
Val Val Leu Lys Arg Ser Glu Lys Ala Lys His Glu Phe Gln Asn His
705                 710                 715                 720
Ile Val Val Cys Val Phe Gly Asp Ala Gln Cys Thr Leu Val Gly Leu
                725                 730                 735
Arg Asn Phe Val Met Pro Leu Arg Ala Ser Asn Tyr Thr Arg Gln Glu
            740                 745                 750
Leu Lys Asp Ile Val Phe Ile Gly Ser Leu Glu Tyr Phe Gln Arg Glu
        755                 760                 765
Trp Arg Phe Leu Arg Asn Phe Pro Lys Ile His Ile Met Pro Gly Ser
    770                 775                 780
Ala Leu Tyr Met Gly Asp Leu Ile Ala Val Asn Val Glu Gln Cys Ser
785                 790                 795                 800
Met Cys Val Ile Leu Ala Thr Pro Tyr Lys Ala Leu Ser Ser Gln Ile
                805                 810                 815
Leu Val Asp Thr Glu Ala Ile Met Ala Thr Leu Asn Ile Gln Ser Leu
            820                 825                 830
Arg Ile Thr Ser Pro Thr Pro Gly Ser Ser Lys Ser Glu Val Lys Pro
        835                 840                 845
Ser Ser Ala Phe Asp Ser Lys Glu Arg Lys Gln Arg Tyr Lys Gln Ile
    850                 855                 860
Pro Ile Leu Thr Glu Leu Lys Asn Pro Ser Asn Ile His Phe Ile Glu
865                 870                 875                 880
Gln Met Gly Gly Leu Asp Gly Met Leu Lys Gly Thr Ser Leu His Leu
                885                 890                 895
Ser Thr Ser Phe Ser Thr Gly Ala Val Phe Ser Asp Thr Phe Leu Asp
            900                 905                 910
Ser Leu Leu Ala Thr Ser Phe Tyr Asn Tyr His Val Val Glu Leu Leu
        915                 920                 925
Gln Met Leu Val Thr Gly Gly Ile Ser Ser Glu Met Glu His Tyr Leu
    930                 935                 940
Val Lys Glu Lys Pro Tyr Lys Thr Thr Asp Asp Tyr Glu Ala Ile Lys
945                 950                 955                 960
Ser Gly Arg Thr Arg Cys Lys Leu Gly Leu Ser Leu Asp Gln Thr
                965                 970                 975
Val Leu Ser Gly Ile Asn Pro Arg Lys Thr Phe Gly Gln Leu Phe Cys
            980                 985                 990
Gly Ser Leu Asp Asn Phe Gly Ile Leu Cys Val Gly Leu Tyr Arg Met
        995                 1000                1005
Ile Asp Glu Glu Glu Pro Ser Gln Glu His Lys Arg Phe Val Ile Thr
```

-continued

```
              1010                1015                1020
Arg Pro Ser Asn Glu Cys His Leu Leu Pro Ser Asp Leu Val Phe Cys
1025                1030                1035                1040

Ala Ile Pro Phe Asn Thr Thr Cys Gly Lys Ser Asp Ser Ser Pro Phe
              1045                1050                1055

Asn Phe Arg Leu Lys Thr Thr Leu Gln Thr Arg Arg His Trp Pro
              1060                1065                1070

Arg Gly Arg Ile Ser Ser Ile Arg Thr Met Pro Thr Ser Pro Thr Ile
              1075                1080                1085

Phe Thr Gln Ser Thr Thr Arg Glu Arg Gly Leu Ser Thr Thr Thr
              1090                1095                1100

Pro Glu Ser Ile Leu Trp Thr Arg Gln Leu Phe Cys Gly Ser Leu Asp
1105                1110                1115                1120

Asn Phe Gly Ile Leu Cys Val Gly Leu Tyr Arg Met Ile Asp
              1125                1130
```

<210> SEQ ID NO 21
<211> LENGTH: 1236
<212> TYPE: PRT
<213> ORGANISM: Mus musculus
<220> FEATURE:
<223> OTHER INFORMATION: mouse Slo1 (mSlo1)

<400> SEQUENCE: 21

```
Met Asp Ala Leu Ile Ile Pro Val Thr Met Glu Val Pro Cys Asp Ser
  1               5                  10                  15

Arg Gly Gln Arg Met Trp Trp Ala Phe Leu Ala Ser Ser Met Val Thr
                 20                  25                  30

Phe Phe Gly Gly Leu Phe Ile Ile Leu Leu Trp Arg Thr Leu Lys Tyr
             35                  40                  45

Leu Trp Thr Val Cys Cys His Cys Gly Gly Lys Thr Lys Glu Ala Gln
         50                  55                  60

Lys Ile Asn Asn Gly Ser Ser Gln Ala Asp Gly Thr Leu Lys Pro Val
 65                  70                  75                  80

Asp Glu Lys Glu Glu Val Val Ala Ala Glu Val Gly Trp Met Thr Ser
                 85                  90                  95

Val Lys Asp Trp Ala Gly Val Met Ile Ser Ala Gln Thr Leu Thr Gly
                100                 105                 110

Arg Val Leu Val Val Leu Val Phe Ala Leu Ser Ile Gly Ala Leu Val
            115                 120                 125

Ile Tyr Phe Ile Asp Ser Ser Asn Pro Ile Glu Ser Cys Gln Asn Phe
        130                 135                 140

Tyr Lys Asp Phe Thr Leu Gln Ile Asp Met Ala Phe Asn Val Phe Phe
145                 150                 155                 160

Leu Leu Tyr Phe Gly Leu Arg Phe Ile Ala Ala Asn Asp Lys Leu Trp
                165                 170                 175

Phe Trp Leu Glu Val Asn Ser Val Val Asp Phe Phe Thr Val Pro Pro
            180                 185                 190

Val Phe Val Ser Val Tyr Leu Asn Arg Ser Trp Leu Gly Leu Arg Phe
        195                 200                 205

Leu Arg Ala Leu Arg Leu Ile Gln Phe Ser Glu Ile Leu Gln Phe Leu
    210                 215                 220

Asn Ile Leu Lys Thr Ser Asn Ser Ile Lys Leu Val Asn Leu Leu Ser
225                 230                 235                 240

Ile Phe Ile Ser Thr Trp Leu Thr Ala Ala Gly Phe Ile His Leu Val
```

-continued

```
                    245                 250                 255
Glu Asn Ser Gly Asp Pro Trp Glu Asn Phe Gln Asn Asn Gln Ala Leu
                260                 265                 270
Thr Tyr Trp Glu Cys Val Tyr Leu Leu Met Val Thr Met Ser Thr Val
            275                 280                 285
Gly Tyr Gly Asp Val Tyr Ala Lys Thr Thr Leu Gly Arg Leu Phe Met
        290                 295                 300
Val Phe Phe Ile Leu Gly Gly Leu Ala Met Phe Ala Ser Tyr Val Pro
305                 310                 315                 320
Glu Ile Ile Glu Leu Ile Gly Asn Arg Lys Lys Tyr Gly Gly Ser Tyr
                325                 330                 335
Ser Ala Val Ser Gly Arg Lys His Ile Val Val Cys Gly His Ile Thr
                340                 345                 350
Leu Glu Ser Val Ser Asn Phe Leu Lys Asp Phe Leu His Lys Asp Arg
                355                 360                 365
Asp Asp Val Asn Val Glu Ile Val Phe Leu His Asn Ile Ser Pro Asn
            370                 375                 380
Leu Glu Leu Glu Ala Leu Phe Lys Arg His Phe Thr Gln Val Glu Phe
385                 390                 395                 400
Tyr Gln Gly Ser Val Leu Asn Pro His Asp Leu Ala Arg Val Lys Ile
                405                 410                 415
Glu Ser Ala Asp Ala Cys Leu Ile Leu Ala Asn Lys Tyr Cys Ala Asp
                420                 425                 430
Pro Asp Ala Glu Asp Ala Ser Asn Ile Met Arg Val Ile Ser Ile Lys
            435                 440                 445
Asn Tyr His Pro Lys Ile Arg Ile Ile Thr Gln Met Leu Gln Tyr His
465                 470                 475                 480
Asn Lys Ala His Leu Leu Asn Ile Pro Ser Trp Asn Trp Lys Glu Gly
465                 470                 475                 480
Asp Asp Ala Ile Cys Leu Ala Glu Leu Lys Leu Gly Phe Ile Ala Gln
                485                 490                 495
Ser Cys Leu Ala Gln Gly Leu Ser Thr Met Leu Ala Asn Leu Phe Ser
            500                 505                 510
Met Arg Ser Phe Ile Lys Ile Glu Glu Asp Thr Trp Gln Lys Tyr Tyr
            515                 520                 525
Leu Glu Gly Val Ser Asn Glu Met Tyr Thr Glu Tyr Leu Ser Ser Ala
            530                 535                 540
Phe Val Gly Leu Ser Phe Pro Thr Val Cys Glu Leu Cys Phe Val Lys
545                 550                 555                 560
Leu Lys Leu Leu Met Ile Ala Ile Glu Tyr Lys Ser Ala Asn Arg Glu
                565                 570                 575
Ser Arg Ile Leu Ile Asn Pro Gly Asn His Leu Lys Ile Gln Glu Gly
            580                 585                 590
Thr Leu Gly Phe Phe Ile Ala Ser Asp Ala Lys Glu Val Lys Arg Ala
            595                 600                 605
Phe Phe Tyr Cys Lys Ala Cys His Asp Val Thr Asp Pro Lys Arg
            610                 615                 620
Ile Lys Lys Cys Gly Cys Arg Arg Leu Ile Tyr Phe Glu Asp Glu Gln
625                 630                 635                 640
Pro Pro Thr Leu Ser Pro Lys Lys Gln Arg Asn Gly Gly Met Arg
                645                 650                 655
Asn Ser Pro Asn Thr Ser Pro Lys Leu Met Arg His Asp Pro Leu Leu
                660                 665                 670
```

-continued

```
Ile Pro Gly Asn Asp Gln Ile Asp Asn Met Asp Ser Asn Val Lys Lys
            675                 680                 685

Tyr Asp Ser Thr Gly Met Phe His Trp Cys Ala Pro Lys Glu Ile Glu
        690                 695                 700

Lys Val Ile Leu Thr Arg Ser Glu Ala Ala Met Thr Val Leu Ser Gly
705                 710                 715                 720

His Val Val Val Cys Ile Phe Gly Asp Val Ser Ser Ala Leu Ile Gly
                725                 730                 735

Leu Arg Asn Leu Val Met Pro Leu Arg Ala Ser Asn Phe His Tyr His
            740                 745                 750

Glu Leu Lys His Ile Val Phe Val Gly Ser Ile Glu Tyr Leu Lys Arg
        755                 760                 765

Glu Trp Glu Thr Leu His Asn Phe Pro Lys Val Ser Ile Leu Pro Gly
    770                 775                 780

Thr Pro Leu Ser Arg Ala Asp Leu Arg Ala Val Asn Ile Asn Leu Cys
785                 790                 795                 800

Asp Met Cys Val Ile Leu Ser Ala Asn Gln Asn Asn Ile Asp Asp Thr
                805                 810                 815

Ser Leu Gln Asp Lys Glu Cys Ile Leu Ala Ser Leu Asn Ile Lys Ser
            820                 825                 830

Met Gln Phe Asp Asp Ser Ile Gly Val Leu Gln Ala Asn Ser Gln Gly
        835                 840                 845

Phe Thr Pro Pro Gly Met Asp Arg Ser Ser Pro Asp Asn Ser Pro Val
    850                 855                 860

His Gly Met Leu Arg Gln Pro Ser Ile Thr Thr Gly Val Asn Ile Pro
865                 870                 875                 880

Ile Ile Thr Glu Leu Val Asn Asp Thr Asn Val Gln Phe Leu Asp Gln
                885                 890                 895

Asp Asp Asp Asp Asp Pro Asp Thr Glu Leu Tyr Leu Thr Gln Pro Phe
            900                 905                 910

Ala Cys Gly Thr Ala Phe Ala Val Ser Val Leu Asp Ser Leu Met Ser
        915                 920                 925

Ala Thr Tyr Phe Asn Asp Asn Ile Leu Thr Leu Ile Arg Thr Leu Val
930                 935                 940

Thr Gly Gly Ala Thr Pro Glu Leu Glu Ala Leu Ile Ala Glu Glu Asn
945                 950                 955                 960

Ala Leu Arg Gly Gly Tyr Ser Thr Pro Gln Thr Leu Ala Asn Arg Asp
                965                 970                 975

Arg Cys Arg Val Ala Gln Leu Ala Leu Leu Asp Gly Pro Phe Ala Asp
            980                 985                 990

Leu Gly Asp Gly Gly Cys Tyr Gly Asp Leu Phe Cys Lys Ala Leu Lys
        995                1000                1005

Thr Tyr Asn Met Leu Cys Phe Gly Ile Tyr Arg Leu Arg Asp Ala His
    1010                1015                1020

Leu Ser Thr Pro Ser Gln Cys Thr Lys Arg Tyr Val Ile Thr Asn Pro
1025                1030                1035                1040

Pro Tyr Glu Phe Glu Leu Val Pro Thr Asp Leu Ile Phe Cys Leu Met
                1045                1050                1055

Gln Phe Asp His Asn Ala Gly Gln Ser Arg Ala Ser Leu Ser His Ser
            1060                1065                1070

Ser His Ser Ser Gln Ser Ser Ser Lys Lys Ser Ser Ser Val His Ser
        1075                1080                1085
```

-continued

Ile Pro Ser Thr Ala Asn Arg Pro Asn Arg Pro Lys Ser Arg Glu Ser
     1090                1095                1100

Arg Asp Lys Gln Asn Ala Thr Arg Met Thr Arg Met Gly Gln Ala Glu
1105                1110                1115                1120

Lys Lys Trp Phe Thr Asp Glu Pro Asp Asn Ala Tyr Pro Arg Asn Ile
                1125                1130                1135

Gln Ile Lys Pro Met Ser Thr His Met Ala Asn Gln Ile Asn Gln Tyr
            1140                1145                1150

Lys Ser Thr Ser Ser Leu Ile Pro Pro Ile Arg Glu Val Glu Asp Glu
        1155                1160                1165

Cys Glu Leu Val Pro Thr Asp Leu Ile Phe Cys Leu Met Gln Phe Asp
    1170                1175                1180

His Asn Ala Gly Gln Ser Arg Ala Ser Leu Ser His Ser Ser His Ser
1185                1190                1195                1200

Ser Gln Ser Ser Ser Lys Lys Ser Ser Ser Val His Ser Ile Pro Ser
                1205                1210                1215

Thr Ala Asn Arg Pro Asn Arg Pro Lys Ser Arg Glu Ser Arg Asp Lys
            1220                1225                1230

Gln Asn Ala Thr
        1235

<210> SEQ ID NO 22
<211> LENGTH: 1262
<212> TYPE: PRT
<213> ORGANISM: Drosophila sp.
<220> FEATURE:
<223> OTHER INFORMATION: Drosophila Slo1 (dSlo1)

<400> SEQUENCE: 22

Met Ala Ser Gly Leu Ile Asp Thr Asn Phe Ser Ser Thr Leu Ala Asn
 1               5                  10                  15

Gly Met Ser Gly Cys Asp Gln Ser Thr Val Glu Pro Leu Ala Asp Asp
            20                  25                  30

Pro Thr Asp Ser Pro Phe Asp Ala Asp Cys Leu Lys Val Arg Lys
        35                  40                  45

Tyr Trp Cys Phe Leu Leu Ser Ser Ile Phe Thr Phe Leu Ala Gly Leu
    50                  55                  60

Leu Val Val Leu Leu Trp Arg Ala Phe Ala Phe Val Ser Cys Arg Lys
65                  70                  75                  80

Glu Pro Asp Leu Gly Pro Asn Asp Pro Lys Gln Lys Glu Gln Lys Ala
                85                  90                  95

Ser Arg Asn Lys Gln Glu Phe Glu Gly Thr Phe Met Thr Glu Ala Lys
            100                 105                 110

Asp Trp Ala Gly Glu Leu Ile Ser Gly Gln Thr Thr Thr Gly Arg Ile
        115                 120                 125

Leu Val Val Leu Val Phe Ile Leu Ser Ile Ala Ser Leu Ile Ile Tyr
    130                 135                 140

Phe Val Asp Ala Ser Ser Glu Glu Val Glu Arg Cys Gln Lys Trp Ser
145                 150                 155                 160

Asn Asn Ile Thr Gln Gln Ile Asp Leu Ala Phe Asn Ile Phe Phe Met
                165                 170                 175

Val Tyr Phe Phe Ile Arg Phe Ile Ala Ala Ser Asp Lys Leu Trp Phe
            180                 185                 190

Met Leu Glu Met Tyr Ser Phe Val Asp Tyr Phe Thr Ile Pro Pro Ser
        195                 200                 205

```
Phe Val Ser Ile Tyr Leu Asp Arg Thr Trp Ile Gly Leu Arg Phe Leu
    210                 215                 220

Arg Ala Leu Arg Leu Met Thr Val Pro Asp Ile Leu Gln Tyr Leu Asn
225                 230                 235                 240

Val Leu Lys Thr Ser Ser Ile Arg Leu Ala Gln Leu Val Ser Ile
                245                 250                 255

Phe Ile Ser Val Trp Leu Thr Ala Ala Gly Ile Ile His Leu Leu Glu
            260                 265                 270

Asn Ser Gly Asp Pro Leu Asp Phe Asn Asn Ala His Arg Leu Ser Tyr
        275                 280                 285

Trp Thr Cys Val Tyr Phe Leu Ile Val Thr Met Ser Thr Val Gly Tyr
    290                 295                 300

Gly Asp Val Tyr Cys Glu Thr Val Leu Gly Arg Thr Phe Leu Val Phe
305                 310                 315                 320

Phe Leu Leu Val Gly Leu Ala Val Phe Ala Ser Trp Ile Pro Glu Ile
                325                 330                 335

Thr Glu Leu Ala Ala Gln Arg Ser Lys Tyr Gly Gly Thr Tyr Ser Lys
            340                 345                 350

Asp Pro Arg Lys Arg His Ile Val Val Cys Gly His Ile Thr Tyr Glu
        355                 360                 365

Ser Val Ser His Phe Leu Lys Asp Phe Leu His Glu Asp Arg Glu Asp
    370                 375                 380

Val Asp Val Glu Val Val Phe Leu His Arg Lys Pro Pro Asp Leu Glu
385                 390                 395                 400

Leu Glu Gly Leu Phe Lys Arg His Phe Thr Thr Val Glu Phe Phe Gln
                405                 410                 415

Gly Thr Ile Met Asn Pro Ile Asp Leu Gln Arg Val Lys Val His Glu
            420                 425                 430

Ala Asp Ala Cys Leu Val Leu Ala Asn Lys Tyr Cys Gln Asp Pro Asp
        435                 440                 445

Ala Glu Asp Ala Ala Asn Ile Met Arg Val Ile Ser Ile Lys Asn Tyr
    450                 455                 460

Ser Asp Asp Ile Arg Val Ile Ile Gln Leu Met Gln Tyr His Asn Lys
465                 470                 475                 480

Ala Tyr Leu Leu Asn Ile Pro Ser Trp Asp Trp Lys Gln Gly Asp Asp
                485                 490                 495

Val Ile Cys Leu Ala Glu Leu Lys Leu Gly Phe Ile Ala Gln Ser Cys
            500                 505                 510

Leu Ala Pro Gly Phe Ser Thr Met Met Ala Asn Leu Phe Ala Met Arg
        515                 520                 525

Ser Phe Lys Thr Ser Pro Asp Met Gln Ser Trp Thr Asn Asp Tyr Leu
    530                 535                 540

Arg Gly Thr Gly Met Glu Met Tyr Thr Glu Thr Leu Ser Pro Thr Phe
545                 550                 555                 560

Ile Gly Ile Pro Phe Ala Gln Ala Thr Glu Leu Cys Phe Ser Lys Leu
                565                 570                 575

Lys Leu Leu Leu Leu Ala Ile Glu Ile Lys Gly Ala Glu Glu Gly Ala
            580                 585                 590

Asp Ser Lys Ile Ser Ile Asn Pro Arg Gly Ala Lys Ile Gln Ala Asn
        595                 600                 605

Thr Gln Gly Phe Phe Ile Ala Gln Ser Ala Asp Glu Val Lys Arg Ala
    610                 615                 620

Trp Phe Tyr Cys Lys Ala Cys His Glu Asp Ile Lys Asp Glu Thr Leu
```

-continued

```
         625                 630                 635                 640
Ile Lys Lys Cys Lys Cys Lys Asn Leu Thr Val Gln Pro Arg Ser Lys
                645                 650                 655
Phe Asp Asp Leu Gly Asp Ile Thr Arg Asp Arg Glu Asp Thr Asn Leu
                660                 665                 670
Leu Asn Arg Asn Val Arg Arg Pro Asn Gly Thr Gly Asn Gly Thr Gly
                675                 680                 685
Gly Met His His Met Asn Ser Thr Arg Ala Ala Ala Ala Ala Ala
            690                 695                 700
Ala Ala Gly Lys Gln Val Asn Lys Val Lys Pro Thr Val Asn Val Ser
705                 710                 715                 720
Arg Gln Val Glu Gly Gln Val Ile Ser Pro Ser Gln Tyr Asn Arg Pro
                725                 730                 735
Thr Ser Arg Ser Ser Gly Thr Gly Thr Gln Asn Gln Asn Gly Gly Val
                740                 745                 750
Ser Leu Pro Ala Gly Ile Ala Asp Asp Gln Ser Lys Asp Phe Asp Phe
                755                 760                 765
Glu Lys Thr Glu Met Lys Tyr Asp Ser Thr Gly Met Phe His Trp Ser
770                 775                 780
Pro Ala Lys Ser Leu Gln Asp Cys Ile Leu Asp Arg Asn Gln Ala Ala
785                 790                 795                 800
Met Thr Val Leu Asn Gly His Val Val Cys Leu Phe Ala Asp Pro
                805                 810                 815
Asp Ser Pro Leu Ile Gly Leu Arg Asn Leu Val Met Pro Leu Arg Ala
                820                 825                 830
Ser Asn Phe His Tyr His Glu Leu Lys His Val Val Ile Val Gly Ser
                835                 840                 845
Val Asp Tyr Ile Arg Arg Glu Trp Lys Met Leu Gln Asn Leu Pro Lys
            850                 855                 860
Ile Ser Val Leu Asn Gly Ser Pro Leu Ser Arg Ala Asp Leu Arg Ala
865                 870                 875                 880
Val Asn Val Asn Leu Cys Asp Met Cys Cys Ile Leu Ser Ala Lys Val
                885                 890                 895
Pro Ser Asn Asp Asp Pro Thr Leu Ala Asp Lys Glu Ala Ile Leu Ala
                900                 905                 910
Ser Leu Asn Ile Lys Ala Met Thr Phe Asp Asp Thr Ile Gly Val Leu
            915                 920                 925
Ser Gln Arg Gly Pro Glu Phe Asp Asn Leu Ser Ala Thr Ala Gly Ser
            930                 935                 940
Pro Ile Val Leu Gln Arg Arg Gly Ser Val Tyr Gly Ala Asn Val Pro
945                 950                 955                 960
Met Ile Thr Glu Leu Val Asn Asp Gly Asn Val Gln Phe Leu Asp Gln
                965                 970                 975
Asp Asp Asp Asp Pro Asp Thr Glu Leu Tyr Leu Thr Gln Pro Phe
                980                 985                 990
Ala Cys Gly Thr Ala Phe Ala Val Ser Val Leu Asp Ser Leu Met Ser
            995                 1000                1005
Thr Thr Tyr Phe Asn Gln Asn Ala Leu Thr Leu Ile Arg Ser Leu Ile
    1010                1015                1020
Thr Gly Gly Ala Thr Pro Glu Leu Glu Leu Ile Leu Ala Glu Gly Ala
1025                1030                1035                1040
Gly Leu Arg Gly Gly Tyr Ser Thr Val Glu Ser Leu Ser Asn Arg Asp
                1045                1050                1055
```

```
Arg Cys Arg Val Gly Gln Ile Ser Leu Tyr Asp Gly Pro Leu Ala Gln
        1060                1065                1070

Phe Gly Glu Cys Gly Lys Tyr Gly Asp Leu Phe Val Ala Ala Leu Lys
    1075                1080                1085

Ser Tyr Gly Met Leu Cys Ile Gly Leu Tyr Arg Phe Arg Asp Thr Ser
    1090                1095                1100

Ser Ser Cys Asp Ala Ser Ser Lys Arg Tyr Val Ile Thr Asn Pro Pro
1105                1110                1115                1120

Asp Asp Phe Ser Leu Leu Pro Thr Asp Gln Val Phe Val Leu Met Gln
            1125                1130                1135

Phe Asp Pro Gly Leu Glu Tyr Lys Pro Pro Ala Val Arg Ala Pro Ala
        1140                1145                1150

Gly Gly Arg Gly Thr Asn Thr Gln Gly Ser Gly Val Gly Gly Gly Gly
        1155                1160                1165

Ser Asn Lys Asp Asp Asn Ser Leu Ser Asn Arg Asp Arg Cys Arg Val
    1170                1175                1180

Gly Gln Ile Ser Leu Tyr Asp Gly Pro Leu Ala Gln Phe Gly Glu Cys
1185                1190                1195                1200

Gly Lys Tyr Gly Asp Leu Phe Val Ala Ala Leu Lys Ser Tyr Gly Met
            1205                1210                1215

Leu Cys Ile Gly Leu Tyr Arg Phe Arg Asp Thr Ser Ser Ser Cys Asp
        1220                1225                1230

Ala Ser Ser Lys Arg Tyr Val Ile Thr Asn Pro Pro Asp Asp Phe Ser
        1235                1240                1245

Leu Leu Pro Thr Asp Gln Val Phe Val Leu Met Gln Phe Asp
    1250                1255                1260

<210> SEQ ID NO 23
<211> LENGTH: 24
<212> TYPE: DNA
<213> ORGANISM: Artificial Sequence
<220> FEATURE:
<223> OTHER INFORMATION: Description of Artificial Sequence:sense
      oligonucleotide

<400> SEQUENCE: 23
gtggatgata ccgacatgct ggac                                    24

<210> SEQ ID NO 24
<211> LENGTH: 24
<212> TYPE: DNA
<213> ORGANISM: Artificial Sequence
<220> FEATURE:
<223> OTHER INFORMATION: Description of Artificial Sequence:antisense
      oligonucleotide

<400> SEQUENCE: 24
gagaccacct ctctcccgtg tcgt                                    24

<210> SEQ ID NO 25
<211> LENGTH: 26
<212> TYPE: DNA
<213> ORGANISM: Artificial Sequence
<220> FEATURE:
<223> OTHER INFORMATION: Description of Artificial Sequence:mSLo3 (S4 to
      S5) sense primer

<400> SEQUENCE: 25
ctcgaactcc ctaaaatctt acagat                                  26
```

```
<210> SEQ ID NO 26
<211> LENGTH: 28
<212> TYPE: DNA
<213> ORGANISM: Artificial Sequence
<220> FEATURE:
<223> OTHER INFORMATION: Description of Artificial Sequence:mSlo3 (S4 to
      S5) antisense primer

<400> SEQUENCE: 26
ttccgttgag ccagggtca ccagaatt                                            28

<210> SEQ ID NO 27
<211> LENGTH: 22
<212> TYPE: DNA
<213> ORGANISM: Artificial Sequence
<220> FEATURE:
<223> OTHER INFORMATION: Description of Artificial Sequence:mSlo3 (S8 to
      S9) sense primer

<400> SEQUENCE: 27
tctgctttgt gaagctaaat ct                                                 22

<210> SEQ ID NO 28
<211> LENGTH: 23
<212> TYPE: DNA
<213> ORGANISM: Artificial Sequence
<220> FEATURE:
<223> OTHER INFORMATION: Description of Artificial Sequence:mSlo3 (S8 to
      S9) antisense primer

<400> SEQUENCE: 28
tttcaaagcc tctttagcgg taa                                                23

<210> SEQ ID NO 29
<211> LENGTH: 26
<212> TYPE: DNA
<213> ORGANISM: Artificial Sequence
<220> FEATURE:
<223> OTHER INFORMATION: Description of Artificial Sequence:mSlo3 (S9 to
      S10) sense primer

<400> SEQUENCE: 29
ttatgcctgg atctgcactc tacatg                                             26

<210> SEQ ID NO 30
<211> LENGTH: 23
<212> TYPE: DNA
<213> ORGANISM: Artificial Sequence
<220> FEATURE:
<223> OTHER INFORMATION: Description of Artificial Sequence:mSlo3 (S9 to
      S10) antisense primer

<400> SEQUENCE: 30
atagtttccg tctactaccg aaa                                                23

<210> SEQ ID NO 31
<211> LENGTH: 27
<212> TYPE: DNA
<213> ORGANISM: Artificial Sequence
<220> FEATURE:
<223> OTHER INFORMATION: Description of Artificial Sequence:control
      human beta-actin sense primer

<400> SEQUENCE: 31
gatgatatcg ccgcgctcgt cgtcgac                                            27
```

```
<210> SEQ ID NO 32
<211> LENGTH: 27
<212> TYPE: DNA
<213> ORGANISM: Artificial Sequence
<220> FEATURE:
<223> OTHER INFORMATION: Description of Artificial Sequence:control
      human beta-actin antisense primer

<400> SEQUENCE: 32
tcggtccagg tctgcgtcct accgtac                                           27

<210> SEQ ID NO 33
<211> LENGTH: 28
<212> TYPE: DNA
<213> ORGANISM: Artificial Sequence
<220> FEATURE:
<223> OTHER INFORMATION: Description of Artificial Sequence:northern
      blot sense primer

<400> SEQUENCE: 33
cggaaacgtc atgtacaatc gaaatcca                                          28

<210> SEQ ID NO 34
<211> LENGTH: 28
<212> TYPE: DNA
<213> ORGANISM: Artificial Sequence
<220> FEATURE:
<223> OTHER INFORMATION: Description of Artificial Sequence:northern
      blot antisense primer

<400> SEQUENCE: 34
ttccgttgag ccagggqtca ccagaatt                                          28

<210> SEQ ID NO 35
<211> LENGTH: 24
<212> TYPE: DNA
<213> ORGANISM: Artificial Sequence
<220> FEATURE:
<223> OTHER INFORMATION: Description of Artificial Sequence:human testis
      cDNA library primer

<400> SEQUENCE: 35
ggcagcgctc attctttcct cctt                                              24

<210> SEQ ID NO 36
<211> LENGTH: 24
<212> TYPE: DNA
<213> ORGANISM: Artificial Sequence
<220> FEATURE:
<223> OTHER INFORMATION: Description of Artificial Sequence:human testis
      cDNA library primer

<400> SEQUENCE: 36
tgcccaaaac ctcaacccaa aata                                              24

<210> SEQ ID NO 37
<211> LENGTH: 4
<212> TYPE: PRT
<213> ORGANISM: Mus musculus
<220> FEATURE:
<221> NAME/KEY: PEPTIDE
<222> LOCATION: (1)..(4)
<223> OTHER INFORMATION: mSlo3 Region A peptide starting at amino acid
      792

<400> SEQUENCE: 37

Ile Ala Val Asn
  1
```

```
<210> SEQ ID NO 38
<211> LENGTH: 4
<212> TYPE: PRT
<213> ORGANISM: Mus musculus
<220> FEATURE:
<221> NAME/KEY: PEPTIDE
<222> LOCATION: (1)..(4)
<223> OTHER INFORMATION: mSlo3 Region A peptide ending at amino acid
      870

<400> SEQUENCE: 38

Leu Thr Glu Leu
  1

<210> SEQ ID NO 39
<211> LENGTH: 4
<212> TYPE: PRT
<213> ORGANISM: Mus musculus
<220> FEATURE:
<221> NAME/KEY: PEPTIDE
<222> LOCATION: (1)..(4)
<223> OTHER INFORMATION: mSlo1 Region A peptide starting at amino acid
      793

<400> SEQUENCE: 39

Arg Ala Val Asn
  1

<210> SEQ ID NO 40
<211> LENGTH: 4
<212> TYPE: PRT
<213> ORGANISM: Mus musculus
<220> FEATURE:
<221> NAME/KEY: PEPTIDE
<222> LOCATION: (1)..(4)
<223> OTHER INFORMATION: mSlo1 Region A peptide ending at amino acid
      885

<400> SEQUENCE: 40

Ile Thr Glu Leu
  1

<210> SEQ ID NO 41
<211> LENGTH: 4
<212> TYPE: PRT
<213> ORGANISM: Mus musculus
<220> FEATURE:
<221> NAME/KEY: PEPTIDE
<222> LOCATION: (1)..(4)
<223> OTHER INFORMATION: mSlo3 Region B peptide starting at amino acid
      871

<400> SEQUENCE: 41

Lys Asn Pro Ser
  1

<210> SEQ ID NO 42
<211> LENGTH: 4
<212> TYPE: PRT
<213> ORGANISM: Mus musculus
<220> FEATURE:
<221> NAME/KEY: PEPTIDE
<222> LOCATION: (1)..(4)
<223> OTHER INFORMATION: mSlo3 Region B peptide ending at amino acid
      906

<400> SEQUENCE: 42

Gly Ala Val Phe
```

-continued

```
<210> SEQ ID NO 43
<211> LENGTH: 4
<212> TYPE: PRT
<213> ORGANISM: Mus musculus
<220> FEATURE:
<221> NAME/KEY: PEPTIDE
<222> LOCATION: (1)..(4)
<223> OTHER INFORMATION: mSlo1 Region B peptide starting at amino acid
      886

<400> SEQUENCE: 43

Val Asn Asp Thr
  1

<210> SEQ ID NO 44
<211> LENGTH: 4
<212> TYPE: PRT
<213> ORGANISM: Mus musculus
<220> FEATURE:
<221> NAME/KEY: PEPTIDE
<222> LOCATION: (1)..(4)
<223> OTHER INFORMATION: mSlo1 Region B peptide ending at amino acid
      918

<400> SEQUENCE: 44

Gly Thr Ala Phe
  1

<210> SEQ ID NO 45
<211> LENGTH: 4
<212> TYPE: PRT
<213> ORGANISM: Artificial Sequence
<220> FEATURE:
<223> OTHER INFORMATION: Description of Artificial Sequence:hybrid of
      mSlo1 and mSlo3 sequences at C-terminal end of chimera
      Region B fragment

<400> SEQUENCE: 45

Gly Ala Ala Phe
  1

<210> SEQ ID NO 46
<211> LENGTH: 4
<212> TYPE: PRT
<213> ORGANISM: Mus musculus
<220> FEATURE:
<221> NAME/KEY: PEPTIDE
<222> LOCATION: (1)..(4)
<223> OTHER INFORMATION: mSlo3 Region C peptide starting at amino acid
      899

<400> SEQUENCE: 46

Ser Thr Ser Phe
  1

<210> SEQ ID NO 47
<211> LENGTH: 4
<212> TYPE: PRT
<213> ORGANISM: Mus musculus
<220> FEATURE:
<221> NAME/KEY: PEPTIDE
<222> LOCATION: (1)..(4)
<223> OTHER INFORMATION: mSlo3 Region C peptide ending at amino acid
      941

<400> SEQUENCE: 47

Ser Glu Met Glu
```

```
<210> SEQ ID NO 48
<211> LENGTH: 4
<212> TYPE: PRT
<213> ORGANISM: Mus musculus
<220> FEATURE:
<221> NAME/KEY: PEPTIDE
<222> LOCATION: (1)..(4)
<223> OTHER INFORMATION: mSlo1 Region C peptide starting at amino acid
      909

<400> SEQUENCE: 48

Thr Gln Pro Phe
 1

<210> SEQ ID NO 49
<211> LENGTH: 4
<212> TYPE: PRT
<213> ORGANISM: Mus musculus
<220> FEATURE:
<221> NAME/KEY: PEPTIDE
<222> LOCATION: (1)..(4)
<223> OTHER INFORMATION: mSlo1 Region C peptide ending at amino acid
      963

<400> SEQUENCE: 49

Pro Glu Leu Glu
 1

<210> SEQ ID NO 50
<211> LENGTH: 4
<212> TYPE: PRT
<213> ORGANISM: Mus musculus
<220> FEATURE:
<221> NAME/KEY: PEPTIDE
<222> LOCATION: (1)..(4)
<223> OTHER INFORMATION: mSlo3 Region D peptide starting at amino acid
      939

<400> SEQUENCE: 50

Glu Met Glu His
 1

<210> SEQ ID NO 51
<211> LENGTH: 4
<212> TYPE: PRT
<213> ORGANISM: Mus musculus
<220> FEATURE:
<221> NAME/KEY: PEPTIDE
<222> LOCATION: (1)..(4)
<223> OTHER INFORMATION: mSlo3 Region D peptide ending at amino acid
      1034

<400> SEQUENCE: 51

His Leu Leu Pro
 1

<210> SEQ ID NO 52
<211> LENGTH: 4
<212> TYPE: PRT
<213> ORGANISM: Mus musculus
<220> FEATURE:
<221> NAME/KEY: PEPTIDE
<222> LOCATION: (1)..(4)
<223> OTHER INFORMATION: mSlo1 Region D peptide starting at amino acid
      951

<400> SEQUENCE: 52
```

```
Glu Leu Glu Ala
  1

<210> SEQ ID NO 53
<211> LENGTH: 4
<212> TYPE: PRT
<213> ORGANISM: Mus musculus
<220> FEATURE:
<221> NAME/KEY: PEPTIDE
<222> LOCATION: (1)..(4)
<223> OTHER INFORMATION: mSlo1 Region D peptide ending at amino acid
      1048

<400> SEQUENCE: 53

Glu Leu Val Pro
  1
```